(12) United States Patent
Nawana et al.

(10) Patent No.: US 12,053,284 B2
(45) Date of Patent: Aug. 6, 2024

(54) DERMAL PATCH FOR COLLECTING A PHYSIOLOGICAL SAMPLE

(71) Applicant: Satio, Inc., Boston, MA (US)

(72) Inventors: Namal Nawana, Weston, MA (US); Ziad Tarik Al-Shamsie, San Diego, CA (US)

(73) Assignee: Satio, Inc., Boston, MA (US)

(*) Notice: Subject to any disclaimer, the term of this patent is extended or adjusted under 35 U.S.C. 154(b) by 0 days.

(21) Appl. No.: 17/971,142

(22) Filed: Oct. 21, 2022

(65) Prior Publication Data

US 2023/0144502 A1 May 11, 2023

Related U.S. Application Data

(63) Continuation-in-part of application No. 17/521,466, filed on Nov. 8, 2021, now Pat. No. 11,510,602.

(51) Int. Cl.
*A61B 5/00* (2006.01)
*A61B 5/15* (2006.01)
*A61B 5/151* (2006.01)

(52) U.S. Cl.
CPC .. *A61B 5/150267* (2013.01); *A61B 5/150351* (2013.01); *A61B 5/150358* (2013.01); *A61B 5/15109* (2013.01); *A61B 5/15117* (2013.01); *A61B 5/15144* (2013.01); *A61B 5/6833* (2013.01)

(58) Field of Classification Search
CPC ........ A61B 5/150267; A61B 5/150351; A61B 5/150358; A61B 5/15109; A61B 5/15117; A61B 5/15144; A61B 5/6833
See application file for complete search history.

(56) References Cited

U.S. PATENT DOCUMENTS

| | | |
|---|---|---|
| 5,015,228 A | 5/1991 | Columbus et al. |
| 5,338,308 A | 8/1994 | Wilk |
| 5,441,490 A | 8/1995 | Svedman |
| 5,527,288 A | 6/1996 | Gross et al. |
| 5,602,037 A | 2/1997 | Ostgaard et al. |
| 5,636,640 A * | 6/1997 | Staehlin ........... A61B 5/150419 600/577 |

(Continued)

FOREIGN PATENT DOCUMENTS

| | | |
|---|---|---|
| AU | 2006283345 A1 | 3/2007 |
| AU | 2016266112 A1 | 12/2016 |

(Continued)

OTHER PUBLICATIONS

English machine translation of JP-2004024164-A, patents.google.com, 8 pages.

(Continued)

*Primary Examiner* — May A Abouelela
(74) *Attorney, Agent, or Firm* — Potomac Law Group, PLLC; John J. Penny, Jr.

(57) ABSTRACT

A device for collecting a physiological sample from a subject includes a lancet with a needle that is configured to puncture the subject's skin and a cartridge configured to engage with the lancet. The lancet is configured to transition the needle from an undeployed position to a deployed position in response to engagement with the cartridge, thereby allowing the needle to puncture the subject's skin.

6 Claims, 34 Drawing Sheets

(56) References Cited

U.S. PATENT DOCUMENTS

| | | | |
|---|---|---|---|
| 5,680,872 A * | 10/1997 | Sesekura | A61B 5/15111 |
| | | | 600/583 |
| 5,848,991 A | 12/1998 | Gross et al. | |
| 5,997,501 A | 12/1999 | Gross et al. | |
| 6,234,980 B1 * | 5/2001 | Bell | A61B 5/150305 |
| | | | 604/314 |
| 6,315,985 B1 | 11/2001 | Wu et al. | |
| 6,454,140 B1 | 9/2002 | Jinks | |
| 6,500,150 B1 | 12/2002 | Gross et al. | |
| 6,506,168 B1 * | 1/2003 | Fathallah | A61B 5/150022 |
| | | | 600/578 |
| 6,524,284 B1 | 2/2003 | Marshall | |
| 6,610,273 B2 | 8/2003 | Wu et al. | |
| 6,623,457 B1 | 9/2003 | Rosenberg | |
| 6,644,517 B2 | 11/2003 | Thiel et al. | |
| 6,689,118 B2 | 2/2004 | Alchas et al. | |
| 6,776,776 B2 | 8/2004 | Alchas et al. | |
| 6,780,171 B2 | 8/2004 | Gabel et al. | |
| 6,796,429 B2 | 9/2004 | Cameron et al. | |
| 6,808,506 B2 | 10/2004 | Lastovich et al. | |
| 6,893,655 B2 | 5/2005 | Flanigan et al. | |
| 6,932,082 B2 | 8/2005 | Stein | |
| 6,960,193 B2 | 11/2005 | Rosenberg | |
| 6,994,691 B2 | 2/2006 | Ejlersen | |
| 7,004,928 B2 | 2/2006 | Aceti et al. | |
| 7,083,592 B2 | 8/2006 | Lastovich et al. | |
| 7,101,534 B1 | 9/2006 | Schultz et al. | |
| 7,156,838 B2 | 1/2007 | Gabel et al. | |
| 7,175,642 B2 | 2/2007 | Briggs et al. | |
| 7,182,955 B2 | 2/2007 | Hart et al. | |
| 7,250,037 B2 | 7/2007 | Shermer et al. | |
| 7,252,651 B2 | 8/2007 | Haider et al. | |
| 7,282,058 B2 | 10/2007 | Levin et al. | |
| 7,308,893 B2 | 12/2007 | Boot | |
| 7,435,415 B2 | 10/2008 | Gelber | |
| 7,637,891 B2 | 12/2009 | Wall | |
| 7,651,475 B2 | 1/2010 | Angel et al. | |
| 7,678,079 B2 | 3/2010 | Shermer et al. | |
| 7,846,488 B2 | 12/2010 | Johnson et al. | |
| 7,905,866 B2 | 3/2011 | Haider et al. | |
| 8,048,019 B2 | 11/2011 | Nisato et al. | |
| 8,057,842 B2 | 11/2011 | Choi et al. | |
| 8,066,680 B2 | 11/2011 | Alchas et al. | |
| 8,079,960 B2 | 12/2011 | Briggs et al. | |
| 8,104,469 B2 | 1/2012 | Dams | |
| 8,108,023 B2 | 1/2012 | Mir et al. | |
| 8,157,768 B2 | 4/2012 | Haider et al. | |
| 8,206,336 B2 | 6/2012 | Shantha | |
| 8,246,582 B2 | 8/2012 | Angel et al. | |
| 8,246,893 B2 | 8/2012 | Ferguson et al. | |
| 8,252,268 B2 | 8/2012 | Slowey et al. | |
| 8,267,889 B2 | 9/2012 | Cantor et al. | |
| 8,303,518 B2 | 11/2012 | Aceti et al. | |
| D681,195 S | 4/2013 | Skulley et al. | |
| 8,409,140 B2 | 4/2013 | Ejlersen et al. | |
| 8,414,503 B2 | 4/2013 | Briggs et al. | |
| 8,414,959 B2 | 4/2013 | Hye-Ok et al. | |
| 8,430,097 B2 | 4/2013 | Jinks et al. | |
| 8,459,253 B2 | 6/2013 | Howgill | |
| 8,491,500 B2 | 7/2013 | Briggs et al. | |
| 8,496,601 B2 | 7/2013 | Briggs et al. | |
| D687,550 S | 8/2013 | Moeckly et al. | |
| D687,551 S | 8/2013 | Moeckly et al. | |
| D687,945 S | 8/2013 | Brewer et al. | |
| D687,946 S | 8/2013 | Brewer et al. | |
| D687,947 S | 8/2013 | Brewer et al. | |
| 8,512,244 B2 | 8/2013 | Jennewine | |
| 8,517,019 B2 | 8/2013 | Brewer et al. | |
| 8,554,317 B2 | 10/2013 | Duan | |
| 8,556,861 B2 | 10/2013 | Tsals | |
| 8,561,795 B2 | 10/2013 | Schott | |
| D693,921 S | 11/2013 | Burton et al. | |
| 8,602,271 B2 | 12/2013 | Winker et al. | |
| 8,603,040 B2 | 12/2013 | Haider et al. | |
| 8,608,889 B2 | 12/2013 | Sever et al. | |
| 8,622,963 B2 | 1/2014 | Wase et al. | |
| 8,696,619 B2 | 4/2014 | Schnall | |
| 8,696,637 B2 | 4/2014 | Ross | |
| D705,422 S | 5/2014 | Burton et al. | |
| 8,715,232 B2 | 5/2014 | Yodfat et al. | |
| 8,740,014 B2 | 6/2014 | Purkins et al. | |
| 8,741,377 B2 | 6/2014 | Choi et al. | |
| 8,784,363 B2 | 7/2014 | Frederickson et al. | |
| 8,808,202 B2 * | 8/2014 | Brancazio | A61B 5/150022 |
| | | | 600/583 |
| 8,808,786 B2 | 8/2014 | Jinks et al. | |
| 8,814,009 B2 | 8/2014 | Hodson et al. | |
| 8,814,035 B2 | 8/2014 | Stuart | |
| 8,821,412 B2 | 9/2014 | Gonzalez-Zugasti et al. | |
| 8,821,446 B2 | 9/2014 | Trautman et al. | |
| 8,821,779 B2 | 9/2014 | Ferguson et al. | |
| 8,827,971 B2 | 9/2014 | Gonzalez-Zugasti et al. | |
| 8,870,821 B2 | 10/2014 | Laufer | |
| 8,900,180 B2 | 12/2014 | Wolter et al. | |
| 8,900,194 B2 | 12/2014 | Clarke et al. | |
| 8,945,071 B2 | 2/2015 | Christensen | |
| 8,961,431 B2 | 2/2015 | Roe et al. | |
| 9,022,973 B2 | 5/2015 | Sexton et al. | |
| 9,033,898 B2 | 5/2015 | Chickering, III et al. | |
| 9,041,541 B2 | 5/2015 | Levinson et al. | |
| D733,290 S | 6/2015 | Burton et al. | |
| 9,067,031 B2 | 6/2015 | Jinks et al. | |
| 9,072,664 B2 | 7/2015 | Stein et al. | |
| 9,089,661 B2 | 7/2015 | Stuart et al. | |
| 9,089,677 B2 | 7/2015 | Soo et al. | |
| 9,113,836 B2 | 8/2015 | Bernstein et al. | |
| 9,119,578 B2 | 9/2015 | Haghgooie et al. | |
| 9,119,945 B2 | 9/2015 | Simons et al. | |
| 9,133,024 B2 | 9/2015 | Phan et al. | |
| 9,144,651 B2 | 9/2015 | Stuart | |
| 9,144,671 B2 | 9/2015 | Cantor et al. | |
| 9,173,994 B2 | 11/2015 | Ziaie et al. | |
| 9,174,035 B2 | 11/2015 | Ringsred et al. | |
| 9,186,097 B2 | 11/2015 | Frey et al. | |
| 9,227,021 B2 | 1/2016 | Buss | |
| 9,289,763 B2 | 3/2016 | Berthier et al. | |
| 9,289,925 B2 | 3/2016 | Ferguson et al. | |
| 9,289,968 B2 | 3/2016 | Sever et al. | |
| 9,295,417 B2 | 3/2016 | Haghgooie et al. | |
| 9,295,987 B2 | 3/2016 | Kelly et al. | |
| 9,339,956 B2 | 5/2016 | Rendon | |
| 9,380,972 B2 * | 7/2016 | Fletcher | A61B 5/15101 |
| 9,380,973 B2 * | 7/2016 | Fletcher | A61M 1/36 |
| 9,468,404 B2 | 10/2016 | Hayden | |
| 9,480,428 B2 | 11/2016 | Colin et al. | |
| 9,504,813 B2 | 11/2016 | Buss | |
| 9,522,225 B2 * | 12/2016 | Chong | A61M 5/14248 |
| 9,549,700 B2 * | 1/2017 | Fletcher | G01N 1/34 |
| 9,555,187 B2 | 1/2017 | Sonderegger et al. | |
| 9,566,393 B2 | 2/2017 | Iwase et al. | |
| 9,579,461 B2 | 2/2017 | Sonderegger et al. | |
| 9,623,087 B2 | 4/2017 | Zhang et al. | |
| 9,642,895 B2 | 5/2017 | Dai et al. | |
| 9,643,229 B2 | 5/2017 | Wilson et al. | |
| 9,675,675 B2 | 6/2017 | Zhang et al. | |
| 9,675,752 B2 | 6/2017 | Christensen | |
| 9,682,222 B2 | 6/2017 | Burton et al. | |
| 9,693,950 B2 | 7/2017 | Determan et al. | |
| 9,694,149 B2 | 7/2017 | Jinks et al. | |
| 9,717,850 B2 | 8/2017 | Sonderegger | |
| 9,724,462 B2 | 8/2017 | Rotem | |
| 9,730,624 B2 | 8/2017 | Gonzalez-Zugasti et al. | |
| 9,770,578 B2 | 9/2017 | Chowdhury | |
| 9,775,551 B2 | 10/2017 | Bernstein et al. | |
| 9,782,574 B2 | 10/2017 | Simmers | |
| 9,789,249 B2 | 10/2017 | Frederickson et al. | |
| 9,789,299 B2 | 10/2017 | Simmers | |
| 9,844,631 B2 | 12/2017 | Bureau | |
| 9,849,270 B2 | 12/2017 | Stockholm | |
| D808,515 S | 1/2018 | Atkin et al. | |
| 9,861,580 B2 | 1/2018 | Mueting et al. | |
| 9,861,801 B2 | 1/2018 | Baker et al. | |
| 9,872,975 B2 | 1/2018 | Burton et al. | |
| 9,884,151 B2 | 2/2018 | Sullivan et al. | |

(56) References Cited

U.S. PATENT DOCUMENTS

| | | |
|---|---|---|
| 9,895,520 B2 | 2/2018 | Burton et al. |
| 9,956,170 B2 | 5/2018 | Cantor et al. |
| 9,968,767 B1 | 5/2018 | Hasan et al. |
| 9,987,629 B2 | 6/2018 | Berthier et al. |
| 9,993,189 B2 | 6/2018 | Phan et al. |
| 10,004,887 B2 | 6/2018 | Gross et al. |
| 10,010,676 B2 | 7/2018 | Bureau |
| 10,010,706 B2 | 7/2018 | Gonzalez et al. |
| 10,010,707 B2 | 7/2018 | Colburn et al. |
| 10,016,315 B2 * | 7/2018 | Letourneau ............ A61F 13/15 |
| 10,029,845 B2 | 7/2018 | Jinks |
| 10,035,008 B2 | 7/2018 | Brandwein et al. |
| 10,076,649 B2 | 9/2018 | Gilbert et al. |
| 10,080,843 B2 | 9/2018 | Bureau |
| 10,080,846 B2 | 9/2018 | Sonderegger et al. |
| 10,099,043 B2 | 10/2018 | Berry et al. |
| 10,105,524 B2 | 10/2018 | Meyer et al. |
| 10,111,807 B2 | 10/2018 | Baker et al. |
| D834,704 S | 11/2018 | Atkin et al. |
| 10,154,957 B2 | 12/2018 | Zhang et al. |
| 10,155,334 B2 | 12/2018 | Rendon |
| 10,183,156 B2 | 1/2019 | Ross et al. |
| 10,188,335 B2 | 1/2019 | Haghgooie et al. |
| D840,020 S | 2/2019 | Howgill |
| 10,201,691 B2 | 2/2019 | Berry et al. |
| 10,232,157 B2 | 3/2019 | Berry et al. |
| 10,232,160 B2 | 3/2019 | Baker et al. |
| 10,248,765 B1 * | 4/2019 | Holmes ............ A61B 5/150022 |
| 10,265,484 B2 | 4/2019 | Stuart et al. |
| 10,272,214 B2 | 4/2019 | Child et al. |
| 10,300,260 B2 | 5/2019 | Wirtanen et al. |
| 10,307,578 B2 | 6/2019 | Frederickson et al. |
| 10,315,021 B2 | 6/2019 | Frederickson et al. |
| 10,327,990 B2 | 6/2019 | Egeland et al. |
| 10,328,248 B2 | 6/2019 | Baker et al. |
| 10,335,560 B2 | 7/2019 | Stein et al. |
| 10,335,562 B2 | 7/2019 | Jinks et al. |
| 10,335,563 B2 | 7/2019 | Brewer et al. |
| 10,357,610 B2 | 7/2019 | Sonderegger |
| 10,384,047 B2 | 8/2019 | Simmers |
| 10,391,290 B2 | 8/2019 | Burton et al. |
| 10,398,885 B2 | 9/2019 | Frits et al. |
| 10,406,339 B2 | 9/2019 | Simmers |
| 10,410,838 B2 | 9/2019 | Hanson et al. |
| 10,426,390 B2 | 10/2019 | Berthier et al. |
| 10,426,739 B2 | 10/2019 | Knutson |
| 10,478,346 B2 | 11/2019 | Knutson |
| 10,492,716 B2 | 12/2019 | Berthier et al. |
| 10,507,286 B2 | 12/2019 | Egeland et al. |
| 10,518,071 B2 | 12/2019 | Kulkarni |
| D872,853 S | 1/2020 | Stuart et al. |
| 10,525,463 B2 | 1/2020 | Kelly et al. |
| 10,542,922 B2 | 1/2020 | Sia et al. |
| 10,543,310 B2 | 1/2020 | Bernstein et al. |
| 10,549,079 B2 | 2/2020 | Burton et al. |
| 10,568,937 B2 | 2/2020 | Hattersley et al. |
| D878,544 S | 3/2020 | Stuart et al. |
| 10,576,257 B2 | 3/2020 | Berry et al. |
| 10,596,333 B2 | 3/2020 | Howgill |
| 10,598,583 B1 * | 3/2020 | Peeters ............ A61B 5/150099 |
| 10,638,963 B2 | 5/2020 | Beyerlein et al. |
| 10,646,703 B2 | 5/2020 | Chowdhury |
| 10,653,349 B2 | 5/2020 | Delamarche et al. |
| 10,695,289 B2 | 6/2020 | Brown et al. |
| 10,695,547 B2 | 6/2020 | Burton et al. |
| 10,716,926 B2 | 7/2020 | Burton et al. |
| 10,729,842 B2 | 8/2020 | Hooven et al. |
| 10,772,550 B2 | 9/2020 | Aceti et al. |
| 10,779,757 B2 | 9/2020 | Berthier et al. |
| 10,799,166 B2 | 10/2020 | Gonzalez-Zugasti et al. |
| 10,835,163 B2 | 11/2020 | Haghgooie et al. |
| 10,881,342 B2 | 1/2021 | Kelly et al. |
| 10,888,259 B2 | 1/2021 | Jordan et al. |
| 10,926,030 B2 * | 2/2021 | Lanigan ................ H01Q 1/273 |
| 10,932,710 B2 | 3/2021 | Jordan et al. |
| 10,939,860 B2 | 3/2021 | Levinson et al. |
| 10,940,085 B2 | 3/2021 | Baker et al. |
| 10,953,211 B2 | 3/2021 | Ross et al. |
| 11,020,548 B2 | 6/2021 | Stuart et al. |
| 11,033,212 B2 | 6/2021 | Berthier et al. |
| 11,040,183 B2 | 6/2021 | Baker et al. |
| 11,103,685 B2 | 8/2021 | Gonzalez et al. |
| 11,110,234 B2 | 9/2021 | Richardson et al. |
| 11,116,953 B2 | 9/2021 | Kobayashi et al. |
| 11,147,955 B2 | 10/2021 | Gross et al. |
| 11,177,029 B2 | 11/2021 | Levinson et al. |
| 11,197,625 B1 | 12/2021 | Schleicher et al. |
| 11,202,895 B2 | 12/2021 | Davis et al. |
| 11,207,477 B2 | 12/2021 | Hodson |
| 11,247,033 B2 | 2/2022 | Baker et al. |
| 11,253,179 B2 | 2/2022 | Bernstein et al. |
| 11,266,337 B2 | 3/2022 | Jackson et al. |
| 11,273,272 B2 | 3/2022 | Stuart et al. |
| 11,291,989 B2 | 4/2022 | Morrison |
| 11,298,060 B2 | 4/2022 | Jordan et al. |
| 11,298,478 B2 | 4/2022 | Stuart et al. |
| 11,304,632 B2 | 4/2022 | Mou et al. |
| 11,344,684 B2 | 5/2022 | Richardson et al. |
| 11,395,614 B2 | 7/2022 | Berthier et al. |
| 11,452,474 B1 | 9/2022 | Nawana et al. |
| 11,458,289 B2 | 10/2022 | Moeckly et al. |
| 11,497,712 B2 | 11/2022 | Stein et al. |
| 11,497,866 B2 | 11/2022 | Howgill |
| 11,510,602 B1 | 11/2022 | Nawana et al. |
| 2002/0077584 A1 * | 6/2002 | Lin ................ A61B 5/150984 604/21 |
| 2002/0193740 A1 | 12/2002 | Alchas et al. |
| 2004/0002121 A1 * | 1/2004 | Regan ............ A61B 5/150343 435/7.2 |
| 2004/0010207 A1 | 1/2004 | Flaherty et al. |
| 2004/0059256 A1 * | 3/2004 | Perez ................ A61B 5/15113 600/583 |
| 2004/0059366 A1 * | 3/2004 | Sato ................ A61B 5/150068 606/182 |
| 2004/0106904 A1 | 6/2004 | Gonnelli et al. |
| 2004/0162467 A1 * | 8/2004 | Cook ............ A61B 5/150351 600/309 |
| 2005/0106713 A1 | 5/2005 | Phan et al. |
| 2005/0118388 A1 | 6/2005 | Kingsford |
| 2006/0047243 A1 | 3/2006 | Rosenberg |
| 2006/0068490 A1 | 3/2006 | Tang et al. |
| 2006/0142651 A1 | 6/2006 | Brister et al. |
| 2007/0004989 A1 | 1/2007 | Dhillon |
| 2007/0191696 A1 * | 8/2007 | Mischler ............ G01N 21/552 600/347 |
| 2008/0003274 A1 | 1/2008 | Kaiser |
| 2008/0287864 A1 | 11/2008 | Rosenberg |
| 2009/0012472 A1 | 1/2009 | Ahm et al. |
| 2009/0036826 A1 | 2/2009 | Sage, Jr. et al. |
| 2009/0099427 A1 | 4/2009 | Jina et al. |
| 2009/0105614 A1 | 4/2009 | Momose et al. |
| 2009/0112125 A1 | 4/2009 | Tamir |
| 2009/0198215 A1 * | 8/2009 | Chong ................ A61M 5/1413 604/506 |
| 2009/0259176 A1 | 10/2009 | Yairi |
| 2010/0198107 A1 * | 8/2010 | Groll ................ A61B 5/150175 600/583 |
| 2010/0249560 A1 | 9/2010 | Levinson et al. |
| 2010/0256524 A1 | 10/2010 | Levinson et al. |
| 2010/0269837 A1 | 10/2010 | Levinson et al. |
| 2010/0272652 A1 | 10/2010 | Levinson |
| 2011/0009847 A1 | 1/2011 | Levinson et al. |
| 2011/0060280 A1 | 3/2011 | Caffey et al. |
| 2011/0105872 A1 | 5/2011 | Chickering et al. |
| 2011/0105951 A1 | 5/2011 | Bernstein et al. |
| 2011/0105952 A1 | 5/2011 | Bernstein et al. |
| 2011/0125058 A1 | 5/2011 | Levinson et al. |
| 2011/0144463 A1 * | 6/2011 | Pesach ............ A61B 5/150267 600/345 |
| 2011/0172508 A1 | 7/2011 | Chickering, III et al. |
| 2011/0172510 A1 | 7/2011 | Chickering, III et al. |
| 2011/0198221 A1 | 8/2011 | Angelescu |
| 2011/0213335 A1 | 9/2011 | Burton et al. |

(56) References Cited

U.S. PATENT DOCUMENTS

| | | | |
|---|---|---|---|
| 2011/0245635 A1* | 10/2011 | Fujiwara | A61B 5/15117 600/573 |
| 2011/0257497 A1 | 10/2011 | Tamada et al. | |
| 2011/0288389 A9 | 11/2011 | Levinson et al. | |
| 2012/0016308 A1* | 1/2012 | Schott | A61B 5/150984 604/173 |
| 2012/0041338 A1 | 2/2012 | Chickering et al. | |
| 2012/0046203 A1 | 2/2012 | Walsh et al. | |
| 2012/0078224 A1 | 3/2012 | Lerner et al. | |
| 2012/0109066 A1 | 5/2012 | Chase et al. | |
| 2012/0123297 A1* | 5/2012 | Brancazio | A61B 5/150022 600/576 |
| 2012/0259599 A1 | 10/2012 | Deck et al. | |
| 2012/0271123 A1 | 10/2012 | Castle et al. | |
| 2012/0271125 A1 | 10/2012 | Bernstein et al. | |
| 2012/0275955 A1* | 11/2012 | Haghgooie | A61B 5/150213 210/321.62 |
| 2012/0277629 A1* | 11/2012 | Bernstein | A61B 5/150022 600/578 |
| 2012/0277696 A1 | 11/2012 | Gonzalez-Zugasti et al. | |
| 2012/0277697 A1* | 11/2012 | Haghgooie | A61B 5/14514 604/327 |
| 2013/0018279 A1* | 1/2013 | Plante | A61B 5/150755 600/583 |
| 2013/0158468 A1* | 6/2013 | Bernstein | A61M 1/38 604/173 |
| 2013/0158482 A1 | 6/2013 | Davis et al. | |
| 2013/0211289 A1 | 8/2013 | Moga et al. | |
| 2013/0253446 A1 | 9/2013 | Duan et al. | |
| 2013/0269423 A1 | 10/2013 | Angelescu | |
| 2014/0066843 A1 | 3/2014 | Zhang et al. | |
| 2014/0109900 A1 | 4/2014 | Jinks | |
| 2014/0194854 A1 | 7/2014 | Tsals | |
| 2014/0305823 A1* | 10/2014 | Gelfand | A61B 5/150221 600/583 |
| 2014/0309555 A1* | 10/2014 | Gelfand | A61B 5/150748 600/583 |
| 2014/0309557 A1 | 10/2014 | Fletcher et al. | |
| 2014/0336616 A1 | 11/2014 | Edwards | |
| 2015/0057510 A1 | 2/2015 | Levinson et al. | |
| 2015/0057901 A1 | 2/2015 | Sundholm et al. | |
| 2015/0073385 A1 | 3/2015 | Lyon et al. | |
| 2015/0087944 A1 | 3/2015 | Levinson et al. | |
| 2015/0136122 A1 | 5/2015 | Stuart et al. | |
| 2015/0250959 A1 | 9/2015 | Stuart et al. | |
| 2015/0258272 A1 | 9/2015 | Sullivan et al. | |
| 2015/0278476 A1 | 10/2015 | Levinson et al. | |
| 2015/0352295 A1 | 12/2015 | Burton et al. | |
| 2016/0038068 A1 | 2/2016 | Chickering, III et al. | |
| 2016/0051981 A1 | 2/2016 | Berthier et al. | |
| 2016/0067468 A1 | 3/2016 | Chowdhury et al. | |
| 2016/0136365 A1 | 5/2016 | Stuart et al. | |
| 2016/0144100 A1 | 5/2016 | Gharib et al. | |
| 2016/0199581 A1 | 7/2016 | Cachemaille et al. | |
| 2016/0213295 A1* | 7/2016 | Matsunami | A61B 5/150732 |
| 2016/0256095 A1* | 9/2016 | Krasnow | A61B 5/150076 |
| 2016/0262676 A1 | 9/2016 | Haghgooie et al. | |
| 2016/0315123 A1 | 10/2016 | Kim et al. | |
| 2016/0324506 A1* | 11/2016 | Tariyal | A61B 5/150755 |
| 2016/0354589 A1 | 12/2016 | Kobayashi et al. | |
| 2016/0361006 A1* | 12/2016 | Bullington | B01L 3/0217 |
| 2017/0001192 A1 | 1/2017 | Kelly et al. | |
| 2017/0014822 A1 | 1/2017 | Ker | |
| 2017/0021067 A1* | 1/2017 | Todd | A61B 5/150099 |
| 2017/0021117 A1 | 1/2017 | Howgill | |
| 2017/0035337 A1* | 2/2017 | Wilkinson | A61B 5/150267 |
| 2017/0035975 A1 | 2/2017 | Myung et al. | |
| 2017/0043103 A1 | 2/2017 | Wotton et al. | |
| 2017/0059304 A1 | 3/2017 | Ma et al. | |
| 2017/0120022 A1 | 5/2017 | Chickering, III et al. | |
| 2017/0122846 A1* | 5/2017 | Holmes | G01N 33/491 |
| 2017/0127991 A1 | 5/2017 | Bernstein et al. | |
| 2017/0173288 A1 | 6/2017 | Stam et al. | |
| 2017/0197029 A1* | 7/2017 | Cindrich | A61M 5/16804 |
| 2017/0224912 A1* | 8/2017 | Yodfat | A61M 5/14248 |
| 2017/0231543 A1 | 8/2017 | Cunningham et al. | |
| 2017/0290977 A1 | 10/2017 | Schauderna et al. | |
| 2018/0001029 A1 | 1/2018 | Egeland et al. | |
| 2018/0008183 A1 | 1/2018 | Chickering, III et al. | |
| 2018/0008703 A1 | 1/2018 | Johnson | |
| 2018/0008808 A1 | 1/2018 | Chowdhury et al. | |
| 2018/0021559 A1 | 1/2018 | Xu et al. | |
| 2018/0078241 A1* | 3/2018 | Moga | A61B 5/150343 |
| 2018/0103884 A1* | 4/2018 | Delamarche | A61B 5/150221 |
| 2018/0126058 A1 | 5/2018 | Nakka David et al. | |
| 2018/0132515 A1 | 5/2018 | Lawrence et al. | |
| 2018/0132774 A1 | 5/2018 | Gonzalez-Zugasti et al. | |
| 2018/0242890 A1* | 8/2018 | Chickering, III | A61B 5/150221 |
| 2018/0243543 A1 | 8/2018 | Baek et al. | |
| 2018/0296148 A1* | 10/2018 | Gelfand | A61M 1/3406 |
| 2018/0344631 A1 | 12/2018 | Zhang et al. | |
| 2018/0369512 A1 | 12/2018 | Blatchford et al. | |
| 2019/0000365 A1* | 1/2019 | Beyerlein | A61B 5/150251 |
| 2019/0001076 A1 | 1/2019 | Solomon et al. | |
| 2019/0001081 A1 | 1/2019 | Guion et al. | |
| 2019/0001085 A1 | 1/2019 | Cottenden et al. | |
| 2019/0015584 A1 | 1/2019 | Meehan et al. | |
| 2019/0015827 A1 | 1/2019 | Berthier et al. | |
| 2019/0022339 A1 | 1/2019 | Richardson et al. | |
| 2019/0023473 A1 | 1/2019 | Schott | |
| 2019/0030260 A1 | 1/2019 | Wotton et al. | |
| 2019/0053740 A1 | 2/2019 | Bernstein et al. | |
| 2019/0054010 A1 | 2/2019 | Slowey et al. | |
| 2019/0142318 A1* | 5/2019 | Diebold | A61B 5/150022 600/575 |
| 2019/0159709 A1 | 5/2019 | Barone et al. | |
| 2019/0209820 A1 | 7/2019 | Chickering, III et al. | |
| 2019/0240470 A1 | 8/2019 | Frederickson et al. | |
| 2019/0298943 A1 | 10/2019 | Stuart et al. | |
| 2019/0336058 A1 | 11/2019 | Haghgooie et al. | |
| 2019/0366067 A1 | 12/2019 | Ginggen et al. | |
| 2020/0009364 A1 | 1/2020 | Amir | |
| 2020/0010219 A1 | 1/2020 | Felippone et al. | |
| 2020/0011860 A1 | 1/2020 | Nawana et al. | |
| 2020/0033008 A1 | 1/2020 | Baker | |
| 2020/0069897 A1 | 3/2020 | Hodson et al. | |
| 2020/0085414 A1* | 3/2020 | Berthier | A61B 5/15117 |
| 2020/0101219 A1 | 4/2020 | Wang et al. | |
| 2020/0147209 A1 | 5/2020 | Johnson | |
| 2020/0163603 A1 | 5/2020 | Jordan et al. | |
| 2020/0164359 A1 | 5/2020 | Jordan et al. | |
| 2020/0246560 A1 | 8/2020 | Hodson et al. | |
| 2020/0253521 A1* | 8/2020 | Ivosevic | A61B 5/150755 |
| 2020/0261668 A1 | 8/2020 | Hodson et al. | |
| 2020/0289808 A1 | 9/2020 | Moeckly et al. | |
| 2020/0297945 A1 | 9/2020 | Cottenden et al. | |
| 2020/0353155 A1 | 11/2020 | Bernstein et al. | |
| 2021/0022681 A1 | 1/2021 | Chickering, III et al. | |
| 2021/0030975 A1 | 2/2021 | Burton et al. | |
| 2021/0059588 A1 | 3/2021 | Welch et al. | |
| 2021/0100487 A1 | 4/2021 | Cho et al. | |
| 2021/0121110 A1 | 4/2021 | Kelly et al. | |
| 2021/0170153 A1 | 6/2021 | Ross et al. | |
| 2021/0196567 A1 | 7/2021 | Baker et al. | |
| 2021/0228124 A1 | 7/2021 | Gonzalez-Zugasti et al. | |
| 2021/0259599 A1 | 8/2021 | Haghgooie et al. | |
| 2021/0298679 A1 | 9/2021 | Pierart | |
| 2021/0330227 A1 | 10/2021 | Levinson et al. | |
| 2021/0369150 A1 | 12/2021 | Bernstein et al. | |
| 2021/0378567 A1* | 12/2021 | Weidemaier | A61B 5/150755 |
| 2022/0031211 A1* | 2/2022 | Yakhnich | A61B 5/150114 |
| 2022/0058895 A1 | 2/2022 | Han | |
| 2022/0062607 A1 | 3/2022 | Davis et al. | |
| 2022/0071534 A9 | 3/2022 | Gonzalez-Zugasti et al. | |
| 2022/0133192 A1 | 5/2022 | Brancazio | |
| 2022/0134072 A1 | 5/2022 | Kosel et al. | |
| 2022/0215921 A1 | 7/2022 | Levinson et al. | |
| 2022/0218251 A1 | 7/2022 | Jackson et al. | |
| 2022/0233117 A1 | 7/2022 | Lee et al. | |
| 2022/0249818 A1 | 8/2022 | Chickering, III et al. | |
| 2022/0257158 A1 | 8/2022 | Haghgooie et al. | |
| 2022/0287642 A1 | 9/2022 | Chickering, III et al. | |

(56) References Cited

U.S. PATENT DOCUMENTS

| | | | |
|---|---|---|---|
| 2022/0313128 A1 | 10/2022 | Bernstein et al. |
| 2022/0330860 A1 | 10/2022 | Nawana |
| 2022/0361784 A1 | 11/2022 | Jordan et al. |
| 2023/0109881 A1 | 4/2023 | Nawana et al. |

FOREIGN PATENT DOCUMENTS

| | | | |
|---|---|---|---|
| CN | 101296752 A | 10/2008 |
| EP | 0931507 A1 | 7/1999 |
| EP | 1769735 A1 | 4/2007 |
| EP | 2493537 A2 | 9/2012 |
| EP | 3513833 A1 | 7/2019 |
| EP | 3490453 B1 | 12/2021 |
| EP | 3962363 A1 | 3/2022 |
| ES | 2550668 T3 | 11/2015 |
| ES | 2565805 T3 | 4/2016 |
| GB | 1492500 A | 11/1977 |
| JP | 2004024164 A | 1/2004 |
| KR | 101857300 B1 | 5/2018 |
| WO | 9311747 A1 | 6/1993 |
| WO | 9929296 A1 | 6/1999 |
| WO | 0078286 A1 | 12/2000 |
| WO | 0210037 A1 | 2/2002 |
| WO | 0226217 A2 | 4/2002 |
| WO | 0232785 A1 | 4/2002 |
| WO | 02083205 A1 | 10/2002 |
| WO | 02083231 A1 | 10/2002 |
| WO | 02083232 A1 | 10/2002 |
| WO | 03002069 A2 | 1/2003 |
| WO | 03030880 A1 | 4/2003 |
| WO | 03035510 A1 | 5/2003 |
| WO | 03066126 A2 | 8/2003 |
| WO | 03084597 A1 | 10/2003 |
| WO | 03086349 A1 | 10/2003 |
| WO | 03086350 A1 | 10/2003 |
| WO | 03089036 A1 | 10/2003 |
| WO | 2004009172 A1 | 1/2004 |
| WO | 2004022133 A2 | 3/2004 |
| WO | 2004022142 A1 | 3/2004 |
| WO | 2004032990 A2 | 4/2004 |
| WO | 2004039429 A2 | 5/2004 |
| WO | 2004062715 A3 | 10/2004 |
| WO | 2004098576 A1 | 11/2004 |
| WO | 2005006535 A1 | 1/2005 |
| WO | 2005026236 A1 | 3/2005 |
| WO | 2005060441 A2 | 7/2005 |
| WO | 2005014078 A3 | 10/2005 |
| WO | 2005084534 | 10/2005 |
| WO | 2005123173 A1 | 12/2005 |
| WO | 2006016364 A2 | 2/2006 |
| WO | 2006055795 A1 | 5/2006 |
| WO | 2006055799 A1 | 5/2006 |
| WO | 2006055802 A1 | 5/2006 |
| WO | 2006055844 A2 | 5/2006 |
| WO | 2006062848 A1 | 6/2006 |
| WO | 2006062974 A2 | 6/2006 |
| WO | 2006108185 A1 | 10/2006 |
| WO | 2006115663 A2 | 11/2006 |
| WO | 2006135696 A2 | 12/2006 |
| WO | 2007002521 A2 | 1/2007 |
| WO | 2007002522 A1 | 1/2007 |
| WO | 2007002523 A2 | 1/2007 |
| WO | 2007023276 A1 | 3/2007 |
| WO | 2007061781 A1 | 5/2007 |
| WO | 2007064486 A1 | 6/2007 |
| WO | 2007103712 A2 | 9/2007 |
| WO | 2006110723 A3 | 11/2007 |
| WO | 2007124411 A1 | 11/2007 |
| WO | 2008014161 A1 | 1/2008 |
| WO | 2007124406 A3 | 2/2008 |
| WO | 2008008845 A3 | 4/2008 |
| WO | 2008049107 A1 | 4/2008 |
| WO | 2008091602 A3 | 9/2008 |
| WO | 2008121459 A1 | 10/2008 |
| WO | 2008149333 A9 | 1/2009 |
| WO | 2009037192 A1 | 3/2009 |
| WO | 2009046173 A3 | 5/2009 |
| WO | 2009061895 A2 | 5/2009 |
| WO | 2009061907 A2 | 5/2009 |
| WO | 2009056981 A3 | 8/2009 |
| WO | 2009126653 A1 | 10/2009 |
| WO | 2009158300 A1 | 12/2009 |
| WO | 2009142852 A3 | 1/2010 |
| WO | 2010049048 A1 | 5/2010 |
| WO | 2010059605 A2 | 5/2010 |
| WO | 2010062908 A1 | 6/2010 |
| WO | 2010071262 A1 | 6/2010 |
| WO | 2010098339 A1 | 9/2010 |
| WO | 2010101621 A1 | 9/2010 |
| WO | 2010101625 A2 | 9/2010 |
| WO | 2010101626 A1 | 9/2010 |
| WO | 2010101620 A3 | 11/2010 |
| WO | 2010129783 A1 | 11/2010 |
| WO | 2010002613 A3 | 12/2010 |
| WO | 2010110916 A3 | 12/2010 |
| WO | 2010151329 A1 | 12/2010 |
| WO | 2010117602 A3 | 3/2011 |
| WO | 2011016615 A3 | 4/2011 |
| WO | 2011053787 A2 | 5/2011 |
| WO | 2011053788 A1 | 5/2011 |
| WO | 2011053796 A2 | 5/2011 |
| WO | 2011063067 A1 | 5/2011 |
| WO | 2011065972 A2 | 6/2011 |
| WO | 2011071788 A1 | 6/2011 |
| WO | 2011075099 A1 | 6/2011 |
| WO | 2011075103 A1 | 6/2011 |
| WO | 2011075104 A1 | 6/2011 |
| WO | 2011075105 A1 | 6/2011 |
| WO | 2011075569 A1 | 6/2011 |
| WO | 2011084316 A2 | 7/2011 |
| WO | 2011088211 A2 | 7/2011 |
| WO | 2011094573 A1 | 8/2011 |
| WO | 2011014514 | 9/2011 |
| WO | 2011088214 A3 | 9/2011 |
| WO | 2011113114 A1 | 9/2011 |
| WO | 2011116388 A1 | 9/2011 |
| WO | 2011084951 A3 | 11/2011 |
| WO | 2011088211 A3 | 12/2011 |
| WO | 2011150144 A2 | 12/2011 |
| WO | 2011163347 A2 | 12/2011 |
| WO | 2012030316 A1 | 3/2012 |
| WO | 2012018486 A3 | 4/2012 |
| WO | 2012045561 A1 | 4/2012 |
| WO | 2012048388 A1 | 4/2012 |
| WO | 2012049155 A1 | 4/2012 |
| WO | 2012054592 A1 | 4/2012 |
| WO | 2012021792 A3 | 5/2012 |
| WO | 2012028675 A3 | 5/2012 |
| WO | 2012061556 A1 | 5/2012 |
| WO | 2012089627 A1 | 7/2012 |
| WO | 2012122162 A1 | 9/2012 |
| WO | 2012145665 A2 | 10/2012 |
| WO | 2012117302 A3 | 11/2012 |
| WO | 2012149126 A1 | 11/2012 |
| WO | 2012149143 A1 | 11/2012 |
| WO | 2012154362 | 12/2012 |
| WO | 2012173971 A1 | 12/2012 |
| WO | 2012149134 | 1/2013 |
| WO | 2012149155 A9 | 3/2013 |
| WO | 2013036602 A1 | 3/2013 |
| WO | 2013050701 A1 | 4/2013 |
| WO | 2013055638 A1 | 4/2013 |
| WO | 2013055641 A1 | 4/2013 |
| WO | 2013059409 A1 | 4/2013 |
| WO | 2013082418 A1 | 6/2013 |
| WO | 2013082427 A1 | 6/2013 |
| WO | 2013090353 A1 | 6/2013 |
| WO | 2013096026 A1 | 6/2013 |
| WO | 2013096027 A1 | 6/2013 |
| WO | 2013112877 A1 | 8/2013 |
| WO | 2013120665 A1 | 8/2013 |
| WO | 2013136176 A1 | 9/2013 |
| WO | 2013136185 A3 | 11/2013 |
| WO | 2013165715 A1 | 11/2013 |

(56) References Cited

FOREIGN PATENT DOCUMENTS

| | | |
|---|---|---|
| WO | 2013188609 A1 | 12/2013 |
| WO | 2014004462 A1 | 1/2014 |
| WO | 2014018558 A1 | 1/2014 |
| WO | 2014039367 A1 | 3/2014 |
| WO | 2014052263 A1 | 4/2014 |
| WO | 2014058746 A1 | 4/2014 |
| WO | 2014059104 A1 | 4/2014 |
| WO | 2014078545 A1 | 5/2014 |
| WO | 2014081746 A1 | 5/2014 |
| WO | 2014099404 A1 | 6/2014 |
| WO | 2014105458 A1 | 7/2014 |
| WO | 2014110016 A1 | 7/2014 |
| WO | 2014096001 A3 | 8/2014 |
| WO | 2014132239 A1 | 9/2014 |
| WO | 2014132240 A1 | 9/2014 |
| WO | 2014153447 A2 | 9/2014 |
| WO | 2014160804 A2 | 10/2014 |
| WO | 2014172246 A1 | 10/2014 |
| WO | 2014172247 A1 | 10/2014 |
| WO | 2014193725 A1 | 12/2014 |
| WO | 2014193727 A1 | 12/2014 |
| WO | 2014193729 A1 | 12/2014 |
| WO | 2014204951 A1 | 12/2014 |
| WO | 2014186263 A3 | 1/2015 |
| WO | 2015006292 A1 | 1/2015 |
| WO | 2015009523 A1 | 1/2015 |
| WO | 2015009530 A1 | 1/2015 |
| WO | 2015009531 A1 | 1/2015 |
| WO | 2015031552 A1 | 3/2015 |
| WO | 2015034709 A1 | 3/2015 |
| WO | 2015038556 A1 | 3/2015 |
| WO | 2015023649 A3 | 4/2015 |
| WO | 2015072924 A1 | 5/2015 |
| WO | 2015116625 A1 | 8/2015 |
| WO | 2015153570 A1 | 10/2015 |
| WO | 2015153624 A1 | 10/2015 |
| WO | 2015168210 A1 | 11/2015 |
| WO | 2015168215 A1 | 11/2015 |
| WO | 2015168217 A1 | 11/2015 |
| WO | 2015179511 A1 | 11/2015 |
| WO | 2016009986 A1 | 1/2016 |
| WO | 2016018892 A1 | 2/2016 |
| WO | 2016081843 A1 | 5/2016 |
| WO | 2016099986 A2 | 6/2016 |
| WO | 2016100708 A1 | 6/2016 |
| WO | 2016109336 A1 | 7/2016 |
| WO | 2016109339 A1 | 7/2016 |
| WO | 2016109342 A1 | 7/2016 |
| WO | 2016118459 A1 | 7/2016 |
| WO | 2016122915 A1 | 8/2016 |
| WO | 2016132368 A1 | 8/2016 |
| WO | 2016137853 A1 | 9/2016 |
| WO | 2016164508 A1 | 10/2016 |
| WO | 2015168219 | 12/2016 |
| WO | 2017024115 A1 | 2/2017 |
| WO | 2017044887 A1 | 3/2017 |
| WO | 2017062727 A1 | 4/2017 |
| WO | 2017062922 A1 | 4/2017 |
| WO | 2017075018 A1 | 5/2017 |
| WO | 2017075586 A1 | 5/2017 |
| WO | 2017087355 A1 | 5/2017 |
| WO | 2017087368 A1 | 5/2017 |
| WO | 2017112400 A1 | 6/2017 |
| WO | 2017112451 A1 | 6/2017 |
| WO | 2017112452 A1 | 6/2017 |
| WO | 2017112748 A1 | 6/2017 |
| WO | 2017113011 A1 | 7/2017 |
| WO | 2017139084 A1 | 8/2017 |
| WO | 2017112476 A3 | 9/2017 |
| WO | 2017176693 A1 | 10/2017 |
| WO | 2017176704 A1 | 10/2017 |
| WO | 2017193076 A1 | 11/2017 |
| WO | 2018022535 A1 | 2/2018 |
| WO | 2018048786 A1 | 3/2018 |
| WO | 2018048790 A1 | 3/2018 |
| WO | 2018048795 A1 | 3/2018 |
| WO | 2018048797 A1 | 3/2018 |
| WO | 2018057760 A1 | 3/2018 |
| WO | 2018128976 A1 | 7/2018 |
| WO | 2018132515 A1 | 7/2018 |
| WO | 2018204217 A1 | 11/2018 |
| WO | 2018213244 A1 | 11/2018 |
| WO | 2019067567 A1 | 4/2019 |
| WO | 2019121324 A1 | 6/2019 |
| WO | 2020025823 A1 | 2/2020 |
| WO | 2020102281 A1 | 5/2020 |
| WO | 2020223710 A1 | 11/2020 |
| WO | 2021007344 A1 | 1/2021 |
| WO | 2021041881 A1 | 3/2021 |
| WO | 2021076846 A1 | 4/2021 |
| WO | 2021121638 A1 | 6/2021 |
| WO | 2021198768 A2 | 10/2021 |
| WO | 2021222066 A1 | 11/2021 |
| WO | 2021222805 A1 | 11/2021 |
| WO | 2022064055 A1 | 3/2022 |

OTHER PUBLICATIONS

International Search Report and Written Opinion for PCT/US2022/046384 mailed Jan. 5, 2023.
International Search Report and Written Opinion for PCT/US2022/048913 mailed Feb. 21, 2023.
International Search Report and Written Opinion for PCT/US22/029829 mailed Nov. 23, 2022.
International Search Report and Written Opinion, PCT/US2022/029829, dated Nov. 23, 2022, 16 pages.
International Search Report and Written Opinion, PCT/US2022/046384, dated Jan. 5, 2023, 12 pages.
International Search Report and Written Opinion, PCT/US2022/048913, dated Feb. 21, 2023, 16 pages.
International Search Report and Written Opinion, PCT/US2022/024607, dated Aug. 4, 2022, 17 pages.
Taiwan Office Action, TW111142334, dated May 18, 2023, 29 pages.
International Preliminary Report of Patentability, PCT/US2022/029829, Nov. 21, 2023.
International Preliminary Report on Patentability for International Application No. PCT/US2022/024607 dated Oct. 12, 2023.
International Search Report and Written Opinion for International Application No. PCT/US2023/080656 dated Feb. 29, 2024.
Taiwan Office Action, TW111142334, issued Dec. 12, 2023, 3 pages.
Written Opinion for International Application No. PCT/US2022/024607 issued Oct. 12, 2023.

\* cited by examiner

DERMAL PATCH FOR COLLECTING A PHYSIOLOGICAL SAMPLE

RELATED APPLICATIONS

The present application is a continuation-in-part of U.S. application Ser. No. 17/521,466, filed on Nov. 8, 2021, which is incorporated by reference herein in its entirety.

TECHNICAL FIELD

The present teachings are generally directed to dermal patches that can be employed to collect a physiological sample from a subject.

BACKGROUND

Biomarkers are increasingly employed for diagnosis of various disease conditions as well as for assessing treatment protocols. In many cases, it is important to monitor the level of a biomarker over time (e.g., to assess the progression of a disease). The temporal monitoring of biomarkers via conventional techniques includes drawing a physiological fluid sample from a subject. These techniques may be cumbersome and painful to the subject. For example, the invasive nature of drawing a blood sample from a subject can cause discomfort and may lead to less cooperation from a subject, especially children, rendering multiple measurements of a target analyte difficult.

Some recently developed devices allow for continuous monitoring of a target analyte (e.g., glucose monitors). Unfortunately, these devices typically suffer from several shortcomings, such as low sensitivity and/or specificity. Therefore, there is still a need for dermal patches that allow collection of a physiological sample (e.g., a blood sample) for monitoring a target analyte.

SUMMARY

Aspects of the present disclosure address the above-referenced problems and/or others.

In one aspect, a device for collecting a physiological sample from a subject includes a lancet having at least one needle configured for puncturing the subject's skin and a cartridge configured for engaging with the lancet. The lancet is configured to transition from an undeployed position to a deployed position in response to engagement with the cartridge, thereby allowing the needle to puncture the subject's skin. In some embodiments, the device further includes a specimen collection pad disposed within the cartridge, and wherein the cartridge further includes a chamber, a vacuum channel in open communication with the chamber, a physiological sample well, a physiological sample channel in open communication with the vacuum channel and the physiological sample well. In certain embodiments, the specimen collection pad is removable. In some embodiments the device further includes an adhesive layer affixed to the cartridge and the specimen collection pad is attached to the adhesive layer.

In some embodiments, the device further includes a lancet aperture in open communication with the physiological sample well. In these embodiments, the lancet aperture and the physiological sample well are configured to allow a needle of a lancet to extend therethrough to puncture the skin of a subject when the dermal patch is affixed to the subject's skin. In certain embodiments, the device includes a vacuum pin disposed within the vacuum chamber and the vacuum pin is configured to create a vacuum within the cartridge. In certain embodiments, at least a portion of the specimen collection channel is three sided. In some embodiments, at least a portion of the vacuum channel is three sided. In certain embodiments, the device further includes a specimen collection pad housing, and the specimen collection pad is disposed within the specimen collection pad housing. In some embodiments, the cover and the specimen collection pad housing each include a viewing aperture that provide visual access to the specimen collection pad disposed within the specimen collection pad.

In another aspect, a method for obtaining a physiological sample includes attaching a dermal patch onto the skin of a subject and coupling a lancet with a needle to the dermal patch. Coupling the lancet to the dermal patch causes the needle to automatically draw the physiological sample. In some embodiments, coupling the lancet to the dermal patch causes the needle to automatically pierce the skin of the subject and subsequently automatically retract into the lancet. In certain embodiments, the method further includes collecting the drawn physiological sample on a physiological sample collection pad that is disposed within the dermal patch. In some embodiments, the method also includes removing physiological sample collection pad from the dermal patch. In certain embodiments, the method also includes after drawing the physiological sample, moving a vacuum pin of the dermal patch from a deployed to a deployed position, wherein moving the vacuum pin from the undeployed position to the deployed position causes the drawn physiological sample to travel to the physiological sample collection pad. In some embodiments, moving the vacuum pin from the undeployed position to the deployed position creates a vacuum within the dermal patch that causes the drawn physiological sample to travel to the physiological sample collection pad.

In yet another aspect, a lancet for use with a cartridge of a dermal patch system, includes a housing configured for engagement with the cartridge, a needle disposed within the housing, and a mechanism configured to retain the needle within the housing in absence of engagement of the lancet with the housing and to deploy the needle for puncturing the skin when the lancet is engaged with the cartridge. In some embodiments, the mechanism is further configured to automatically retract the needle. In certain embodiments, the lancet further includes an injection spring configured to move the needle to the deployed position. In some embodiments, the lancet also includes a retraction spring configured to move the needle to a retracted position. In certain embodiments, the lancet also includes a sleeve disposed within the housing and the sleeve retains the needle in in the undeployed position when the lancet is not coupled to the dermal patch.

BRIEF DESCRIPTION OF THE DRAWINGS

Aspects of the present disclosure may take form in various components and arrangements of components, and in various steps and arrangements of steps. The drawings are only for illustration purpose of preferred embodiments of the present disclosure and are not to be considered as limiting.

Features of embodiments of the present disclosure will be more readily understood from the following detailed description take in conjunction with the accompanying drawings in which.

DETAILED DESCRIPTION

Figure 1:
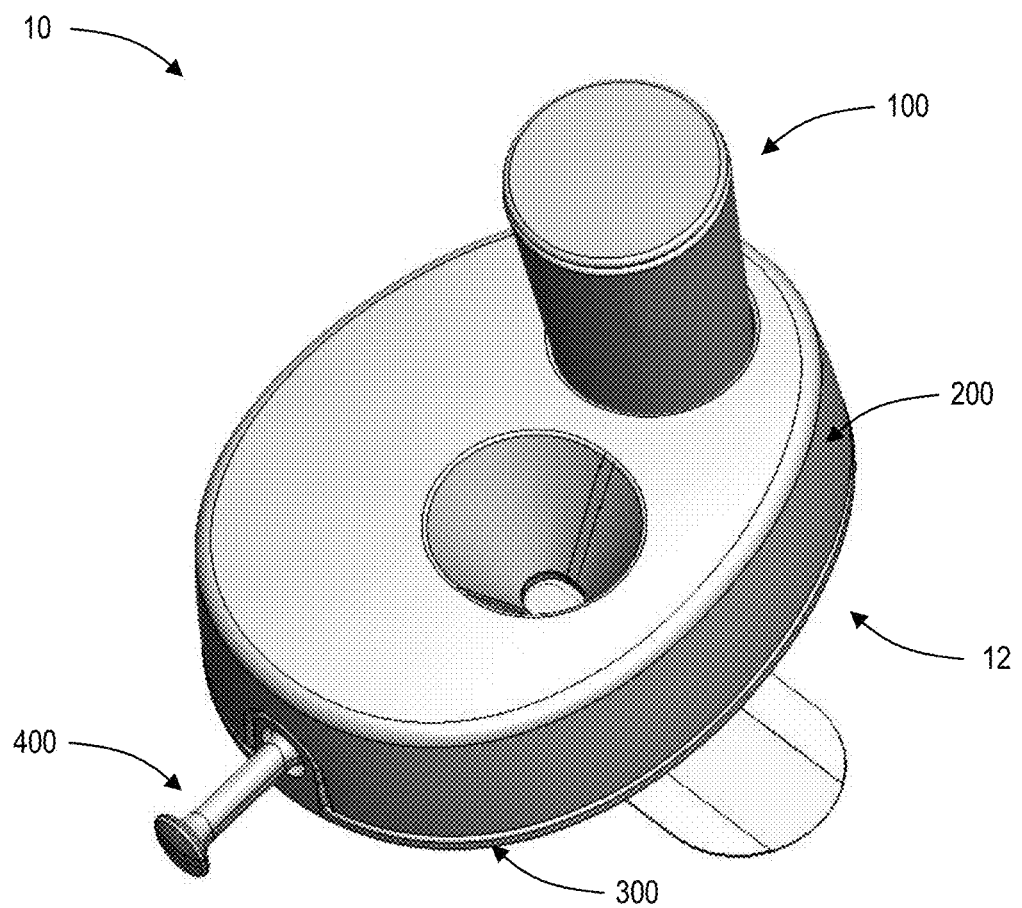
FIG. 1 depicts a dermal patch system in accordance with an exemplary embodiment of the present disclosure.

The present disclosure generally relates to a dermal patch that may be utilized to collect and/or store a collected physiological sample.

In some embodiments, a dermal patch may be used to collect a physiological sample and the collected sample may then be stored on a sample collection pad of the dermal patch. Dermal patches disclosed herein may allow for the collection and analysis of a physiological sample in a variety of environments (e.g., in the home, in the field, in a medical facility, etc.).

Various terms are used herein in accordance with their ordinary meanings in the art, unless otherwise indicated.

The term "about," as used herein, denotes a deviation of at most 10% relative to a numerical value. For example, about 100 μm means in the range of 90 μm-110 μm.

The term "substantially," as used herein, refers to a deviation, if any, of at most 10% from a complete state and/or condition.

The term "subject" as used herein refers to a human subject or an animal subject (e.g., chicken, pig, cattle, dog, cat, etc.).

The term "physiological sample," as used herein, includes fluid drawn from a subject and includes, but is not limited to, blood and interstitial fluid.

The term "lancet," as used herein refers broadly to an element that can be used to provide a passageway, or facilitate the production of a passageway, in the skin for the collection of a physiological sample.

The term "transparent," as used herein, indicates that light can substantially pass through an object (e.g., a window) to allow visualization of a material disposed behind the object. For example, in some embodiments, a transparent object allows the passageway of at least 70%, or at least 80%, or at least 90% of visible light therethrough.

The term "vacuum," as used herein, refers to a pressure less than atmospheric pressure and more particularly to a pressure that can facilitate the movement of a fluid (e.g., a physiological sample) within a dermal patch.

The term "needle" as used herein, refers to a component with a pointed tip that is configured to pierce the skin of a subject.

The present disclosure generally relates to a device, which is herein also referred to as a dermal patch or a dermal patch system, for collecting a physiological sample (e.g., bodily fluids such as blood, interstitial fluids, etc.) from a subject. In some embodiments discussed below, such a dermal patch system can include a cartridge that can be affixed to a subject's skin (e.g., via an adhesive layer) and a separate lancet that can be engaged with the cartridge to puncture the skin, thereby providing a passageway for extracting the physiological sample. As discussed in more detail below, the lancet can include a housing in which at least one needle that is configured for puncturing the skin is disposed. The lancet can further include a mechanism that can be transitioned between at least two states. In one state (herein referred to as a locked state), the mechanism retains the needle within the lancet in an undeployed position when the lancet is not engaged with the cartridge. When the lancet is coupled to the cartridge, the mechanism transitions to a second state (herein referred to as a released state). In the released state, the mechanism allows the needle to be deployed for puncturing the skin. For example, in some embodiments, the mechanism can include an upper locking portion that can retain an upper spring that is coupled to a needle platform (to which a needle is mounted) in a compressed state, thereby preventing the needle from transitioning into a deployed position. Further, the mechanism can include an upper interference member that prevents the movement of the needle platform when the mechanism is in the locked state.

The engagement of the lancet with the cartridge results in an automatic transition of the mechanism from the locking state to the released state, which in turns transitions the needle into a deployed position in which the needle extends beyond the lancet and the cartridge housing to puncture the subject's skin. In some embodiments, the engagement of the lancet with the cartridge causes the upper locking member to release the needle platform, which in turn allows the upper spring to decompress and thus push down the needle platform thereby deploying the needle. In some embodiments, the mechanism can further include a lower interference member that restricts the downward movement of the needle platform, when the needle platform is released. In this manner the extent of the penetration of the needle into the skin can be controlled. In certain embodiments, the mechanism can also include a lower locking member that retains a lower spring in a compressed state. The downward movement of the needle platform can cause the release of the lower locking member to allow the lower spring to decompress and exert a force on the needle platform to cause the retraction of the needle into the lancet housing.

In this manner, the lancet remains safe before it is engaged with the cartridge as the lancet is not capable of deploying the needle when the lancet is not engaged with the cartridge. Furthermore, in this manner, the lancet remains safe after drawing a physiological sample as the needle automatically retracts back into the lancet after being deployed.

Figure 10:
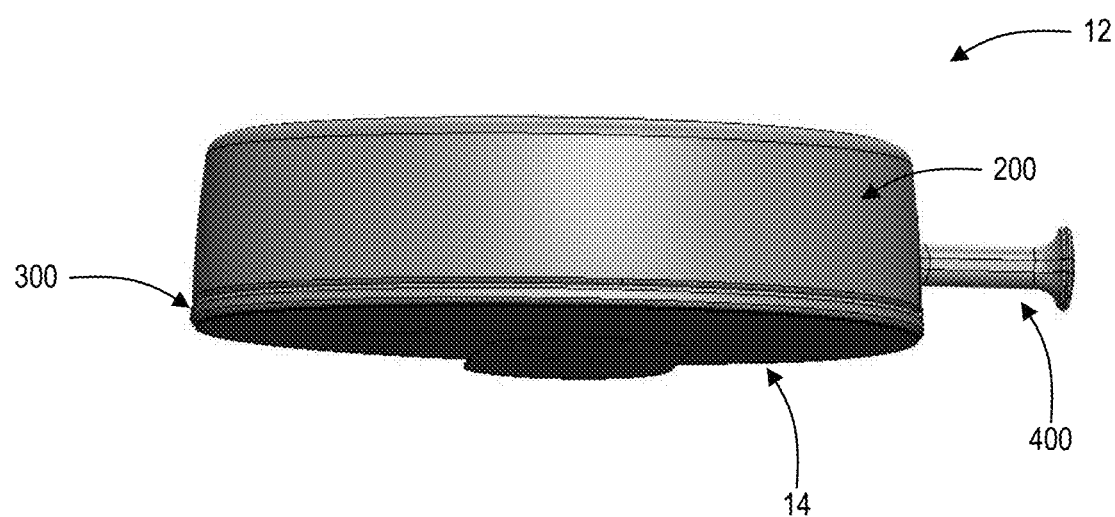
FIG. 10 depicts a cartridge of the dermal patch system in accordance with an exemplary embodiment of the present disclosure.
Figure 11:
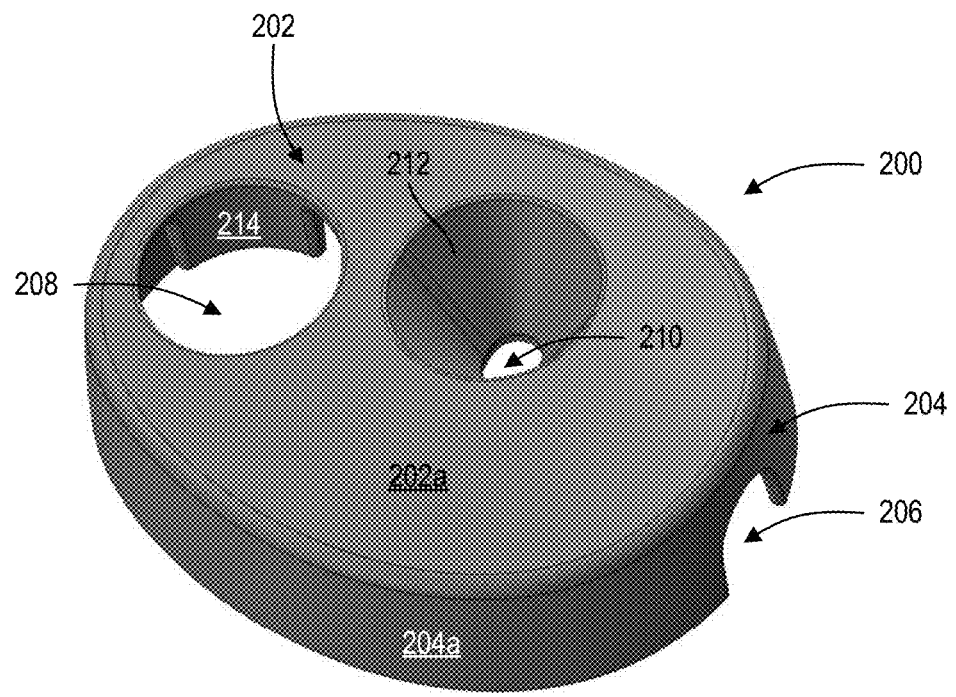
FIGS. 11-16 depict a cover of the cartridge in accordance with an exemplary embodiment of the present disclosure.
Figure 12:
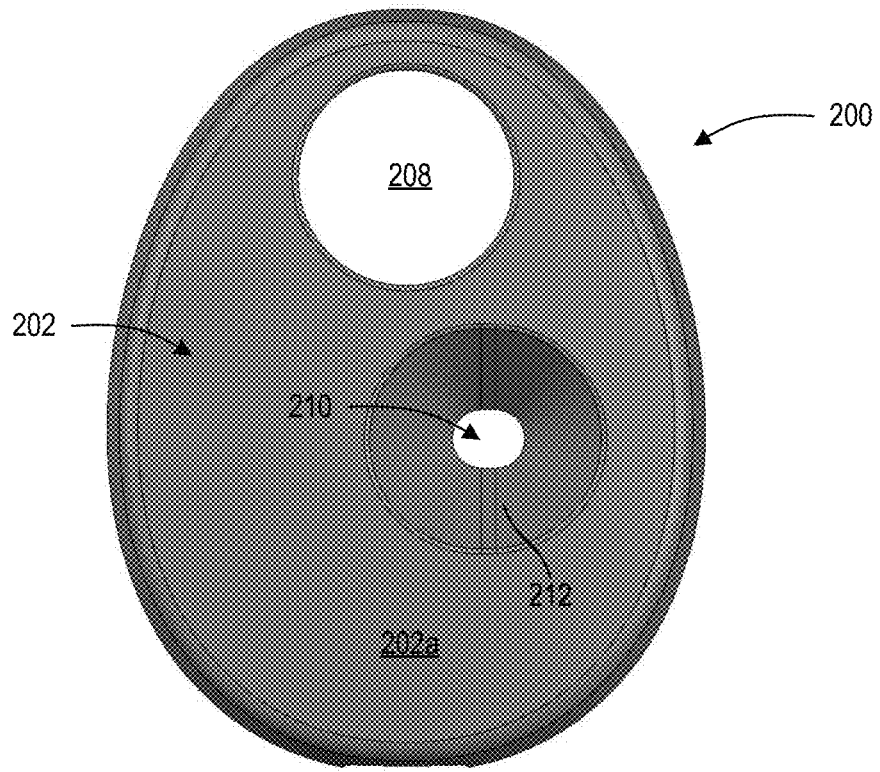
Figure 13:
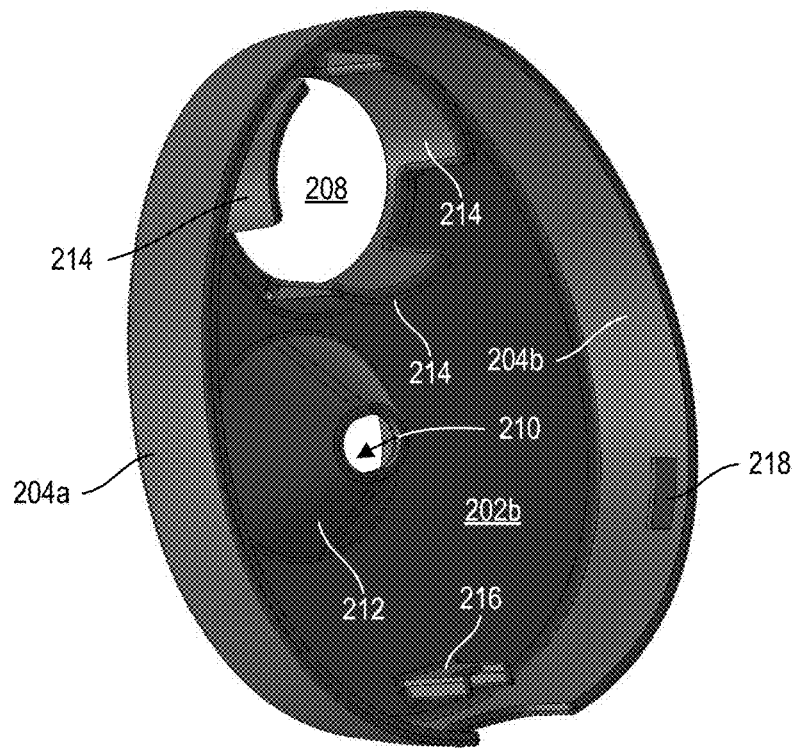
Figure 14:
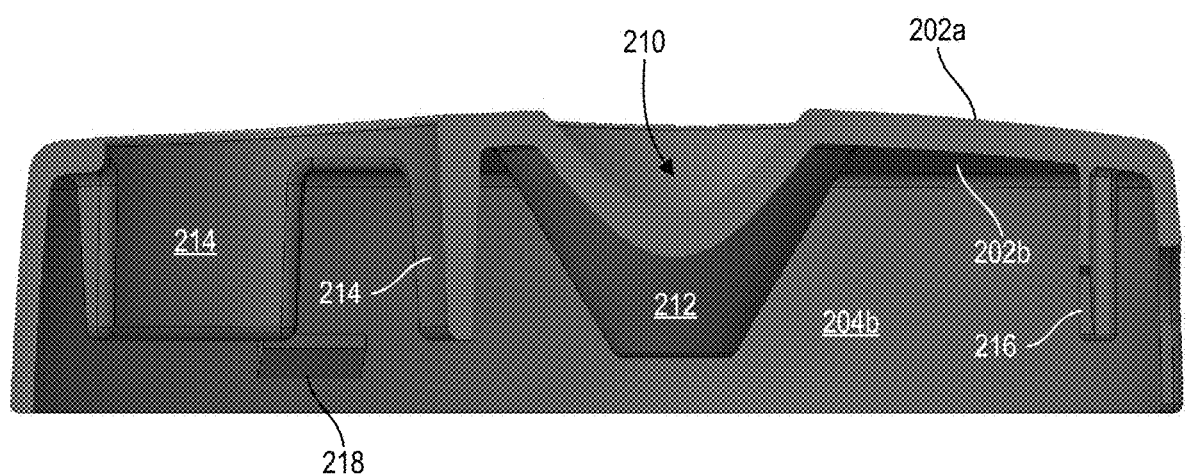
Figure 15:
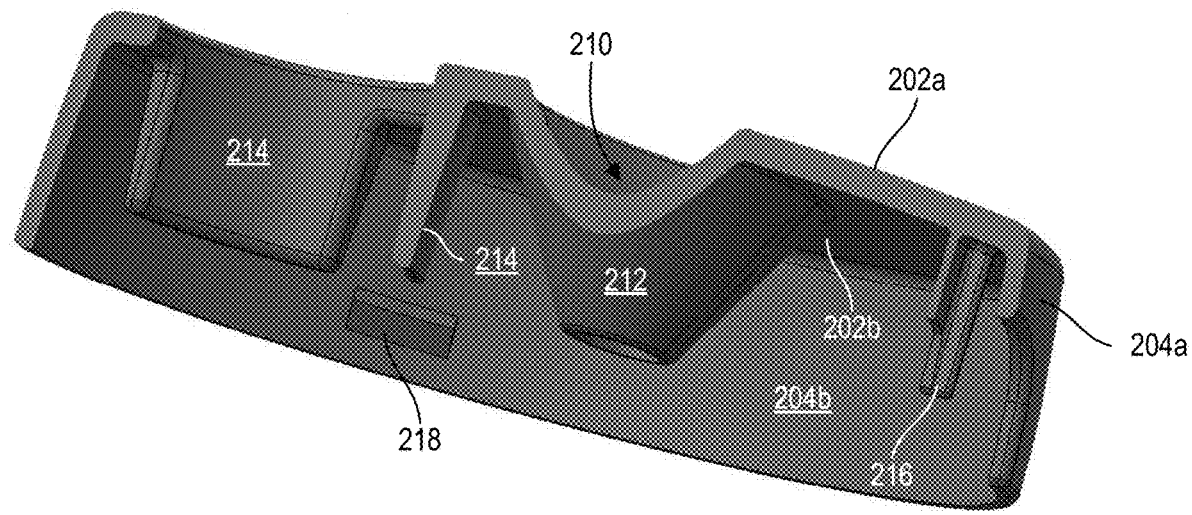
Figure 16:
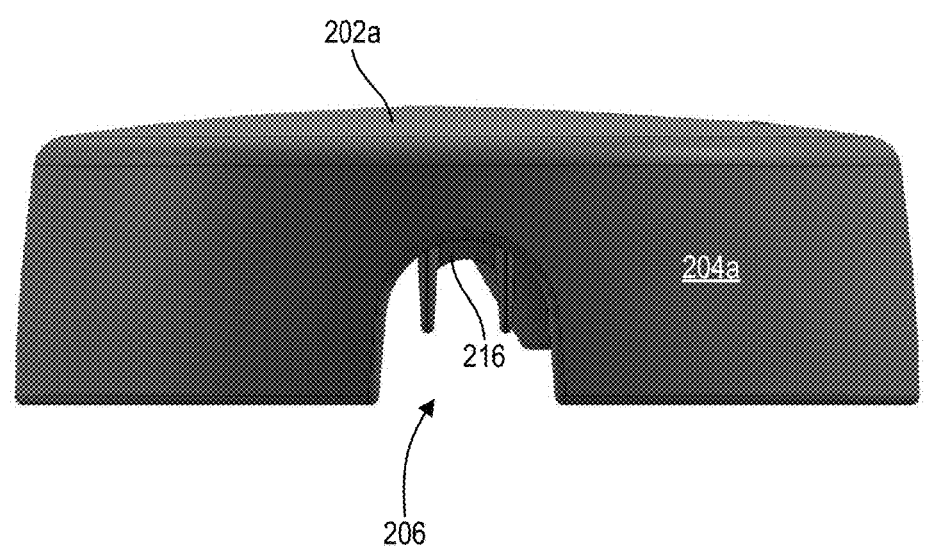
Figure 17:
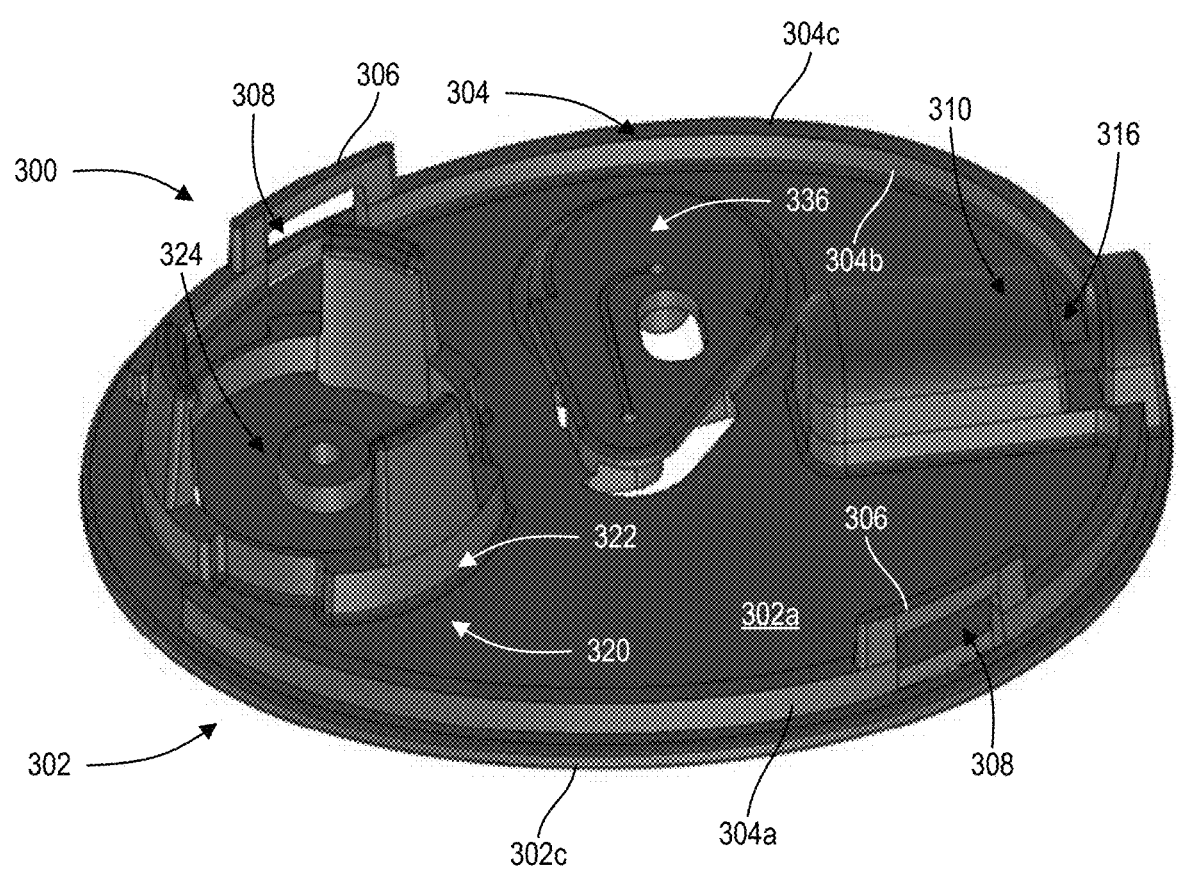
FIGS. 17-19 depict a base of the cartridge in accordance with an exemplary embodiment of the present disclosure.
Figure 18:
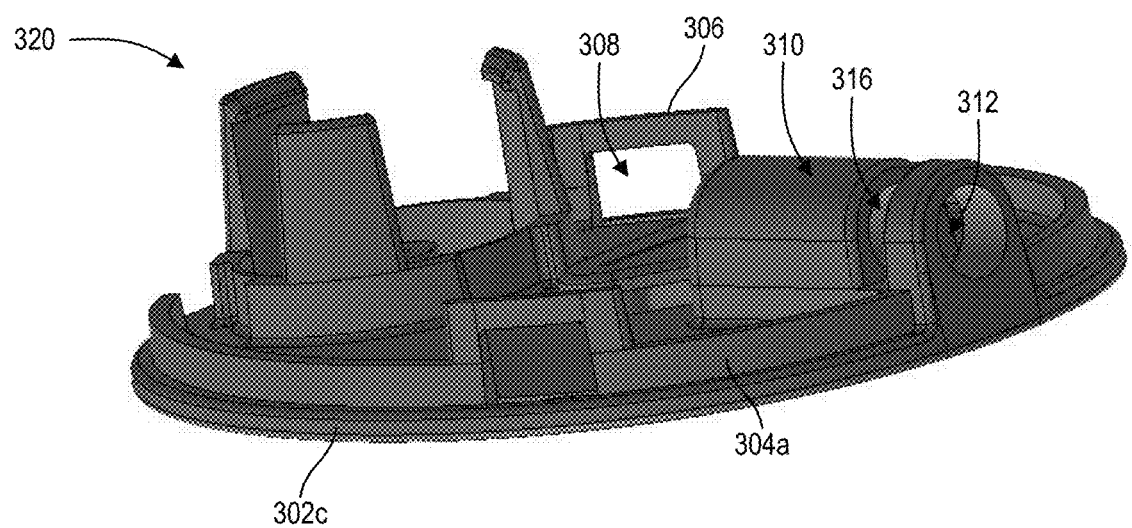
Figure 19:
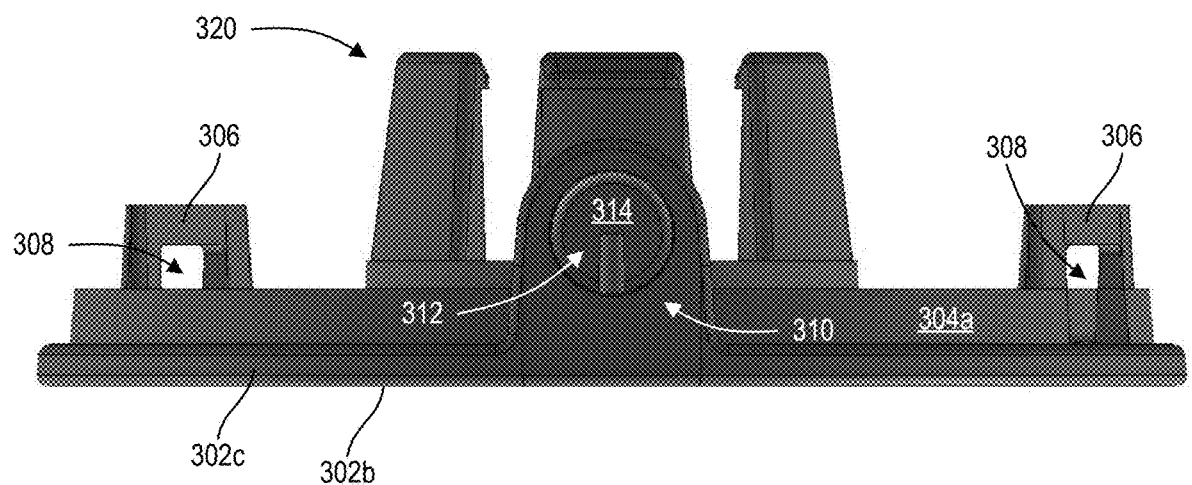

Referring now to FIG. 1, a dermal patch system 10 is shown in accordance with an exemplary embodiment. The dermal patch system 10 includes a lancet 100 and a cartridge 12 that can be affixed to a subject's skin via an adhesive layer 14 (FIG. 10). As will be discussed in further detail herein, the lancet 100 can engage with the cartridge 12 to deploy a needle disposed within the lancet housing to puncture the subject's skin thereby drawing a physiological sample from the subject.

Figure 2:
FIGS. 2 and 3 depict a lancet of the dermal patch system in accordance with an exemplary embodiment of the present disclosure.
Figure 3:
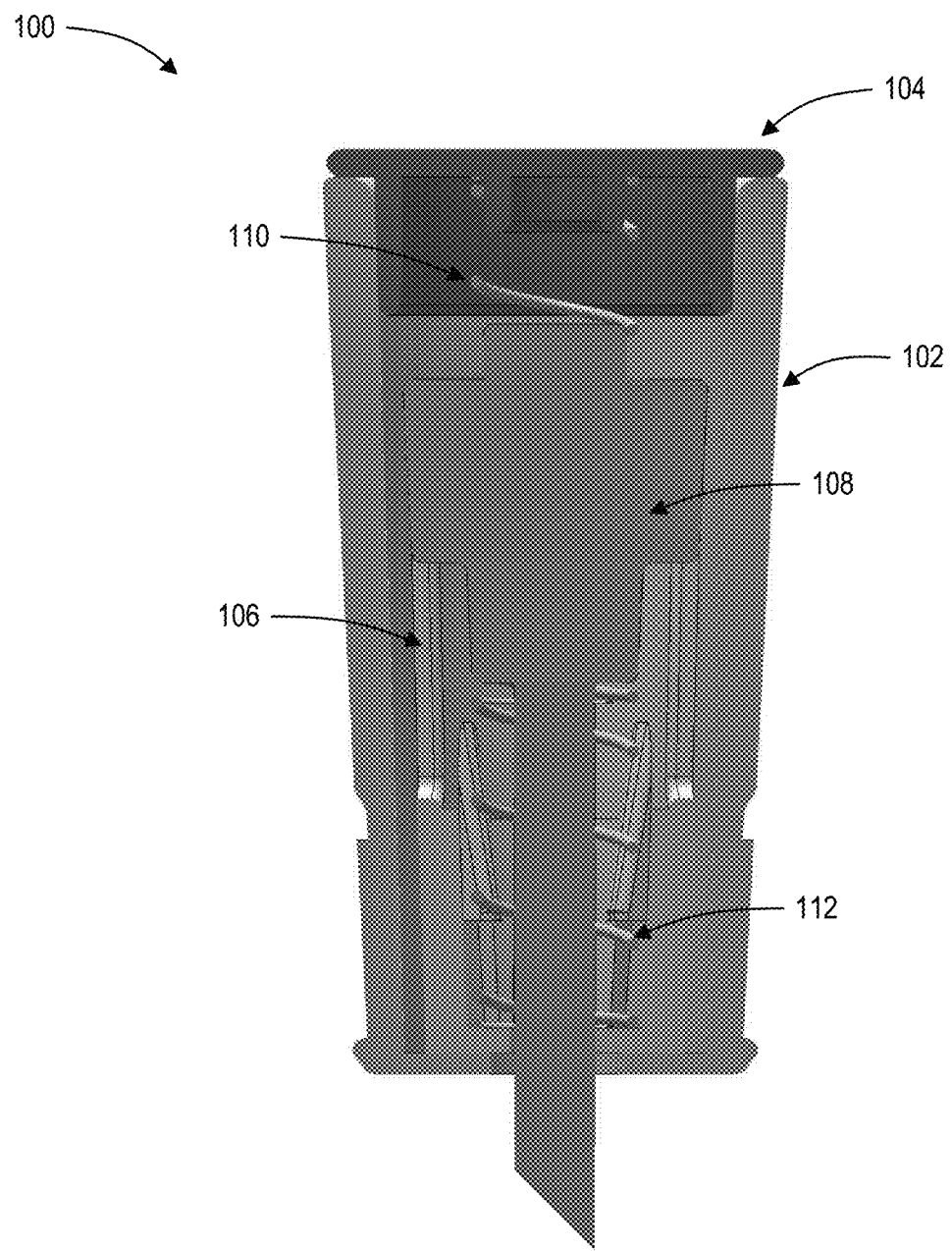

Referring now to FIGS. 2 and 3, the lancet 100 is shown in accordance with an exemplary embodiment. The lancet 100 includes a housing 102 in which various components of the lancet are disposed and a cap 104 that is coupled to the housing 102. The lancet 100 can further include an inner sleeve 106 within the housing 102 and a needle frame 108 that is disposed within the inner sleeve 106 and onto which a needle 158 is mounted. The lancet 100 also can include an injection spring 110 and a retraction spring 112 that move the needle 158 of the lancet 100 between various positions.

Figure 5:
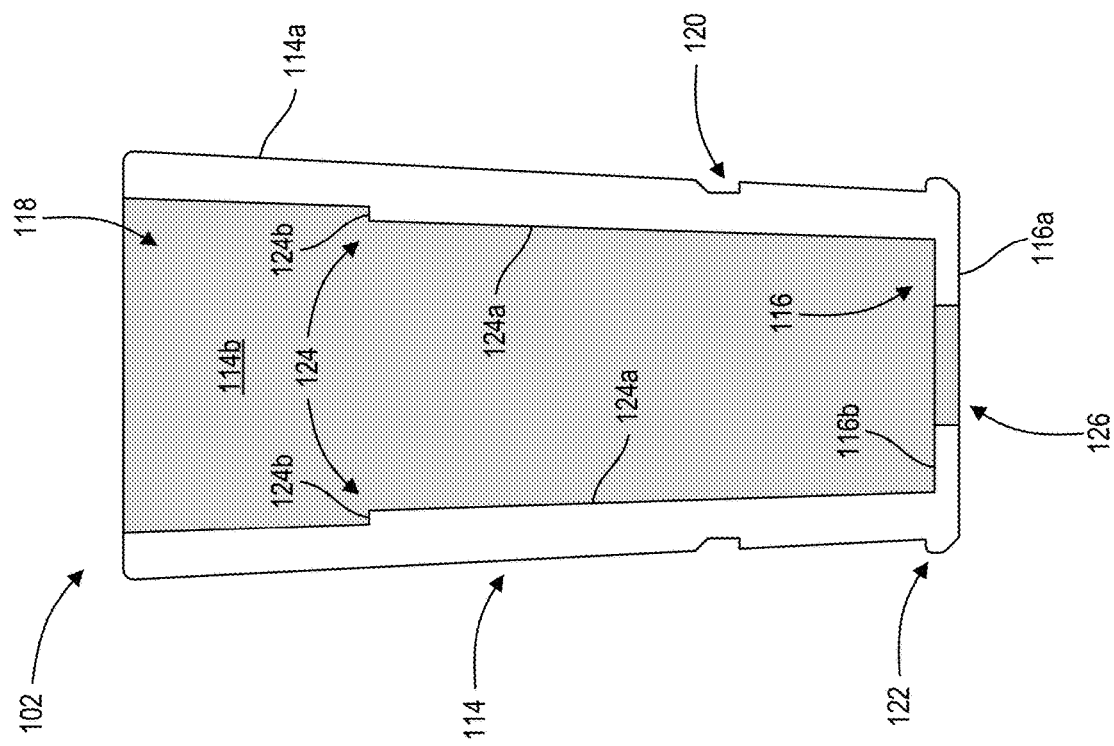
Figure 4:
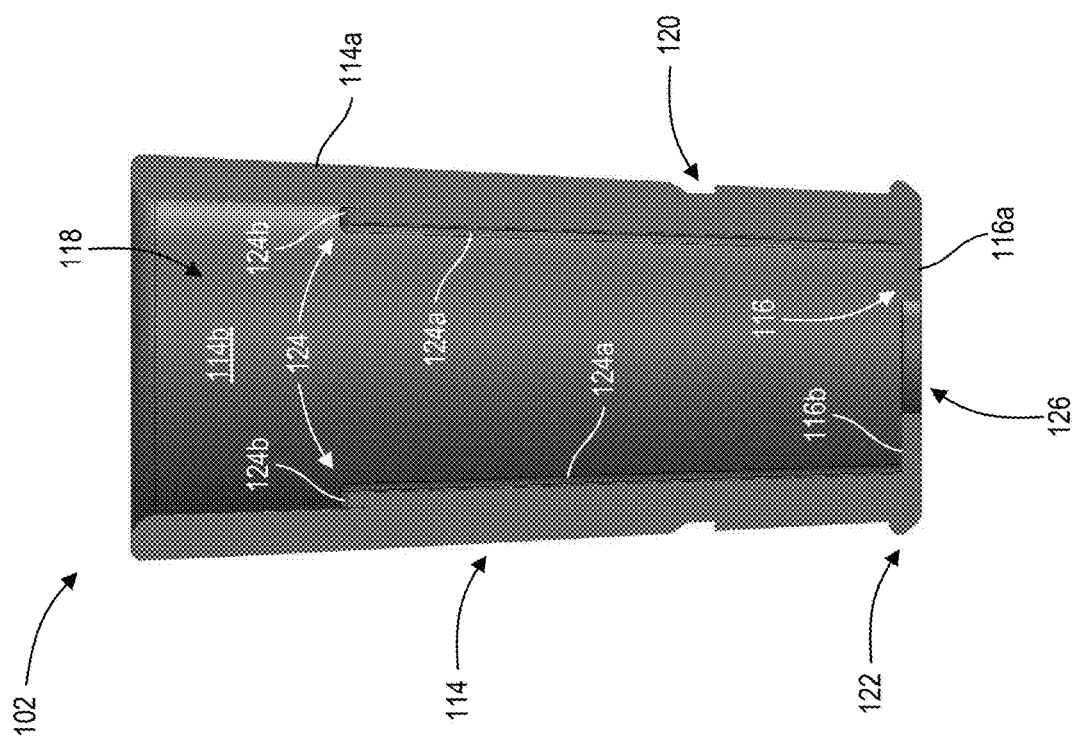
FIG. 4 depicts a housing of the lancet in accordance with an exemplary embodiment of the present disclosure FIG. 5 diagrammatically depicts a housing of the lancet in accordance with an exemplary embodiment of the present disclosure.

With particular reference to FIGS. 4 and 5, the housing 102 includes a side wall 114 and a bottom wall 116. The side wall 114 includes an outer surface 114a and an opposed inner surface 114b. The bottom wall 116 includes an outer surface 116a and an opposed inner surface 116b. The side wall 114 extends vertically from the bottom wall 116. The side wall 114 has a generally cylindrical shape and the bottom wall 116 is generally circular in shape and is concentric relative to a longitudinal axis of the generally cylindrical side wall and covers a lower opening formed by the generally cylindrical side wall. The inner surface 114b of the side wall 114 and the inner surface 116b of the bottom wall 116 define an inner volume 118.

The outer surface 114a defines a notch 120 that extends circumferentially around the outer surface 114a of the side wall 114. As will be discussed in further detail herein, the notch 120 is shaped and dimensioned to couple to a locking member of the cartridge 12 via a snap fit. The housing 102 further includes a rim 122 that extends circumferentially around the outer surface 114a of the side wall 114. The inner surface 114b defines a first and second column 124 that extend vertically from the inner surface 116b of the bottom wall 116. The columns 124 include an inner surface 124a and a top surface 124b. The inner surface 124a extends vertically between the inner surface 116b of the bottom wall 116 and the top surface 124b. The top surface 124b extends longitudinally between the inner surface 114b of the side wall 114 and the inner surface 124a.

As will be discussed in further detail herein, before the lancet 100 is inserted into the cartridge 12 the columns 124 retain the needle 158 of the lancet 100 in an undeployed position.

The bottom wall 116 defines an aperture 126 that extends through the bottom wall 116. Stated another way, the aperture 126 extends between the outer surface 116a and the inner surface 116b of the bottom wall 116. As will be discussed in further detail herein, when the lancet is activated via engagement with the cartridge 12, the needle of the lancet 100 is activated to extend through the aperture 126 and puncture the subject's skin thereby providing a passageway through which a physiological sample can be drawn from a subject.

Figure 6:
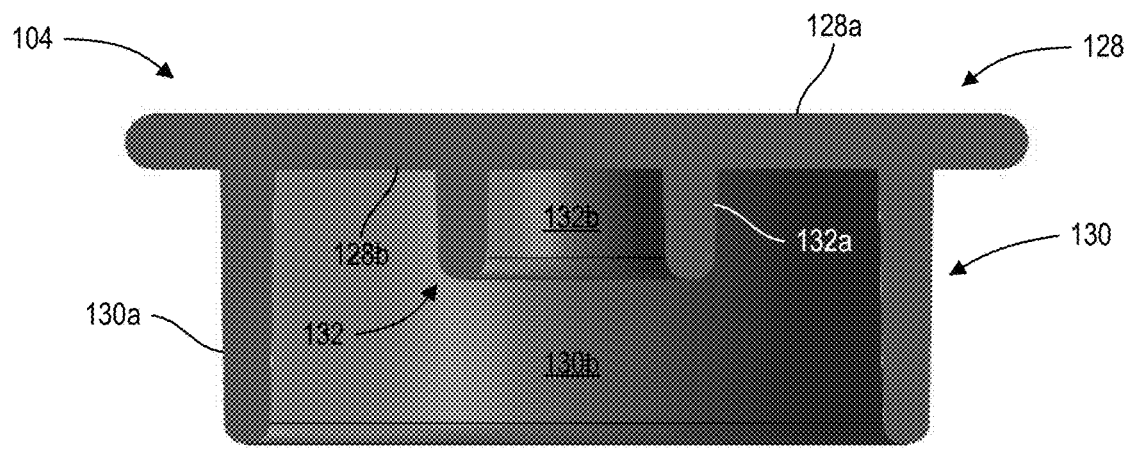
FIG. 6 depicts a cap of the lancet in accordance with an exemplary embodiment of the present disclosure.
Figure 7:
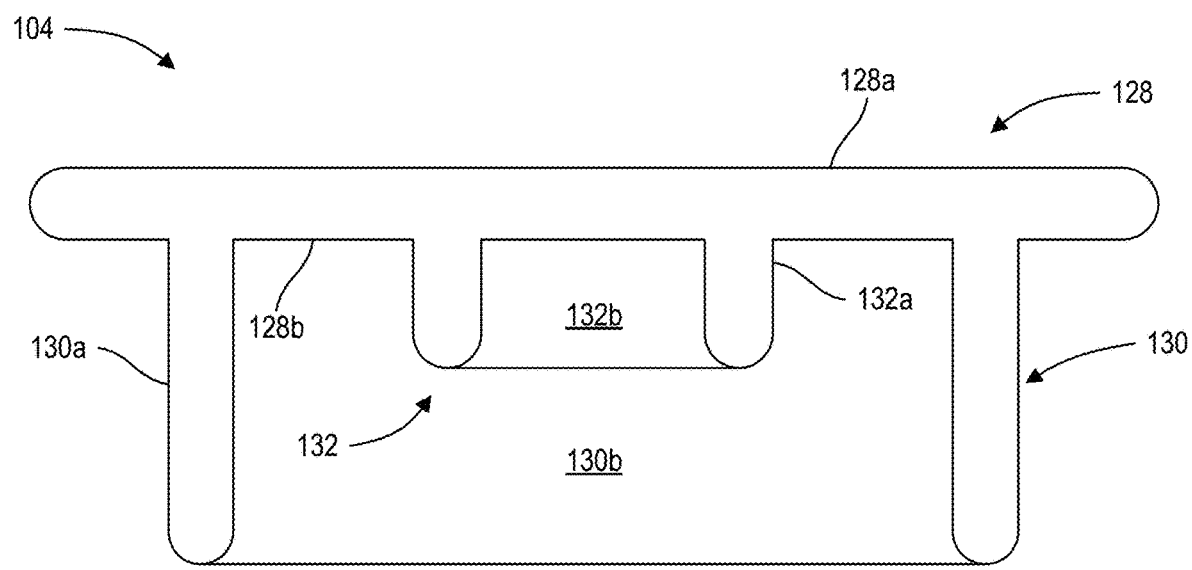
FIG. 7 diagrammatically depicts a cap of the lancet in accordance with an exemplary embodiment of the present disclosure.

With particular reference to FIGS. 6 and 7 the cap 104 includes a top wall 128 with an outer surface 128a and an opposed inner surface 128b. The cap 104 also includes a side wall 130 with an outer surface 130a and an opposed inner surface 130b. The top wall 128 extends longitudinally from and perpendicular to the side wall 130. The side wall 130 extends vertically from and perpendicular to the top wall 128. The top wall 128 and the side wall 130 are generally circular in shape and are concentric with one another. The cap 104 also includes an inner cylinder 132 with an outer surface 132a and an opposed outer surface 132b. The inner cylinder 132 extends vertically from and perpendicular to the top wall 128. The inner cylinder 132 is concentric with the top wall 128 and the side wall 130.

When the cap 104 is coupled to the housing 102 the side wall 130 extends into the inner volume 118 of the housing 102 and at least a portion of the side wall 130 contacts the inner surface 114b of the side wall 114 such that the cap 104 couples to the housing 102 via an interference fit.

Figure 8:
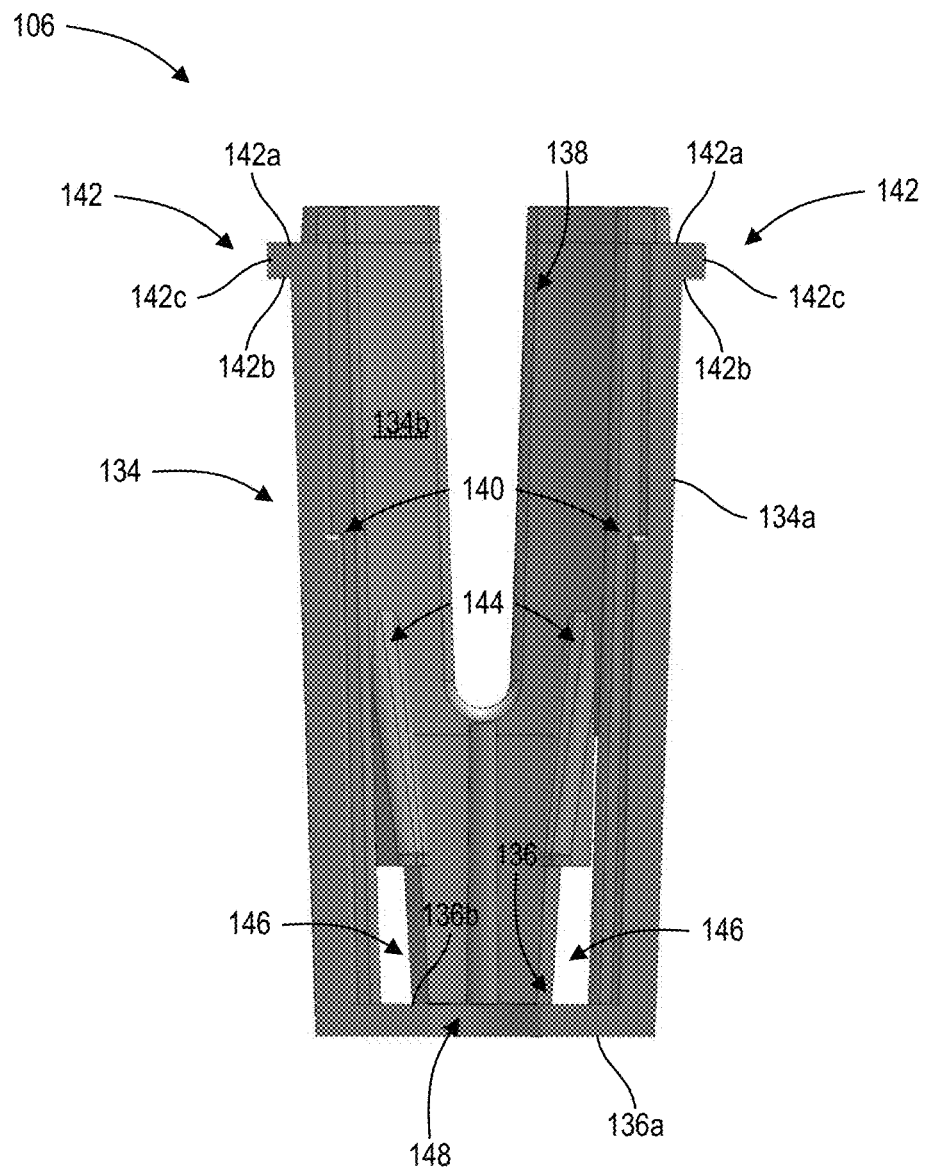
FIG. 8 depicts an inner sleeve of the lancet in accordance with an exemplary embodiment of the present disclosure.

As depicted in FIG. 8, the inner sleeve 106 includes a side wall 134 and a bottom wall 136. The side wall 134 includes an outer surface 134a and an opposed inner surface 134b. The bottom wall 136 includes an outer surface 136a and an opposed inner surface 136b. The side wall 134 extends vertically from the bottom wall 136. The side wall 134 and the bottom wall 136 are generally circular in shape and are concentric with one another. The inner surface 134b of the side wall 134 and the inner surface 136b of the bottom wall 136 define an inner volume 138. The inner surface 134b defines a plurality of columns 140 each of which extends vertically from and perpendicular to the inner surface 136b of the bottom wall 136. As will be discussed in further detail herein, when the needle frame 108 is in a deployed position, a portion of the needle frame 108 rests upon the columns 140.

The inner sleeve 106 further includes a plurality of ledges 142. Each ledge 142 includes a top surface 142a, an opposed bottom surface 142b and an outer surface 142c that extends between the top surface 142a and the bottom surface 142b. The inner sleeve 106 also includes a plurality of locking members 144 that extend from the inner surface 134b of the side wall 134. As will be discussed in further detail herein, the proximal end of the locking members 144 retains the retraction spring 112 in a compressed state in absence of engagement between the lancet 100 and the cartridge 12. The side wall 134 further defines a plurality of openings 146 that extend through the side wall 134. Stated another way, the openings 146 extend between the outer surface 134a and the inner surface 134b of the side wall 134. Each of the openings 146 are aligned with a proximal end of a locking member 144 to allow the proximal end of a locking member 144 to extend therethrough.

The bottom wall 136 defines an aperture 148 that extends through the bottom wall 136. Stated another way, the aperture 148 extends between the outer surface 136a and the inner surface 136b of the bottom wall 136. The aperture 148 is concentric with the aperture 126 of the housing 102. As will be discussed in further detail herein, when in a deployed position, the needle 158 of the lancet 100 extends through the aperture 148 of the inner sleeve 106 as well as the aperture 126 of the housing 102.

Figure 9:
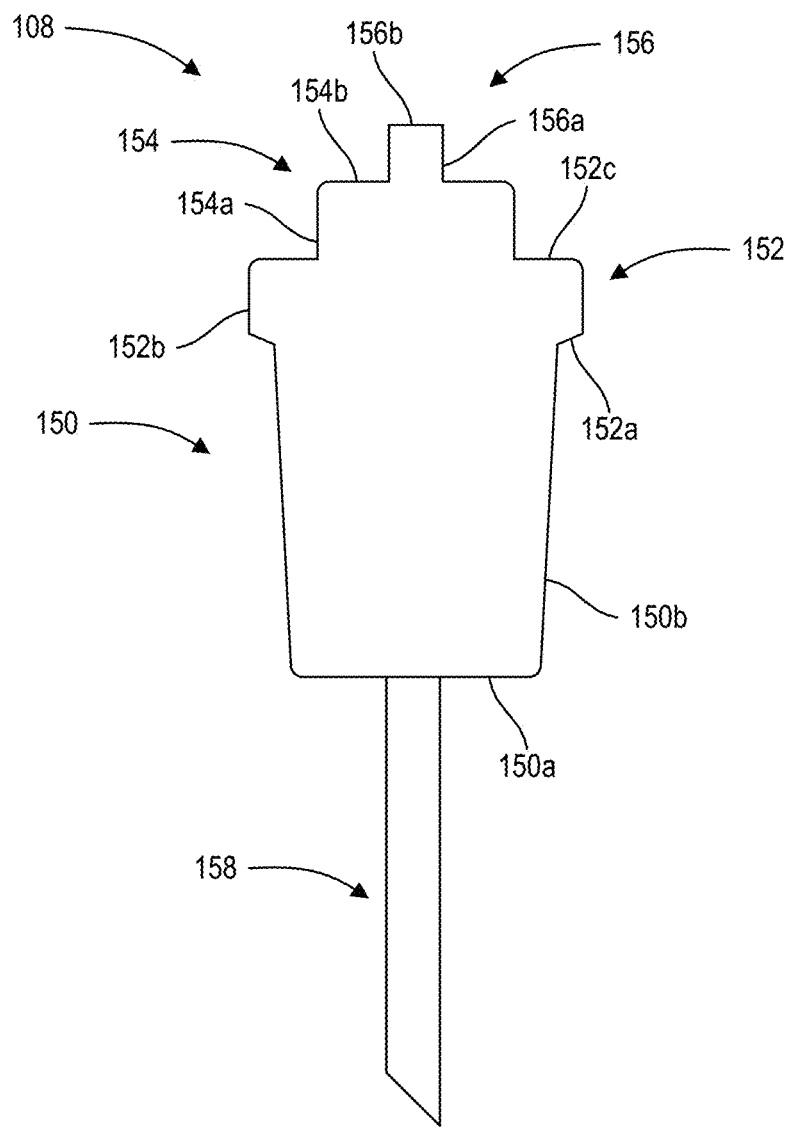
FIG. 9 diagrammatically depicts a needle frame of the lancet in accordance with an exemplary embodiment of the present disclosure.

As depicted in FIG. 9, the needle frame 108 includes a first cylinder 150, a second cylinder 152, a third cylinder 154, and a protrusion 156. The second cylinder is disposed vertically above the first cylinder 150. The first cylinder 150 includes a bottom surface 150a and an outer surface 150b. The second cylinder 152 is disposed vertically above the first cylinder 150 and the third cylinder 154 is disposed vertically above the second cylinder 152. The first cylinder 150 includes a bottom surface 150a and an outer surface 150b and the second cylinder 152 includes a bottom surface 152a, an outer surface 152b and a top surface 152c. The third cylinder 154 includes an outer surface 154a and a top surface 154b. Similarly, the protrusion 156 includes an outer surface 156a and a top surface 156b.

The bottom surface 150a of the first cylinder extends circumferentially about the outer surface 150b of the first cylinder. The outer surface 150b of the first cylinder 150 extends vertically between the bottom surface 150a of the first cylinder 150 and the bottom surface 152a of the second cylinder 152. The bottom surface 152a of the second cylinder 152 extends at an angle longitudinally between the outer surface 150b of the first cylinder and the outer surface 152b of the second cylinder 152. The outer surface 152b extends vertically between the bottom surface 152a and the top surface 152c of the second cylinder 152. The top surface 152c of the second cylinder 152 extends longitudinally between the outer surface 152b of the second cylinder and the outer surface 154a of the third cylinder 154. The outer surface 154a extends vertically between the top surface 152c of the second cylinder and the top surface 154b of the third cylinder. The top surface 154b of the third cylinder extends longitudinally between the outer surface 154a of the third cylinder 154 and the outer surface 156a of the protrusion 156. The outer surface 156a extends vertically between the top surface 154b of the third cylinder and the top surface 156b of the protrusion 156. The top surface 156b of the protrusion 156 extends across a proximal end of the outer surface 156a.

The injection spring 110 extends vertically between the cap 104 and the needle frame 108. More specifically, a distal end of the injection spring 110 contacts the inner surface 128b of the top wall 128 and a proximal end of the injection spring 110 contacts the top surface 152c of the second cylinder 152. The distal end of the injection spring 110 extends circumferentially around the outer surface 132a of the inner cylinder 132. The proximal end of the injection spring 110 extends circumferentially around the third cylinder 154 and around the protrusion 156.

The needle frame 108 supports the needle 158. In some embodiments, the needle frame 108 is molded into the first cylinder 150 or is attached to the bottom surface 150a of the first cylinder 150 (e.g., via an adhesive).

Referring now to FIG. 10, the cartridge 12 is shown in accordance with an exemplary embodiment. The cartridge 12 includes a cover 200 and a base 300 that can couple to the cover 200. For example, the cover 200 and the base 300 can be formed as two separate components that are removably coupled to one another (e.g., via a snap fitting). In other embodiments, the cover 200 and the base 300 form an integral unitary cartridge 12. In some of these embodiments, the cover 200 can be coupled to the base 300 via an adhesive, laser welding, etc. The dermal patch system 10 also includes a vacuum pin 400. As will be discussed in further detail herein, the vacuum pin 400 can be disposed within the cartridge 12 and is configured to create a vacuum within the cartridge 12.

The cartridge 12 may be formed using a variety of suitable materials including, but not limited to, polymeric materials (e.g., polyolefins, polyethylene terephthalate (PET), polyurethanes, polynorbornenes, polyethers, polyacrylates, polyamides (Polyether block amide also referred to as Pebax®), polysiloxanes, polyether amides, polyether esters, trans-polyisoprenes, polymethyl methacrylates (PMMA), cross-linked trans-polyoctylenes, cross-linked polyethylenes, cross-linked polyisoprenes, cross-linked polycyclooctenes, inorganic-organic hybrid polymers, co-polymer blends with polyethylene and Kraton®, styrene-butadiene co-polymers, urethane-butadiene co-polymers, polycaprolactone or oligo caprolactone co-polymers, polylactic acid (PLLA) or polylactide (PL/DLA) co-polymers, PLLA-polyglycolic acid (PGA) co-polymers, photocross linkable polymers, etc.). In some embodiments, some of the cover 200 may be formed of poly(dimethylsiloxane) (PDMS) to allow visibility of components disposed within the cartridge 12.

Referring now to FIGS. 11-16 the cover 200 is shown in accordance with an exemplary embodiment. In this embodiment, the cover 200 includes a top wall 202 with an outer surface 202a and an opposed inner surface 202b. The cover 200 also includes a side wall 204 with an outer surface 204a and an opposed inner surface 204b. The top wall 202 extends longitudinally from and perpendicular to the side wall 204. The side wall 204 extends vertically from and perpendicular to the top wall 202.

The side wall 204 defines a U-shaped opening 206. The U-shaped opening 206 extends through the side wall 204. Stated another way, the U-shaped opening 206 extends between the outer surface 204a and the inner surface 204b of the side wall 204. The U-shaped opening 206 is shaped and dimensioned to accommodate at least a portion of the vacuum pin 400. As will be discussed in further detail herein, U-shaped opening 206 allows the vacuum pin 400 to be received by a receptacle (which can be in the form of a channel) within the cartridge 12. That is, the U-shaped opening 206 is shaped to accommodate the vacuum pin 400 such that at least a portion of the vacuum pin 400 can extend through the side wall 204 to be disposed within a receptacle provided in the base 300.

The top wall 202 defines a lancet aperture 208 that is generally circular in shape. The lancet aperture 208 extends through the top wall 202. Stated another way, the lancet aperture 208 extends between the outer surface 202a and the inner surface 202b of the top wall 202. The lancet aperture 208 is shaped to accommodate at least a portion of the lancet 100. As will be discussed in further detail herein, the lancet aperture 208 allows the lancet 100 to couple to the base 300. That is, the lancet aperture 208 is shaped to accommodate the lancet 100 such that at least a portion of the lancet 100 can extend through the top wall 202.

The cover 200 also includes a funnel-like channel 212 that provides a viewing aperture 210. In some embodiments, the cover 200 can further include a transparent window (not shown), e.g., formed of PDMS, that extends across the viewing aperture 210. The viewing aperture 210 allows a user of the dermal patch system 10 to view components (e.g., a specimen collection pad) disposed within the dermal patch system 10. The side wall of the funnel-like channel 212 is slanted to facilitate viewing of the one or more components disposed within the cartridge 12.

The cover 200 further includes a plurality of projection members 214. The projection members 214 extend vertically from and perpendicular to the inner surface 202b of the top wall 202. The projection members 214 are disposed around the perimeter of the lancet aperture 208. As will be discussed in further detail herein, the projection members 214 secure the cover 200 to the base 300.

The cover 200 also includes a U-shaped locking member 216 and a plurality of locking members 218. The U-shaped locking member 216 is aligned with the U-shaped opening 206. The U-shaped locking member 216 extends vertically from and perpendicular to the inner surface 202b of the top wall 202. When the cover 200 is coupled to the base 300, the U-shaped locking member 216 retains the vacuum pin 400 within the base 300 while allowing the vacuum pin 400 to move a predetermined distance while remaining within the cartridge 12. The locking members 218 extend longitudinally from and perpendicular to the inner surface 204b of the side wall 204. As will be discussed in further detail herein, the 218 secure the cover 200 to the base 300.

With reference to FIGS. 17-27, the base 300 is shown in accordance with an exemplary embodiment. In this embodiment, the base 300 includes a bottom wall 302 with a top surface 302a, an opposed bottom surface 302b, and an outer surface 302c that extends between the top surface 302a and the bottom surface 302b. The top surface 302a and the bottom surface 302b extend perpendicularly to the outer surface 302c. The outer surface 302c extends perpendicular to and vertically between the top surface 302a and the bottom surface 302b. The bottom wall 302 and the side wall 204 of the cover 200 have the same perimeter shape such that when the cover 200 is coupled to the base 300, outer surface 302c of the base 300 and the outer surface 204a of the cover 200 are flush with one another. Furthermore, when the cover 200 is coupled to the base 300, the side wall 204 contacts the top surface 302a of the bottom wall 302.

The base 300 further includes a rim 304 with an outer surface 304a, an opposed inner surface 304b, and a top surface 304c that extends between the outer surface 304a and the inner surface 304b. The top surface 304c extends perpendicularly to and longitudinally between the outer surface 304a and the inner surface 304b. The outer surface 304a and the inner surface 304b extend vertically from and perpendicular to the top surface 302a of the bottom wall 302 such that the outer surface 304a and the inner surface 304b extend between the top surface 302a and the top surface 304c. The rim 304 is contoured such that when the cover 200 is coupled to the base, at least a portion of the side wall 204 contacts at least a portion of the rim 304. More specifically, at least a portion of the inner surface 204b of the side wall 204 contacts at least a portion of the outer surface 304a of the rim 304.

Figure 31:
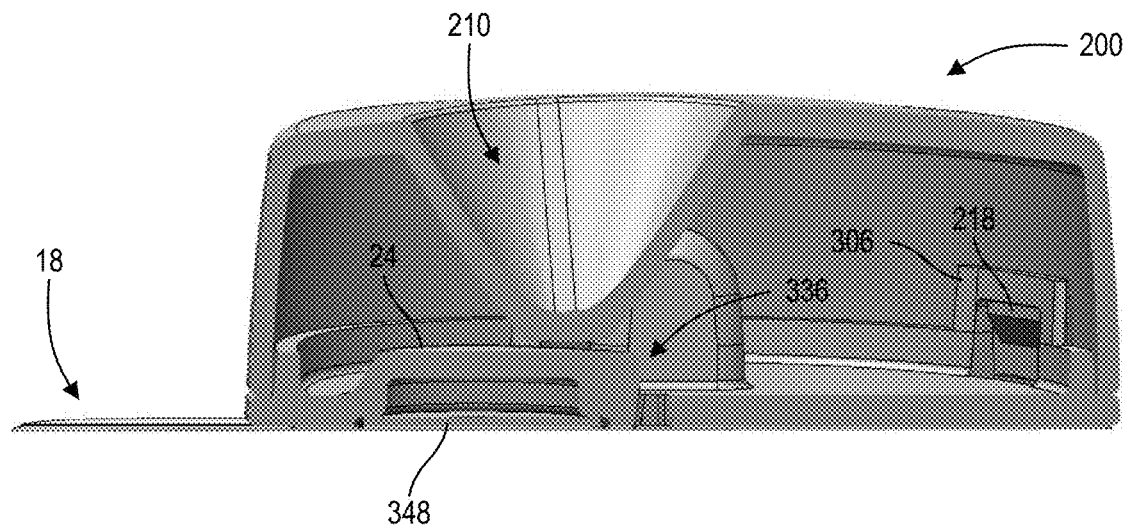
FIG. 31 depicts a dermal patch system in accordance with an exemplary embodiment of the present disclosure.

The base 300 further includes a plurality of extensions 306 that extend vertically from and perpendicular to the rim 304. The extensions 306, the bottom wall 302 and the rim 304 define gaps 308. The gaps 308 and therefore the extensions 306, are shaped to accept a locking member 218 such that an extension 306 couples to a locking member 218 via a snap fitting thereby coupling the cover 200 to the base 300 (FIG. 31).

The base 300 also includes a vacuum pin receptacle 310 that extends vertically from and perpendicular to the top surface 302a of the bottom wall 302. The vacuum pin receptacle 310 includes an opening 312 and a chamber 314 that are each shaped to accept the vacuum pin 400 such that at least a portion of the vacuum pin 400 may be disposed within the vacuum pin receptacle 310. The vacuum pin receptacle 310 also includes a gap 316 that is shaped and dimensioned to accommodate the arms of the U-shaped locking member 216. That is, when the cover 200 is coupled to the base 300, the arms of the U-shaped locking member 216 extend through and are disposed within the gap 316.

The base 300 also includes a needle aperture 318 that is generally circular in shape. The needle aperture 318 extends through the bottom wall 302. Stated another way, the needle aperture 318 extends between the top surface 302a and the bottom surface 302b of the bottom wall 302. As will be discussed in further detail herein, when the cover 200 is coupled to the base 300 and when the cartridge 12 is adhered to a subject, the needle aperture 318 allows the needle 158 of the lancet 100 to extend through the bottom wall 302 to puncture the subject's skin, thereby allowing extraction of a physiological sample from the subject.

Figure 20:
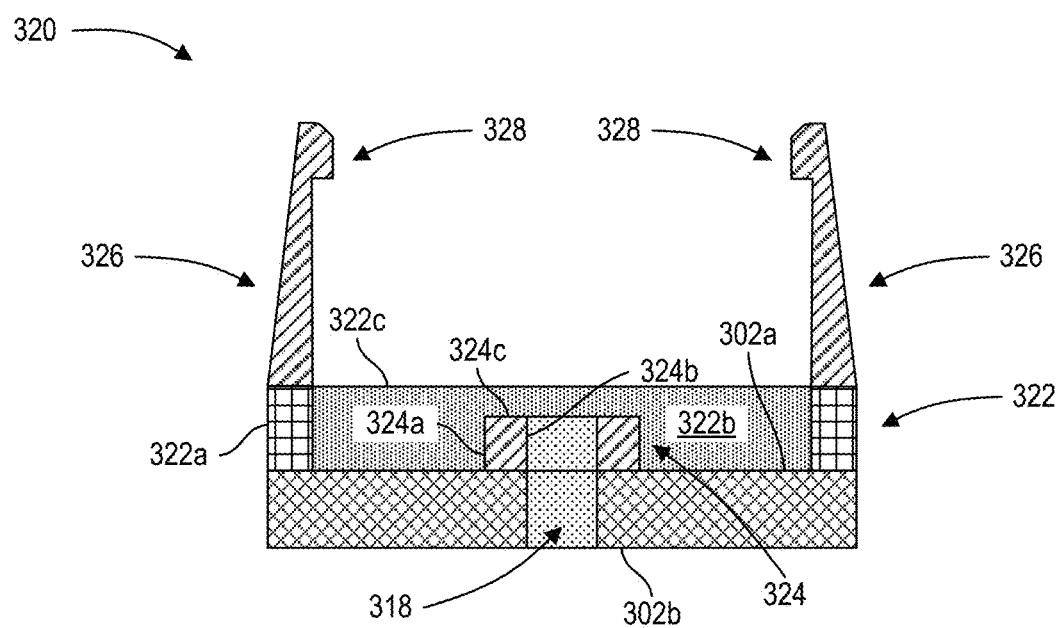
FIG. 20 diagrammatically depicts a lancet receiving element of the base in accordance with an exemplary embodiment of the present disclosure.

The base 300 further includes a lancet receiving element 320 that is shaped and dimensioned to accept the distal end of the lancet 100. With particular reference to FIG. 20, the lancet receiving element 320 includes an outer circular projection 322 and an inner circular projection 324 with each extending vertically from and perpendicular to the top surface 302a of the bottom wall 302. The outer circular projection 322 includes an outer surface 322a, an opposed inner surface 322b, and a top surface 322c that extends between the outer surface 322a and the inner surface 322b. The top surface 322c extends perpendicular to and longitudinally between the outer surface 322a and the inner surface 322b. The outer surface 322a and the inner surface 322b extend vertically from and perpendicular to the top surface 302a of the bottom wall 302 such that the outer surface 322a and the inner surface 322b extend between the top surface 302a and the top surface 322c. The outer circular projection 322 is shaped to accept the lancet 100.

The inner circular projection 324 is disposed around the needle aperture 318 and includes an outer surface 324a, an opposed inner surface 324b, and a top surface 324c that extends between the outer surface 324a and the inner surface 324b. The top surface 324c extends perpendicular to and longitudinally between the outer surface 324a and the inner surface 324b. The outer surface 324a and the inner surface 324b extend vertically from and perpendicular to the top surface 302a of the bottom wall 302 such that the outer surface 324a and the inner surface 324b extend between the top surface 302a and the top surface 324c. Furthermore, the outer circular projection 322 and the inner circular projection 324 circular projection are concentric with one another. As will be discussed in further detail herein, when a lancet is engaged with the base 300, the top surface 324c of the inner circular projection contacts a portion of the lancet 100 which allows the lancet to release the needle disposed in the lancet housing so as to puncture the skin, thereby allowing the extraction of a physiological sample from the subject's skin.

With continued reference to FIG. 20, the base 300 further includes a plurality of locking members 326 that extend vertically from and perpendicular to the top surface 322c of the outer circular projection 322. For the sake of clarity, one of the locking members 326 is not shown in FIG. 20. Each locking member 326 includes a hook 328 that extends inwardly from a top of a locking member 326 towards the inner circular projection 324. As will be discussed in further detail herein, the hooks 328 of the locking members 326 couple to the lancet 100 to retain the lancet 100 within the base 300. The locking members 326 are equally spaced around the outer circular projection 322 thereby defining a gap between the locking members 326. When the cover 200 is coupled to the base 300, the projection members 214 extend between the locking members 326 in these gaps thereby coupling the cover 200 to the base 300.

Figure 21:
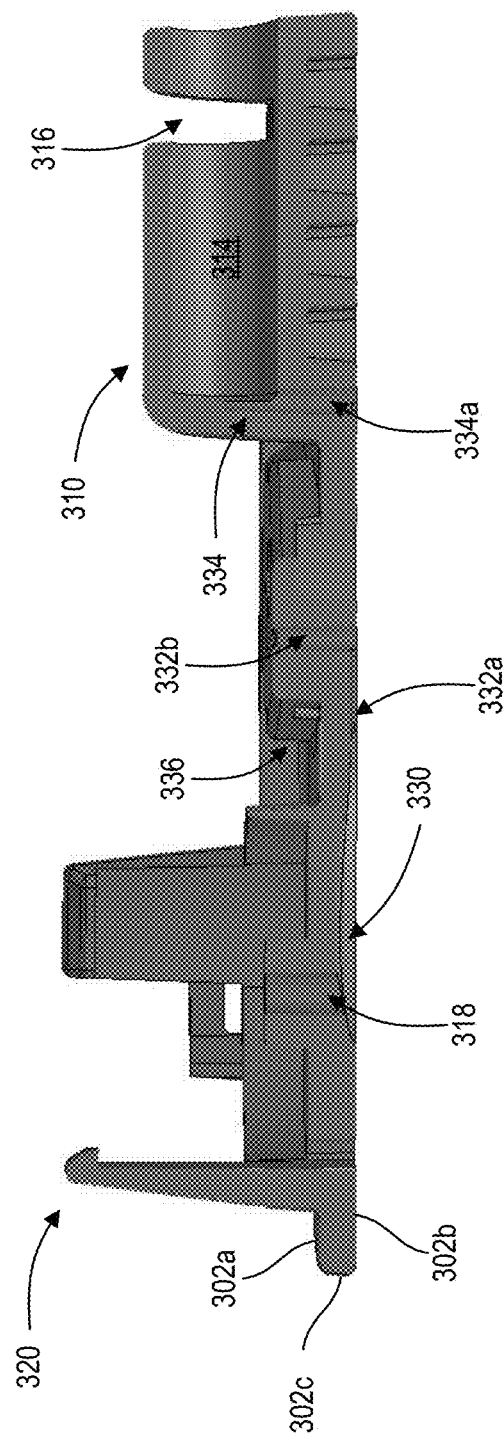
FIGS. 21-27 depict the base of the cartridge in accordance with an exemplary embodiment of the present disclosure.
Figure 22:
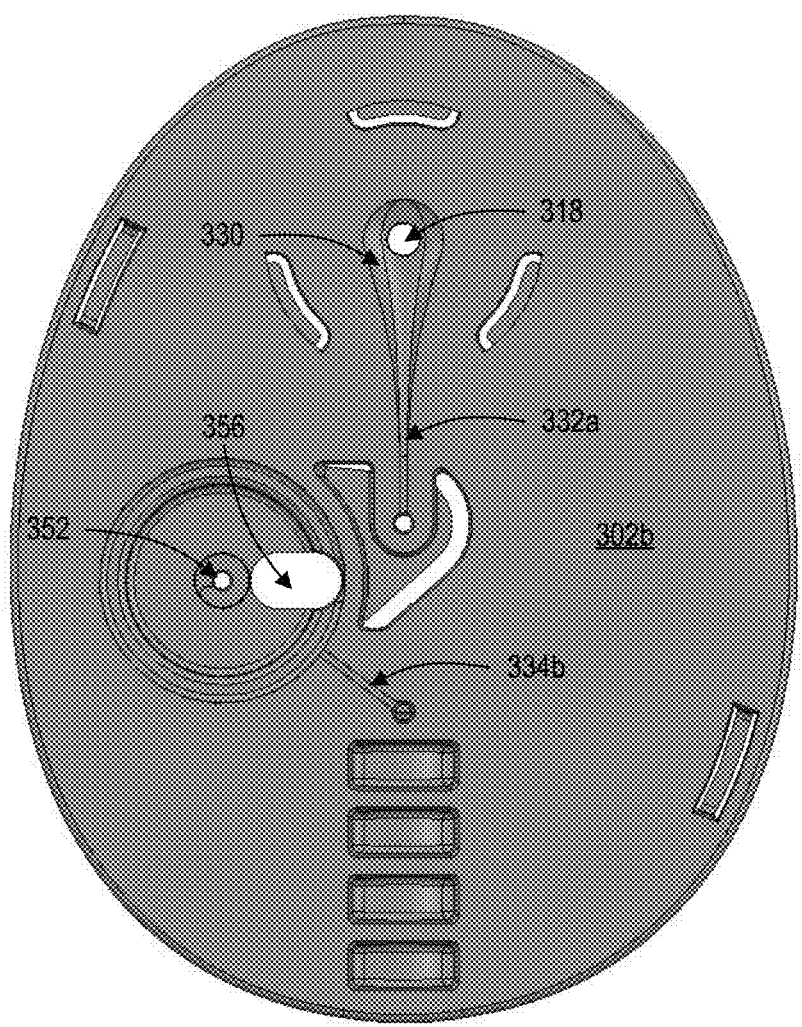
Figure 23:
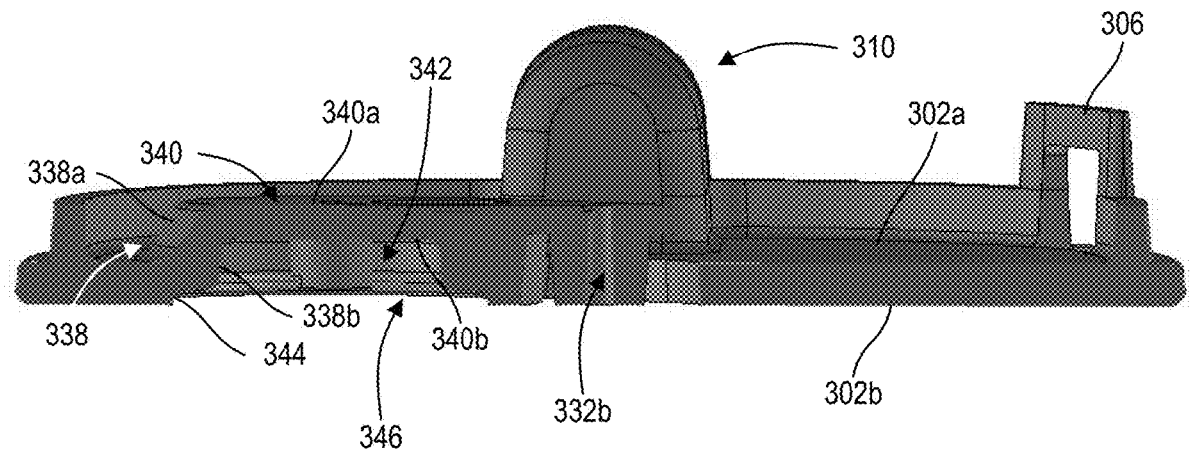
Figure 24:
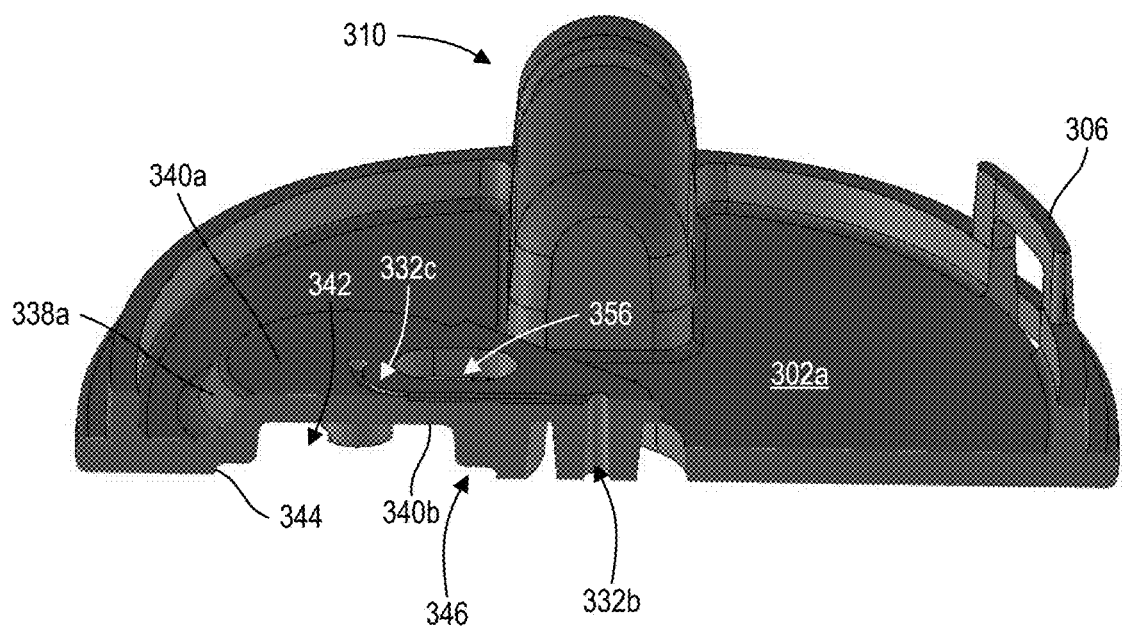

With particular reference to FIG. 21, the base 300 includes a physiological sample well 330 and a physiological sample channel 332 with a first portion 332a that extends from the physiological sample well 330. As will be discussed in further detail herein, the physiological sample channel 332 is a fluidic channel that is configured to carry a physiological sample extracted from a subject. The physiological sample well 330 and the first portion 332a of the physiological sample channel 332 are open with respect to the bottom surface 302b of the bottom wall 302. Stated another way, the physiological sample well 330 and the first portion 332a of the physiological sample channel 332 do not include a bottom surface. The physiological sample well 330 is in open communication with the needle aperture 318. As will be discussed in further detail herein, when drawing a physiological sample, a needle of the lancet 100 extends through the needle aperture 318 and through the physiological sample well 330 to pierce the skin of the subject.

The base 300 further includes a vacuum channel 334 that is in fluid communication with the chamber 314 of the vacuum pin receptacle 310. A first portion 334a of the vacuum channel 334 extends from the chamber 314 and extends vertically within the base 300. A second portion 334b of the vacuum channel 334 extends longitudinally from and perpendicular to the first portion 334a of the vacuum channel 334 such that the second portion 334b of the vacuum channel 334 extends along the bottom surface 302b of the bottom wall 302. Similar to the physiological sample well 330 and the first portion 332a of the physiological sample channel 332, the second portion 334b of the vacuum channel 334 is open with respect to the bottom surface 302b of the bottom wall 302.

The base 300 further includes a specimen collection pad housing 336. The specimen collection pad housing 336 includes a side wall 338 and a top wall 340. The side wall 338 extends vertically from and perpendicular to the top surface 302a of the bottom wall 302. The top wall 340 extends longitudinally from and perpendicular to the side wall 338. The side wall 338 includes an outer surface 338a and an opposed inner surface 338b. The top wall 340 includes an outer surface 340a and an opposed inner surface 340b. The outer surface 338a extends vertically from and perpendicular to the top surface 302a of the bottom wall 302 and the outer surface 340a of the top wall 340. The inner surface 338b extends vertically from and perpendicular to the bottom surface 302b of the bottom wall 302 and the inner surface 340b of the top wall 340. The outer surface 340a of the top wall 340 extends longitudinally from and perpendicular to opposing sides of the outer surface 338a of the side wall 338. The inner surface 340b of the top wall 340 extends longitudinally from and perpendicular to the inner surface 338b of the side wall 338.

The inner surface 338b of the side wall 338 and the inner surface 340b of the top wall 340 define an opening 342 of the specimen collection pad housing 336. The specimen collection pad housing 336 further includes a surface 344 located vertically below the inner surfaces 338b and 340b. The surface 344 defines a specimen collection pad receptacle 346. The specimen collection pad receptacle 346 and therefore the surface 344 is shaped to accommodate a specimen collection pad 348. The specimen collection pad 348 may be formed of any material that is capable of absorbing a physiological sample. In some embodiments, the specimen collection pad 248 may be a CF12 collection pad. A CF12 collection pad includes a dried blood spot filter paper that can be used as a specimen collection pad.

The base 300 includes the adhesive layer 14 disposed on the bottom surface 302b of the bottom wall 302 for attaching the cartridge 12 to the skin of a subject. The adhesive layer 14 may be laminated to or heat/laser/adhesively bonded to the bottom surface 302b of the bottom wall 302. The cartridge 12 may be attached anywhere on the subject's skin that is capable of supporting the cartridge 12 (e.g., on a leg, arm, etc. of the subject). In some embodiments, a removable protective liner (not shown in the figures) covers the adhesive surface of the adhesive layer 14 and may be removed to expose the adhesive surface for attachment onto the subject's skin.

Figure 28:
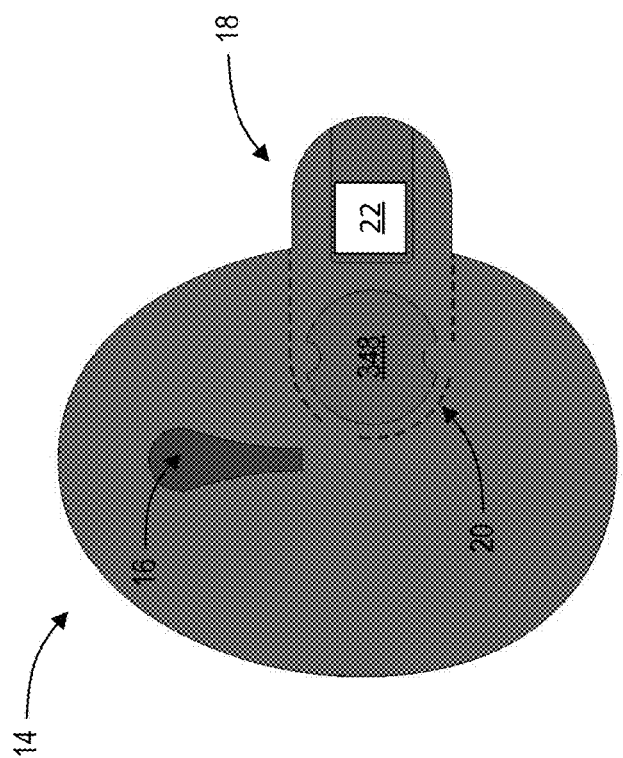
FIG. 28 diagrammatically depicts an adhesive layer of the dermal patch in accordance with an exemplary embodiment of the present disclosure.

As depicted in FIG. 28, the adhesive layer 14 includes an opening 16 that surrounds the physiological sample well 330. The opening 16 allows the needle 158 of the lancet 100 to penetrate the skin, when the needle 158 is activated, without piercing the adhesive layer 14. Further, subsequent to the puncturing of the skin via the needle of the lancet 100, the opening 16 allows drawing a physiological sample from the subject, which is received within the physiological sample well 330. The adhesive layer 14 covers and therefore seals the first portion 332a of the physiological sample channel 332 and the second portion 334b of the vacuum channel 334.

In some embodiments of the cartridge 12, the adhesive layer 14 supports a specimen collection pad 348. That is, the specimen collection pad 348 can be adhered to a portion of the adhesive layer 14. In these embodiments, the specimen collection pad 348 includes a pull tab 18 that extends from the adhesive layer 14 and a perforation 20 that surrounds the specimen collection pad 348. The specimen collection pad 348 is positioned on the adhesive layer 14 such that when the adhesive layer 14 is disposed on the bottom surface 302b of the bottom wall 302, the specimen collection pad 348 is disposed within the specimen collection pad receptacle 346. The perforation 20 allows a user to remove the specimen collection pad 248 from the cartridge 12. That is, a user can pull the pull tab 18 to separate a portion of the adhesive layer 14 associated with the specimen collection pad 348 from the remainder of the adhesive layer 14.

Figure 29:
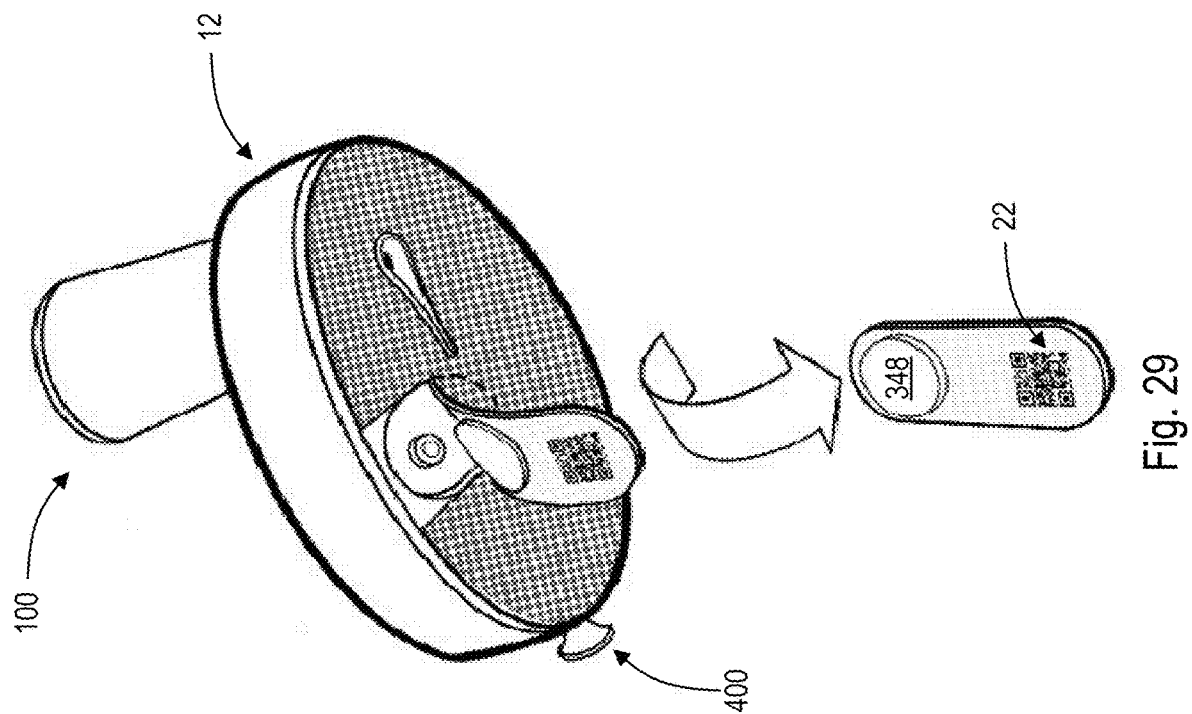
FIG. 29 diagrammatically depicts a physiological sample pad being removed from the dermal patch in accordance with an exemplary embodiment of the present disclosure.

In some embodiments, as depicted in FIGS. 28 and 29, the base 300 may further include a quick response ("QR") code 22. While FIGS. 28 and 29 depict the adhesive layer 14 as supporting the QR code 22, it is understood that the QR code 22 may be positioned elsewhere on the cartridge 12 (e.g., on the outer surface 202a of the top wall 202). As will be discussed in further detail herein, the QR code 22 can be associated with an electronic medical record stored in an electronic medical record database.

Figure 25:
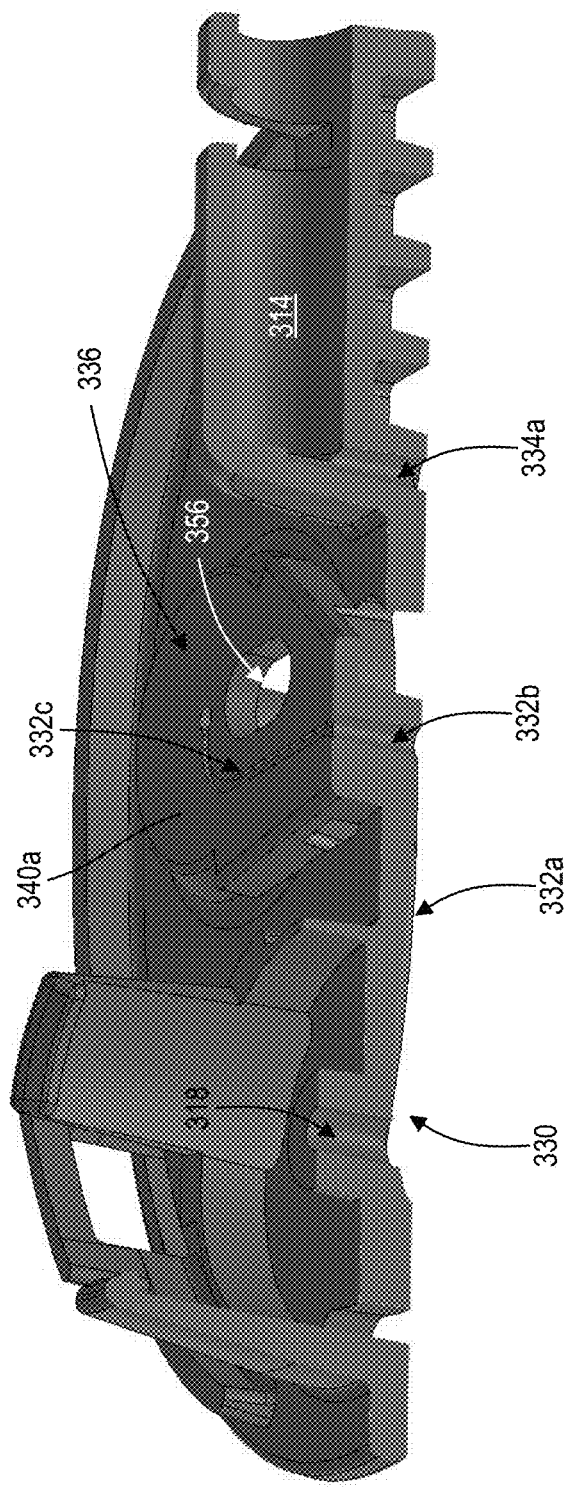
Figure 26:
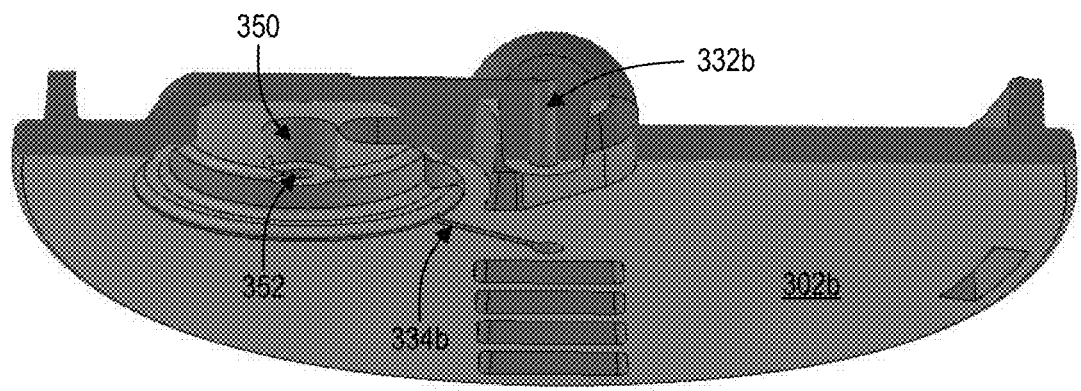
Figure 27:
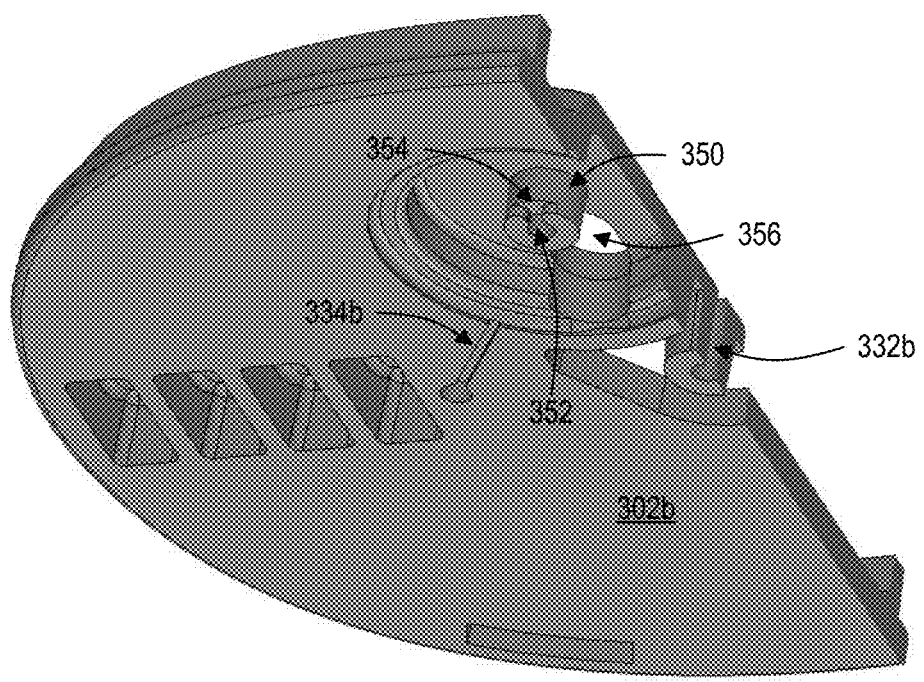

As depicted in FIG. 25, the physiological sample channel 332 further includes a second portion 332b and a third portion 332c. The second portion 332b of the physiological sample channel 332 is in open and fluid communication with the first portion 332a of the physiological sample channel 332. As such, the second portion 332b of the physiological sample channel 332 is in open and fluid communication with the physiological sample well 330. The second portion 332b extends vertically from and perpendicular to the first portion 332a of the physiological sample channel 332. Furthermore, the second portion 332b extends vertically within the specimen collection pad housing 336.

The third portion 332c is in open and fluid communication with the second portion 332b of the physiological sample channel 332. As such, the third portion 332c is in open and fluid communication with the physiological sample well 330. The third portion 332c extends longitudinally from and perpendicular to the second portion 332b. The third portion 332c extends longitudinally along the outer surface 340a of the top wall 340. The third portion 332c is open with respect to the outer surface 340a of the top wall 340. Stated another way, the third portion 332c does not include a top surface.

Figure 30:
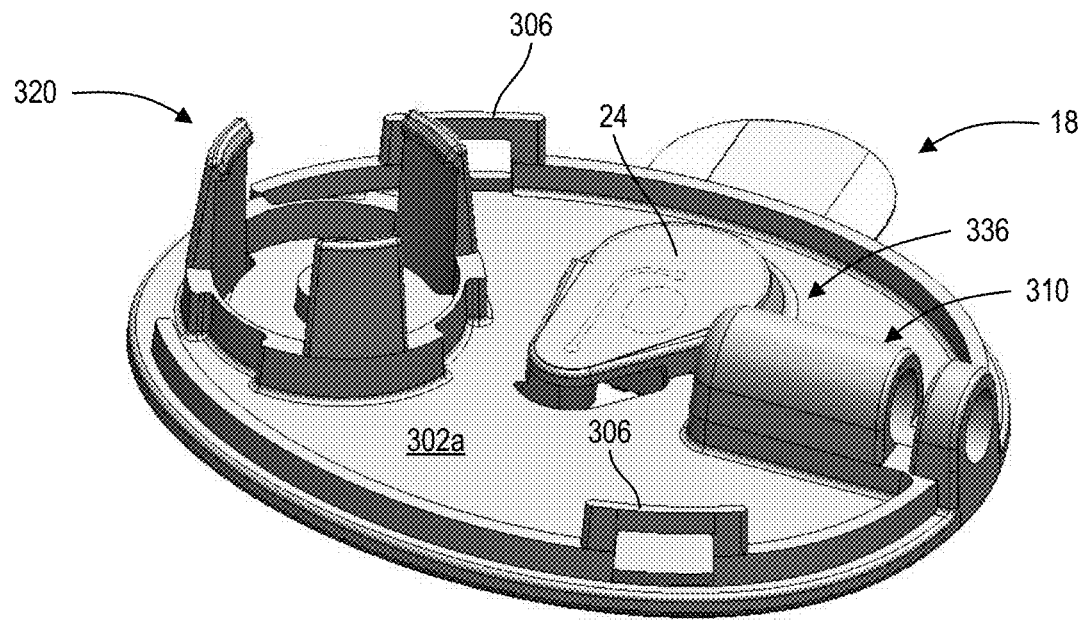
FIG. 30 further depicts the base of the cartridge in accordance with an exemplary embodiment of the present disclosure.

With particular reference to FIG. 30, the cartridge 12 further includes a film 24 positioned vertically above the outer surface 340a of the top wall 340. In some embodiments, the film 24 includes an adhesive such that the film 24 can be affixed to the outer surface 340a of the top wall 340. The film 24 is shaped and dimensioned to cover the outer surface 340a. Accordingly, the film 24 covers and seals the third portion 332c of the physiological sample channel 332.

The specimen collection pad housing 336 further includes a channel 354 that is formed by a cylinder 350 that extends vertically from and perpendicular to the inner surface 340b of the top wall 340. The cylinder 350 extends into the opening 342 and the specimen collection pad receptacle 346. The cylinder 350 defines an opening 352 that extends through the cylinder 350. The opening 352 is in open and fluid communication with third portion 332c of the physiological sample channel 332. Accordingly, the opening 352 is in open and fluid communication with the physiological sample well 330. The cylinder 350 further defines a channel 354 that extends through the cylinder 350. As will be discussed in further detail herein, the opening 352 and the channel 354 allow a physiological sample to exit the cylinder 350 to be deposited onto the specimen collection pad 348.

The second portion 334b of the vacuum channel 334 is in open and fluid communication with the specimen collection pad receptacle 346. Accordingly, the vacuum channel 334 is in open and fluid communication with the physiological sample well 330 via the opening 352 and the physiological sample channel 332.

The specimen collection pad housing 336 further includes a viewing aperture 356 that extends through the top wall 340. Stated another way, the viewing aperture 356 extends between the outer surface 340a and the inner surface 340b of the top wall 340. The viewing aperture 356 provides visual access to the specimen collection pad 348. When the cover 200 is coupled to the base the viewing aperture 356 is located vertically below the viewing aperture 210. As such, a user may view the specimen collection pad 348 when the cover 200 is coupled to the base 300.

Figure 32:
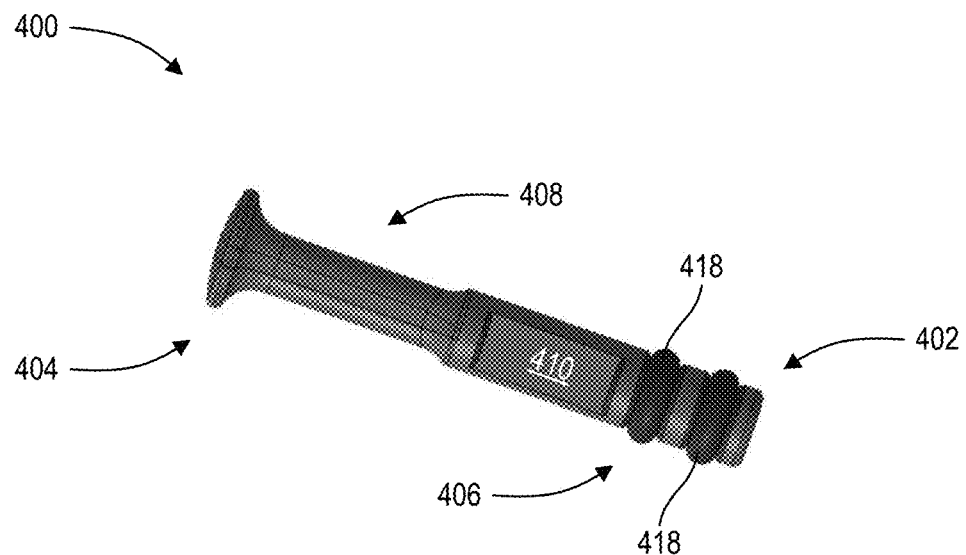
FIGS. 32 and 33 depict a vacuum pin of the dermal patch system in accordance with an exemplary embodiment of the present disclosure.
Figure 33:
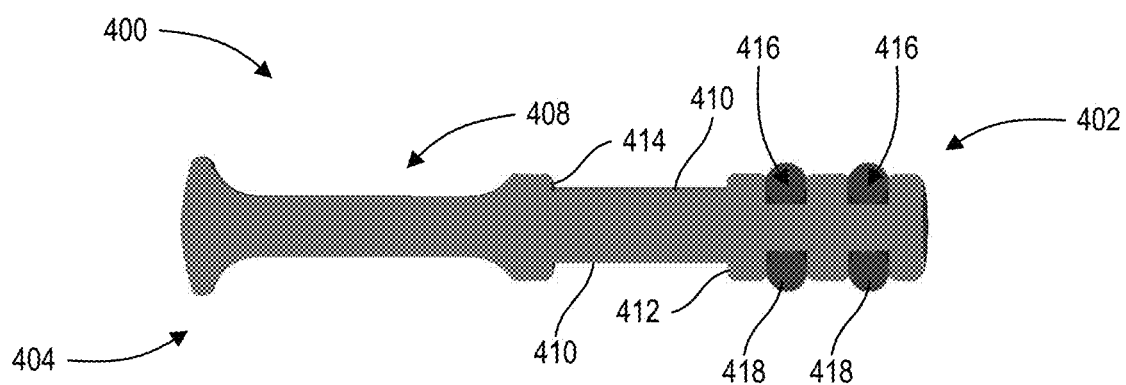

Referring now to FIGS. 32 and 33, the vacuum pin 400 is depicted in accordance with an exemplary embodiment. The vacuum pin 400 is generally cylindrical in shape and extends between a proximal end 402 and a distal end 404. The vacuum pin 400 includes a barrel 406 that defines the proximal end 402 and a handle 408 that defines the distal end 404. The vacuum pin 400 also includes a first and second flat surface 410 between the barrel 406 and the handle 408. The flat surfaces 410 extend longitudinally between a proximal lip 412 and a distal lip 414. The flat surfaces 410 extend perpendicular to and longitudinally between the lips 412 and 414.

The barrel 406 includes a first groove 416 and a second groove 416 shaped and dimensioned to accommodate a first and second elastomeric O-ring 418. When the vacuum pin 400 is disposed within the vacuum pin receptacle 310, the elastomeric O-rings 418 contact the inner surface of the chamber 314 such that the vacuum pin 400 creates an airtight seal within the chamber 314. This seal allows for the application of positive or negative pressure as needed.

The vacuum pin 400 may be moved within or completely removed from vacuum pin receptacle 310. When the vacuum pin 400 is transitioned from a undeployed portion (i.e., a position in which the vacuum pin 400 is fully inserted within the chamber 314 of the vacuum pin receptacle 310) to a deployed position (i.e., when the vacuum pin is moved within the vacuum pin receptacle away from the center of the base 300), a negative pressure is created within the chamber 314, which in turn causes the creation of a negative pressure within the physiological sample channel 332 via the vacuum channel 334 and the specimen collection pad housing 336. When a physiological sample is within the physiological sample well 330, this negative pressure directs the extracted physiological sample from the physiological sample well 330 to the specimen collection pad 348 via the physiological sample channel 332. Stated another way, when the vacuum pin 400 is moved from the undeployed position to the to the deployed position, the vacuum pin 400 creates a vacuum within the base 300 which draws a physiological sample from the physiological sample well 330 to the specimen collection pad 348.

As previously discussed herein, the cover 200 includes a U-shaped locking member 216. When the cover 200 is coupled to base 300 the arms of the U-shaped locking member 216 extend through the gap 316 of the vacuum pin receptacle 310. Furthermore, when the vacuum pin 400 is in the undeployed position, the arms of the U-shaped locking member 216 are disposed between the lips 412 and 414. When the vacuum pin 400 is moved to the deployed position, the arms of the U-shaped locking member 216 contact the proximal lip 412 thereby preventing the vacuum pin 400 from moving further. As previously discussed, moving the vacuum pin 400 to the deployed position creates a vacuum within the base 300. Accordingly, the extent of movement of the vacuum pin 400 permitted by the U-shaped locking member 216 can determine the strength of a vacuum created within the base 300. The lips 412 and 414 are separated by an adjustable distance (the distance can be adjusted by increasing or decreasing the length of the flat surfaces 410). This distance determines the extent by which the vacuum pin 400 can be removed from the vacuum pin receptacle 310 and as such can determine the strength of a vacuum created within the base 300. Hence, increasing or decreasing a distance between lips 412 and 414 increases or decreases the strength of a vacuum that can be created by the vacuum pin 400.

Figure 34:
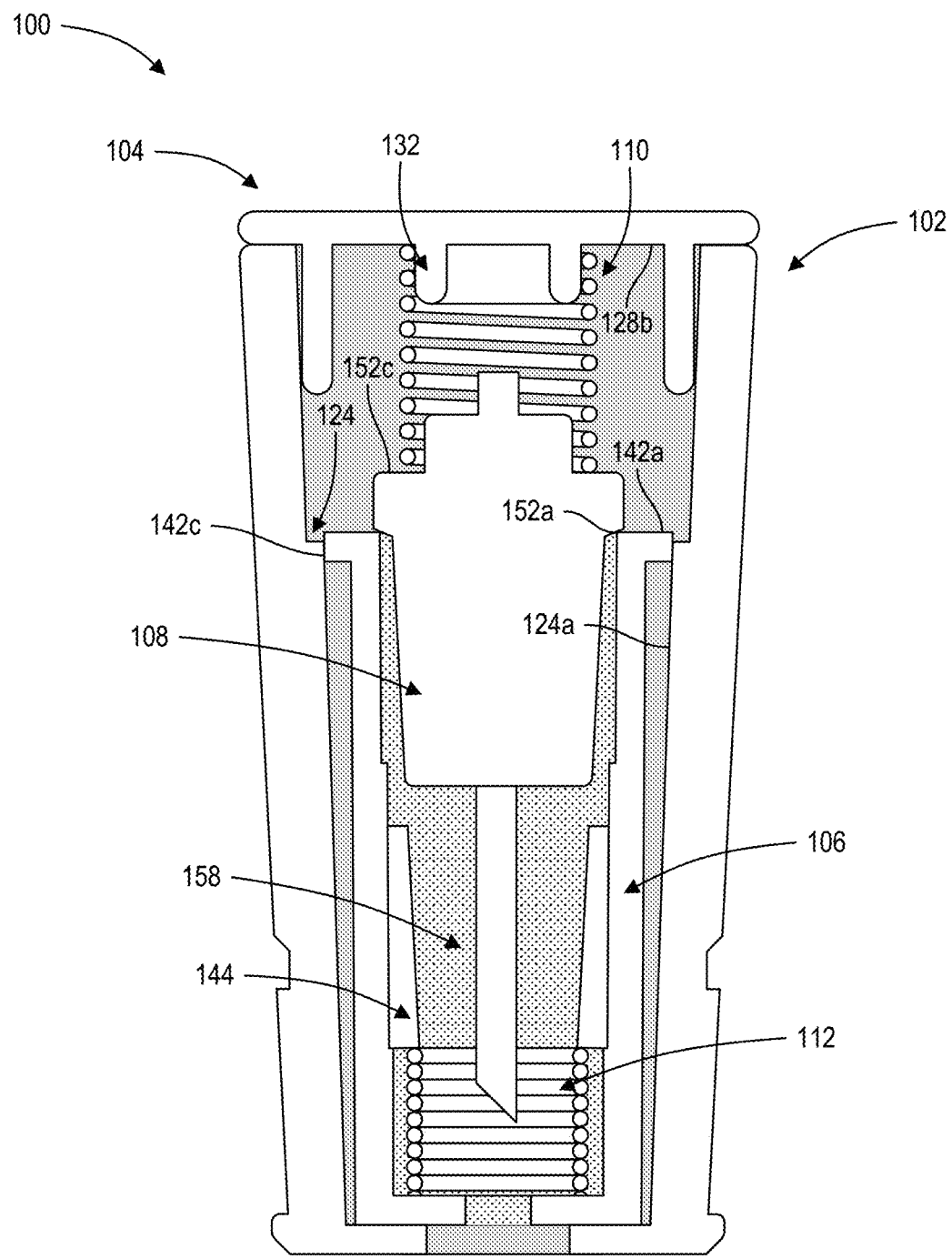
FIG. 34 diagrammatically depicts a lancet of the dermal patch system in an undeployed position in accordance with an exemplary embodiment of the present disclosure.
Figure 35:
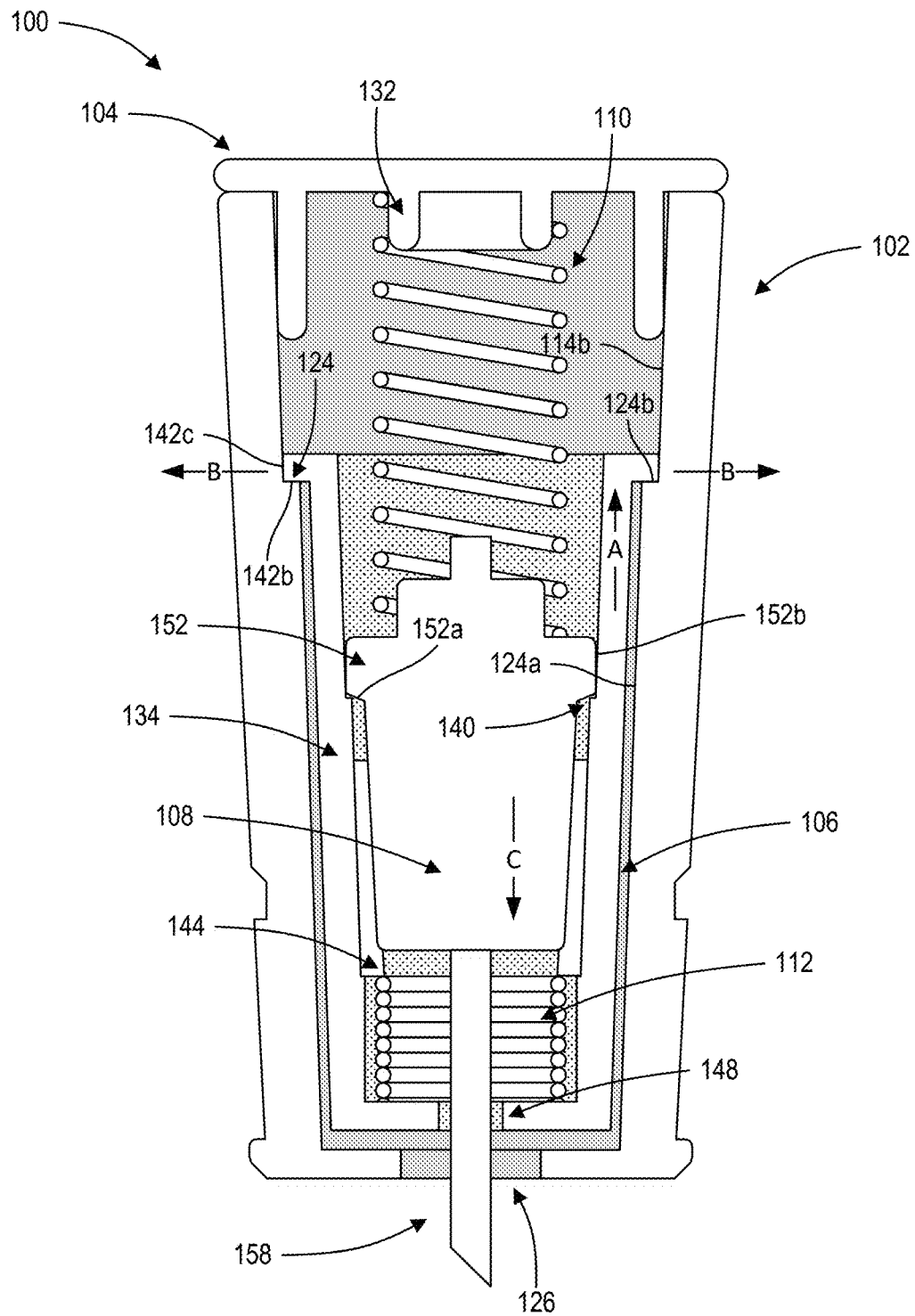
FIG. 35 diagrammatically depicts a lancet of the dermal patch system in a deployed position in accordance with an exemplary embodiment of the present disclosure.
Figure 36:
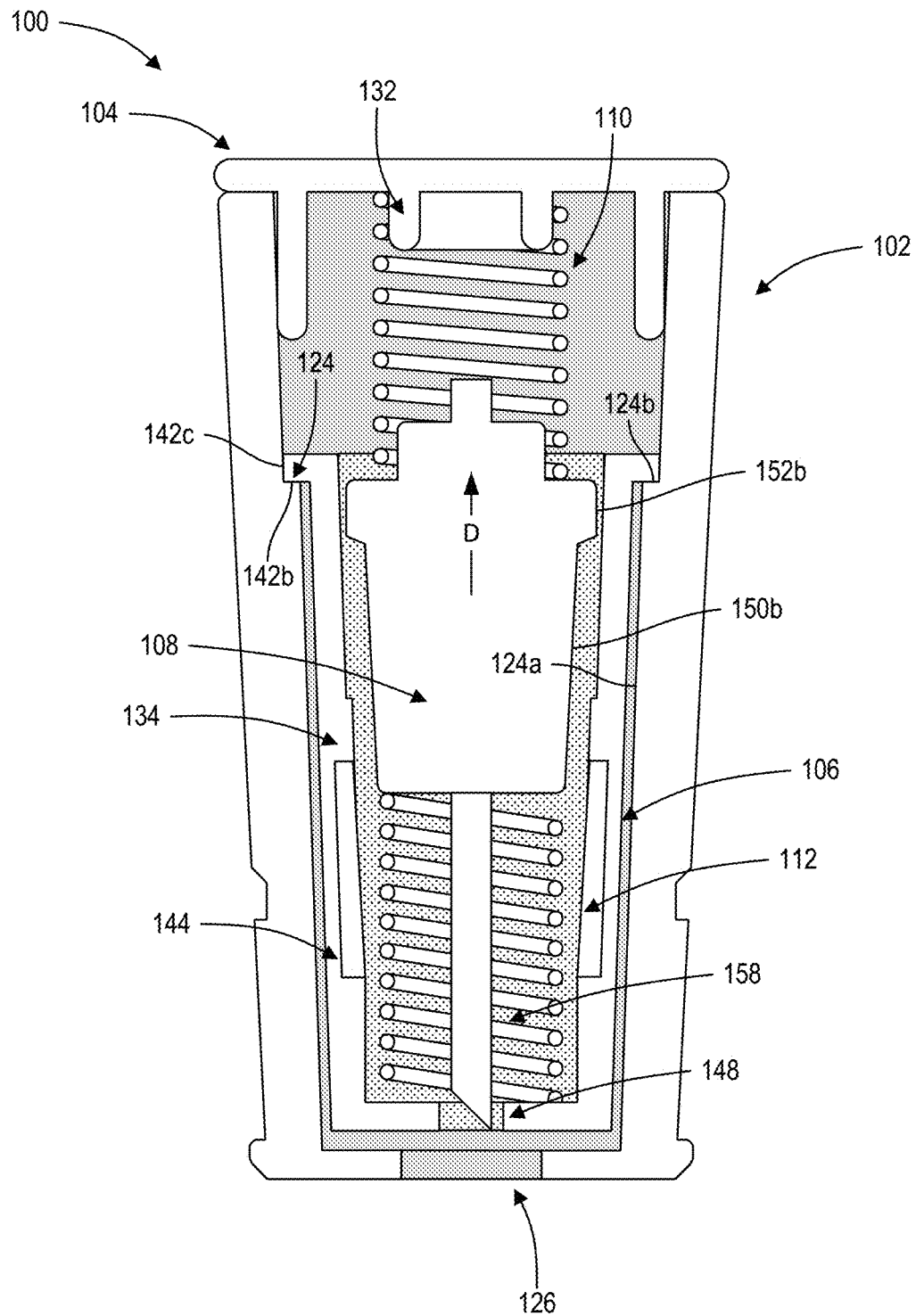
FIG. 36 diagrammatically depicts a lancet of the dermal patch system in a retracted position in accordance with an exemplary embodiment of the present disclosure.

As depicted in FIGS. 34-36, the lancet 100 is moveable between an undeployed position (FIG. 34), a deployed position (FIG. 35), and a retracted position (FIG. 36).

In the undeployed position (before the lancet 100 is inserted into the cartridge 12) the injection spring 110 and the retraction spring 112 are in a compressed state. In the compressed state, the retraction spring 112 extends vertically between the bottom wall 136 and a proximal end of the locking members 144. More specifically, a distal end of the retraction spring 112 contacts a lower surface of the proximal end of the locking members 144 and a proximal end of the retraction spring 112 contacts the inner surface 136b of the bottom wall 136.

When in the undeployed position the outer surface 142c contacts the inner surface 124a of the columns 124 which compresses the side wall 134 inwardly. Furthermore, the bottom surface 152a of the second cylinder 152 contacts and rests upon the top surfaces 142a of the ledges 142 such that the ledges 142 supports the needle frame 108 in the undeployed position. In this position, the injection spring 110 is prevented from decompressing (due to the second cylinder 152 resting upon the ledges 142) and the needle 158 is disposed completely within the inner volume 138 of the inner sleeve 106.

When the lancet 100 is inserted into the cartridge 12, the engagement of the lancet with the cartridge 12 causes the lancet 100 to automatically move from the undeployed position to the deployed position and the rim 304 contacts the inner surface 322b of the outer circular projection 322. Furthermore, when the lancet 100 is inserted into the cartridge 12, the hooks 328 of the locking members 326 are disposed within and coupled to the notch 120 via a snap fit.

Figure 37:
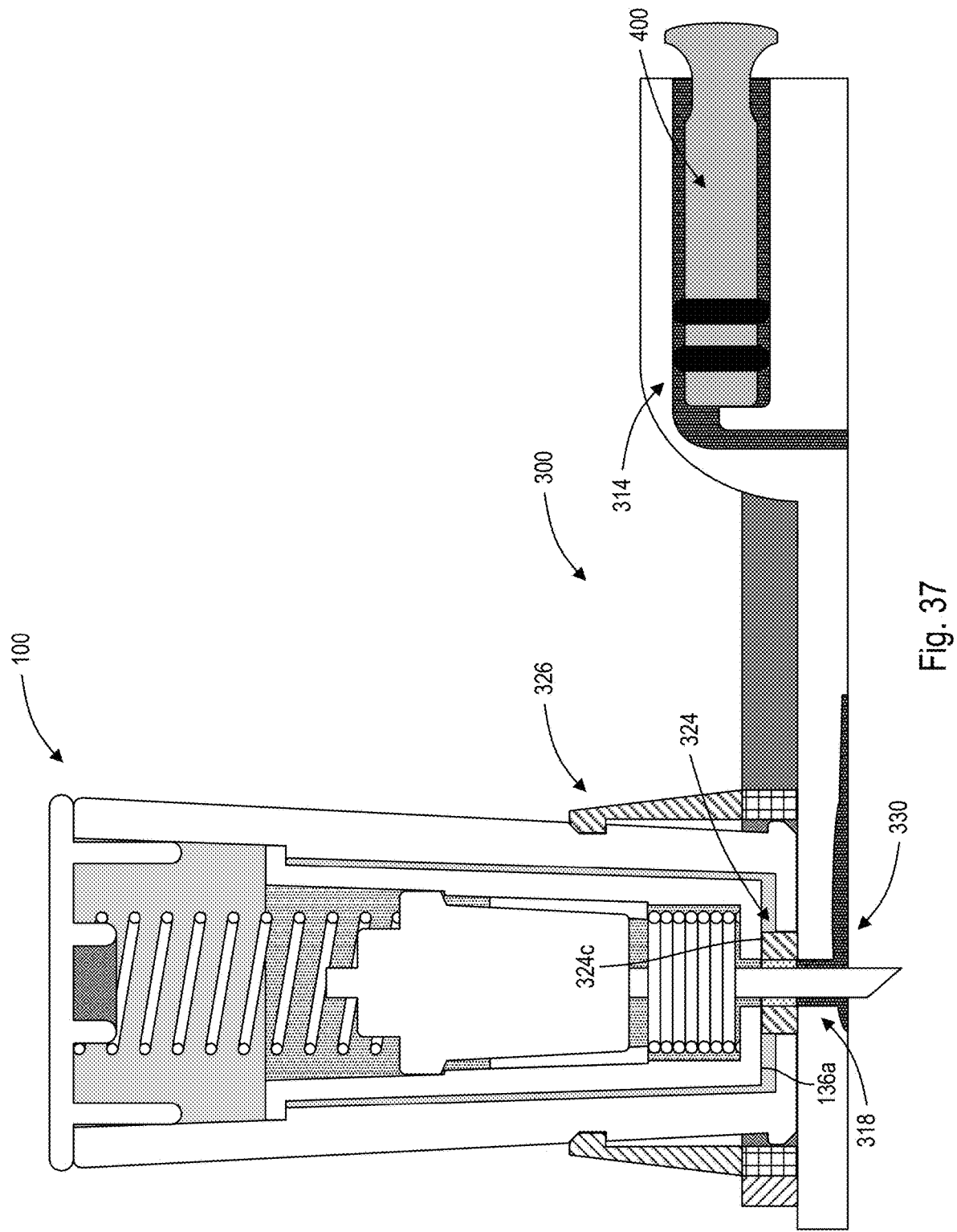
FIG. 37 diagrammatically depicts a dermal patch system with the lancet in a deployed position and a vacuum pin in an undeployed position in accordance with an exemplary embodiment of the present disclosure.

When the lancet 100 is coupled to the base 300 (FIGS. 37 and 38), the inner circular projection 324 extends through the aperture 126 to contact the bottom wall 136. Specifically, the top surface 324c of the inner circular projection 324 contacts the outer surface 136a of the bottom wall 136 which forces the inner sleeve 106 to move vertically upward in the direction of arrow A within the housing 102. This vertical movement causes the ledges 142 to extend vertically above the top surfaces 124b of the columns 124. Moving beyond the top surfaces 124b of the columns 124 allows the side wall 134 to decompress and expand in the direction of arrow B and extend toward the inner surface 114b of the side wall 114. In this position, the bottom surface 142b of the ledges 142 rest upon the top surfaces 124b of the columns 124 and the outer surfaces 142c of the ledges 142 contacts the inner surface 114b of the side wall 114.

The expansion of the side wall 134 causes the inner volume 138 of the inner sleeve 106 to have a larger width relative to when the inner sleeve 106 is in the undeployed position such that at least a portion of the side wall 134 has a larger width than the second cylinder 152 (the widest portion of the needle frame 108 which allows the needle frame 108 move vertically downward in the direction of arrow C). Furthermore, the injection spring 110 also causes the needle frame 108 to move in the direction of arrow C as the ledges 142 no longer prevent the injection spring 110 from expanding. The force applied by the injection spring 110 causes the needle frame 108 (and therefore the needle 158) to travel with a force that is sufficient to cause the needle 158 to puncture the skin of a subject wearing the dermal patch system 10. Stated another way, the injection spring 110 causes the needle 158 to extend through the aperture 148 of the inner sleeve 106, through the aperture 126 of the housing 102, and through the needle aperture 318 of the base 300 to puncture the skin of a subject. In the deployed position, the bottom surface 152a of the second cylinder 152 rests upon the columns 140 and at least a portion of the outer surface 152b of the second cylinder 152 contacts the inner surface 134b of the side wall 134.

Figure 38:
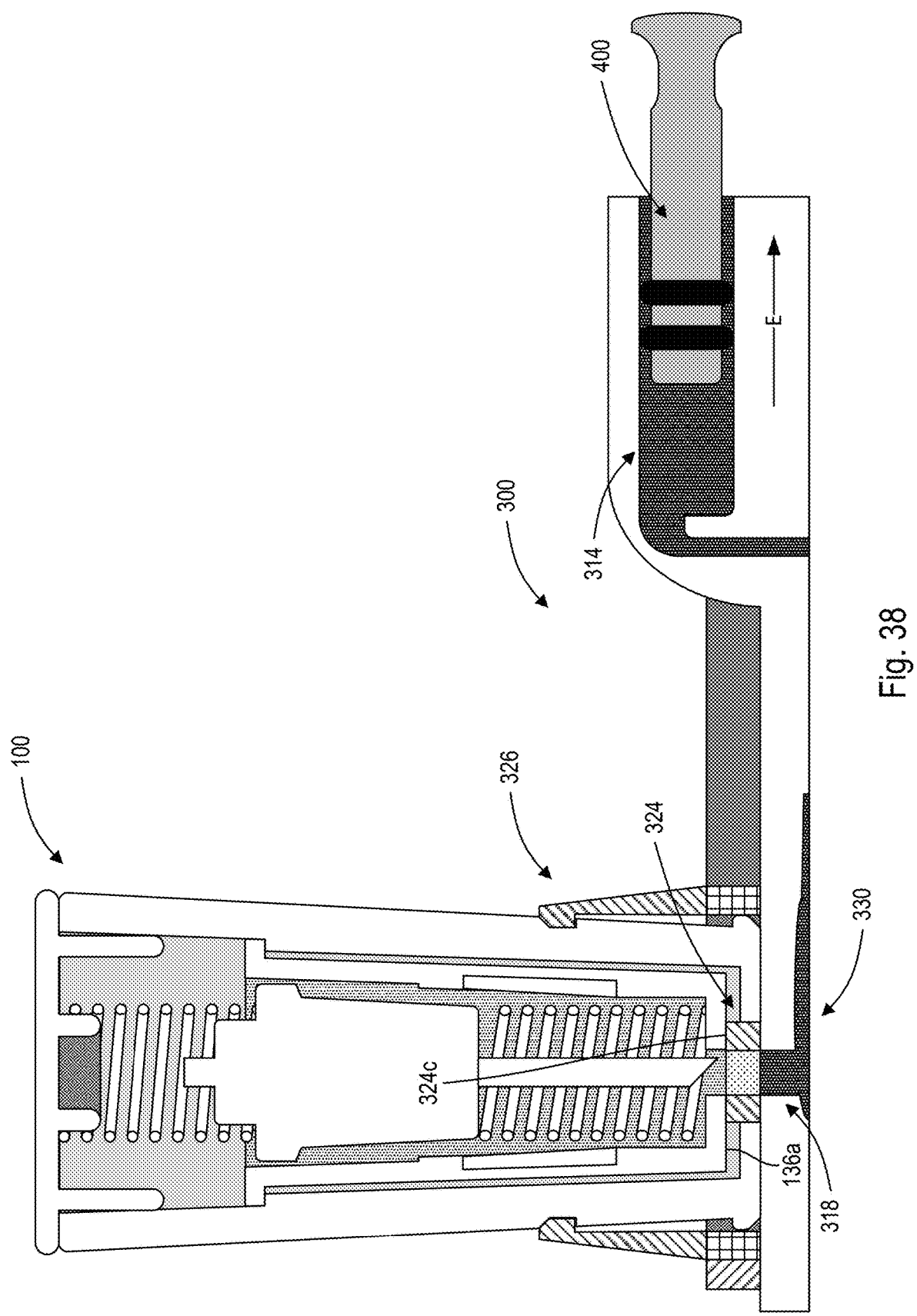
FIG. 38 diagrammatically depicts the dermal patch system with the lancet in a retracted position and a vacuum pin in a deployed position in accordance with an exemplary embodiment of the present disclosure.

While moving in the direction of arrow C, the outer surface 150b contacts the locking members 144 which causes a proximal portion of a locking members 144 that is aligned with an opening 146 to extend into the opening. In this position, the locking members 144 no longer contact the retraction spring 112 thereby allowing the retraction spring 112 to decompress and expand. When decompressed, the retraction spring 112 contacts the outer surface 150b of the first cylinder 150 which causes needle frame 108 to also move in the direction of arrow D. That is after moving to the deployed position, the retraction spring 112 causes the needle 158 to retract back into the inner volume 138 of the inner sleeve 106 via the needle aperture 318 of the base 300 and the apertures 126 and 148 of the lancet 100. After penetrating the skin of a subject, the retraction spring 112 causes the needle 158 to automatically retract back into the housing of the lancet 100 thereby placing the lancet 100 in the retracted position (FIGS. 36 and 38).

After the needle 158 retracts into the lancet 100, a physiological sample pools within the physiological sample well 330 of the base 300. When the physiological sample is within the physiological sample well 330, a user can move the vacuum pin 400 from the undeployed position to the deployed position in the direction of arrow E (FIG. 38) thereby creating a vacuum within the base 300 as previously discussed herein. This vacuum causes physiological sample to travel to the specimen collection pad 348 via the physiological sample channel 332 as previously discussed herein. With the physiological sample on the specimen collection pad 348 the dermal patch system 10 can be removed from the skin of the subject. Once removed, a user can separate the specimen collection pad 348 from the cartridge 12 by pulling the pull tab 18 which causes the perforation 20 to tear which allows the removal of the specimen collection pad 348 and analysis of the physiological sample captured by the specimen collection pad 348 by a medical professional. In some embodiments, a user of the dermal patch system 10 may send the separated specimen collection pad 348 with the physiological sample to a laboratory for analysis.

As previously discussed herein, a mechanism can be transitioned between a locked state and a released state. This mechanism includes the columns 124, the ledges 142, and the locking members 144. An upper locking portion of the mechanism refers to the columns 124 and the ledges 142 while a locker locking portion refers to the locking members 144 as the columns 124 and the ledges 142 can be positioned vertically above the locking members 144. The term upper interference portion refers to the top surface 142a of the ledges 142 as this surface interferes with the needle frame's 108 ability to transfer to the deployed position when the mechanism is in the locked state. As used herein, a lower interference member refers to the columns 140 as the columns 140 interfere with the needle frame's 108 ability to further extend beyond a desired position.

Referring now to FIGS. 39-42, the dermal patch system 10 with a specimen collection pad cartridge 500 is shown in accordance with an exemplary embodiment. In the figures and description herein, like reference numerals refer to previously discussed like elements and may not be further discussed for the sake of brevity.

Figure 39:
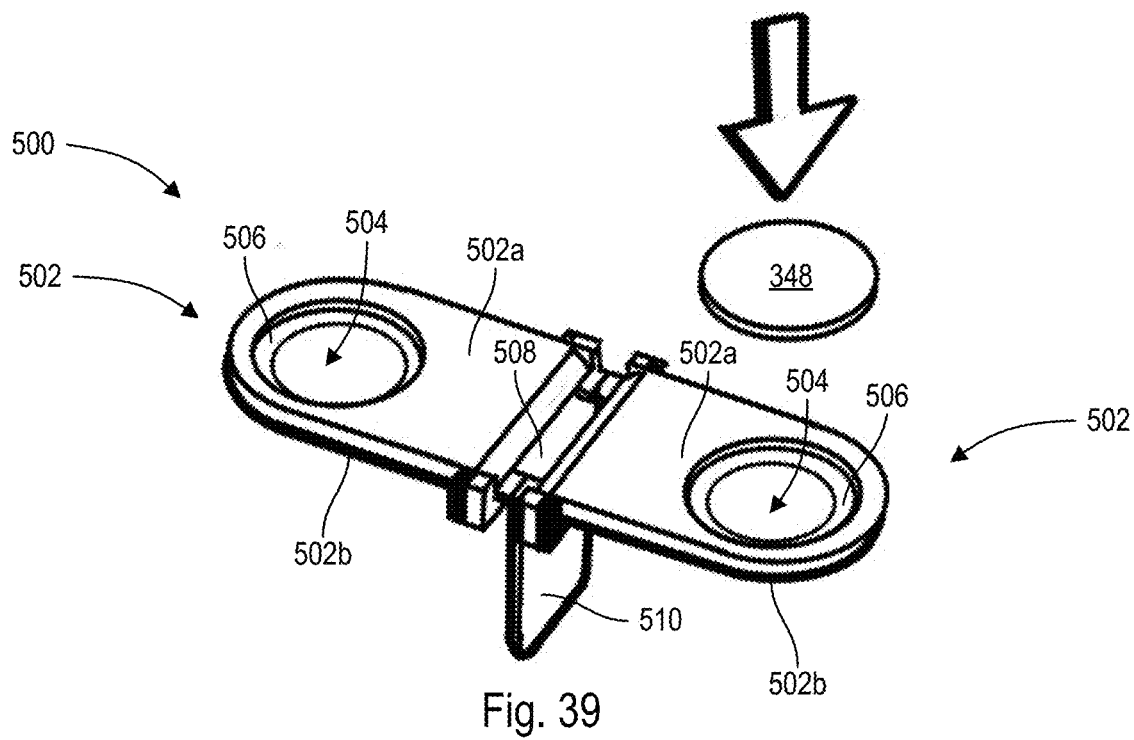
FIG. 39 diagrammatically depicts a specimen collection pad cartridge in an open position in accordance with an exemplary embodiment of the present disclosure.

As depicted in FIG. 39, the specimen collection pad cartridge 500 includes a first and second specimen collection pad holder 502. The specimen collection pad holders 502 include a top surface 502a and an opposed bottom surface 502b and an opening 504 that extends between the top surface 502a and the bottom surface 502b. The specimen collection pad holders 502 also include a specimen collection pad tray 506 that extends longitudinally from and perpendicular to an inner surface of the opening 504. The openings 504 and the specimen collection pad tray 506 are shaped and dimensioned to accommodate the specimen collection pad 348.

Figure 40:
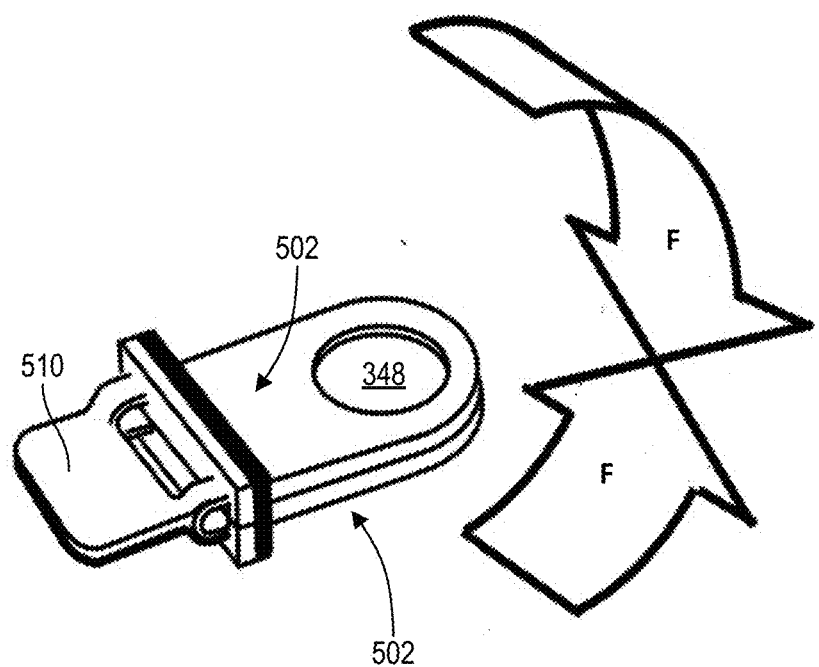
FIG. 40 diagrammatically depicts a specimen collection pad cartridge in a closed position in accordance with an exemplary embodiment of the present disclosure.

The specimen collection pad cartridge 500 further includes a hinge 508 that is coupled to the specimen collection pad holders 502. The hinge 508 allows the specimen collection pad cartridge 500 to move between an open position (FIG. 39) and a closed position (FIG. 40). In the open position, each specimen collection pad holder 502 can accept a specimen collection pad 248. After placing a specimen collection pad 248 into one of the specimen collection pad holders 502, a user can move the specimen collection pad holders 502 in the direction of arrow F to place the specimen collection pad cartridge 500 in the closed position.

The specimen collection pad cartridge 500 also includes a pull tab 510 that is coupled to the hinge 508. As will be discussed in further detail herein, the pull tab 510 allows a user of the dermal patch system 10 to remove the specimen collection pad cartridge 500 from the base 300.

Figure 41:
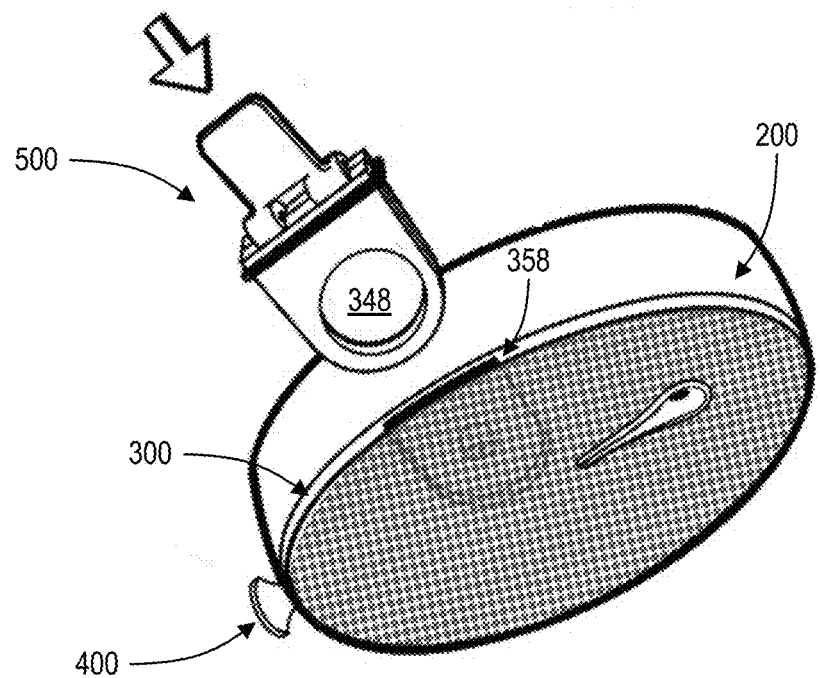
FIG. 41 diagrammatically depicts a specimen collection pad cartridge being inserted into the dermal patch system in accordance with an exemplary embodiment of the present disclosure.
Figure 42:
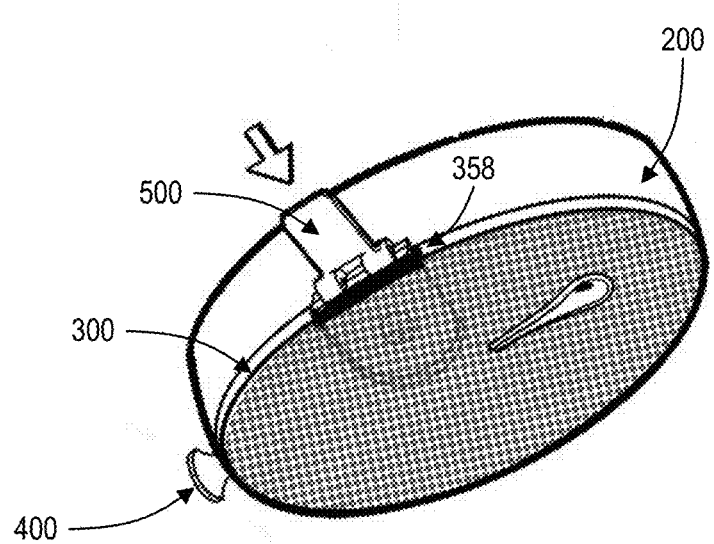
FIG. 42 diagrammatically depicts a specimen collection pad cartridge inserted within the dermal patch system in accordance with an exemplary embodiment of the present disclosure.

With reference to FIGS. 41 and 42, in this embodiment, the base 300 is modified to include an opening 358 that is shaped and dimensioned to accept the specimen collection pad holders 502 in the closed position. Further, in this embodiment, the surface 344 is modified to also accept the specimen collection pad holders 502. Accordingly, the specimen collection pad receptacle 346 is shaped and dimensioned to accept the specimen collection pad holders 502. The opening 358 is in open communication with the specimen collection pad receptacle 346. As such, a user can insert the specimen collection pad holders 502 into the specimen collection pad receptacle 346 via the opening 358. The adhesive layer 14 covers the opening 358 and the specimen collection pad receptacle 346 such that the adhesive layer 14 seals the specimen collection pad holders 502 within the specimen collection pad receptacle 346.

When a specimen collection pad cartridge 500 with a specimen collection pad 348 is disposed within the specimen collection pad receptacle 346, the specimen collection pad 348 can receive a physiological sample via the opening 352 of the cylinder as previously discussed herein. After collecting a physiological sample, and removal of the dermal patch system 10 from the subject's skin, a user can remove the specimen collection pad cartridge 500 from the cartridge 12 by pulling the pull tab 510. After removal, a user can open the specimen collection pad cartridge 500 to expose the specimen collection pad 348. Once removed, the specimen collection pad 348 can be sent to a laboratory for further analysis.

Figure 43:
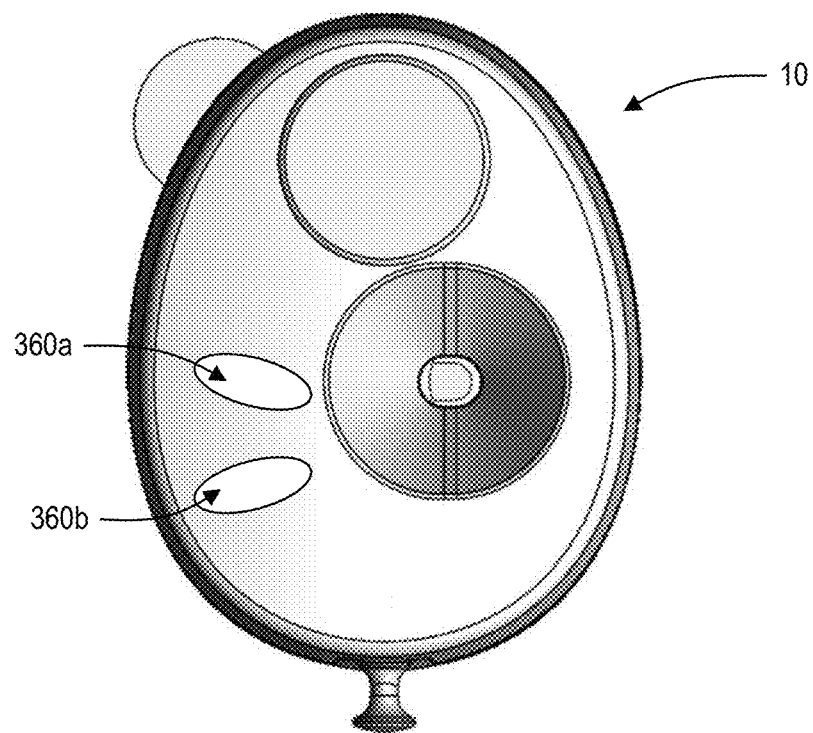
FIG. 43 depicts a dermal patch system with pipette access channels in accordance with an exemplary embodiment of the present disclosure.
Figure 44:
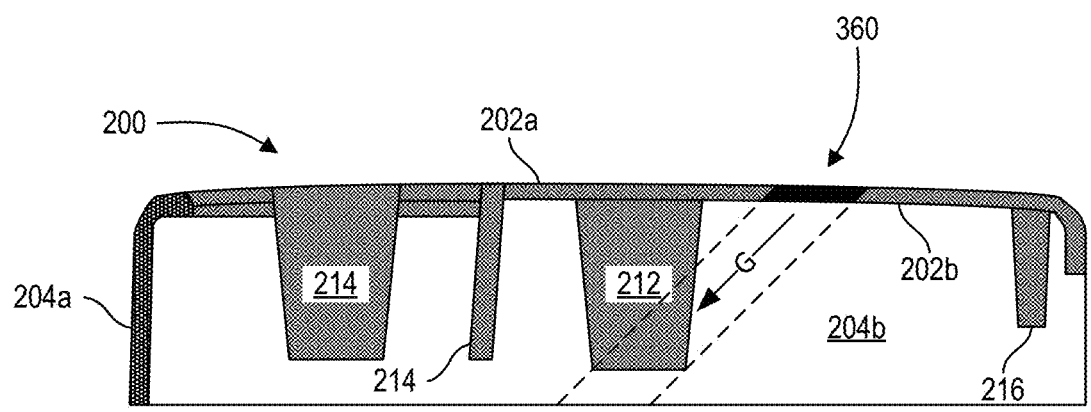
FIG. 44 diagrammatically depicts a cover of the dermal patch system with pipette access channels in accordance with an exemplary embodiment of the present disclosure.

Referring now to FIGS. 43 and 44, the cover 200 with a first pipette access channel 360a and a second pipette access channel 360b is shown in accordance with an exemplary embodiment. In the figures and description herein, like reference numerals refer to previously discussed like elements and may not be further discussed for the sake of brevity.

The pipette access channels 360 extends at an angle (e.g., 45°) through the top wall 202. Stated another way, the pipette access channels 360 extend at an angle between the outer surface 202a and the inner surface 202b. The pipette access channels 360 are shaped and dimensioned to accommodate a tip and at least a portion of a neck of a pipette (e.g., a micropipette). When the cover 200 is coupled to the base 300, the angle and position of the pipette access channels 360 directs a pipette towards the specimen collection pad 348.

That is, in operation, a user may insert a tip of a pipette into the pipette access channels 360, extend at least a portion of the pipette through the pipette access channel 360 in the direction of arrow G to access the specimen collection pad 348 via the viewing aperture 356. In order to ensure the tip of the pipette has access to the specimen collection pad 348, the user may view the specimen collection pad 348 and the pipette via the viewing aperture 210.

A medical professional may obtain at least a portion of a drawn physiological sample absorbed by the collection pad via a pipette. In these embodiments, a pipette that holds a processing fluid (e.g., phosphate-buffered saline) may be inserted into the dermal patch system 10 via the first pipette access channel 360a. Once the pipette is vertically above or contacts the specimen collection pad 348, the medical professional may release the processing fluid from the pipette onto the specimen collection pad 348. The processing fluid may then interact with at least a portion of a physiological sample held by the specimen collection pad 348 to form a solution that includes physiological sample (also referred to as a "processed physiological sample"). The medical professional may then use the same or a different pipette to then withdraw the processed physiological sample from the specimen collection pad 348 via the second pipette access channel 360b. The processed physiological sample may then be further analyzed.

While FIGS. 43 and 44 depict the cover 200 as including two pipette access channels 360, in other embodiments, the cover 200 may include one pipette access channel 360. In these embodiments, a medical professional inserts a pipette with the processing fluid to create the processed physiological sample and withdraws the processed physiological sample via the same pipette access channel 360.

Figure 45:
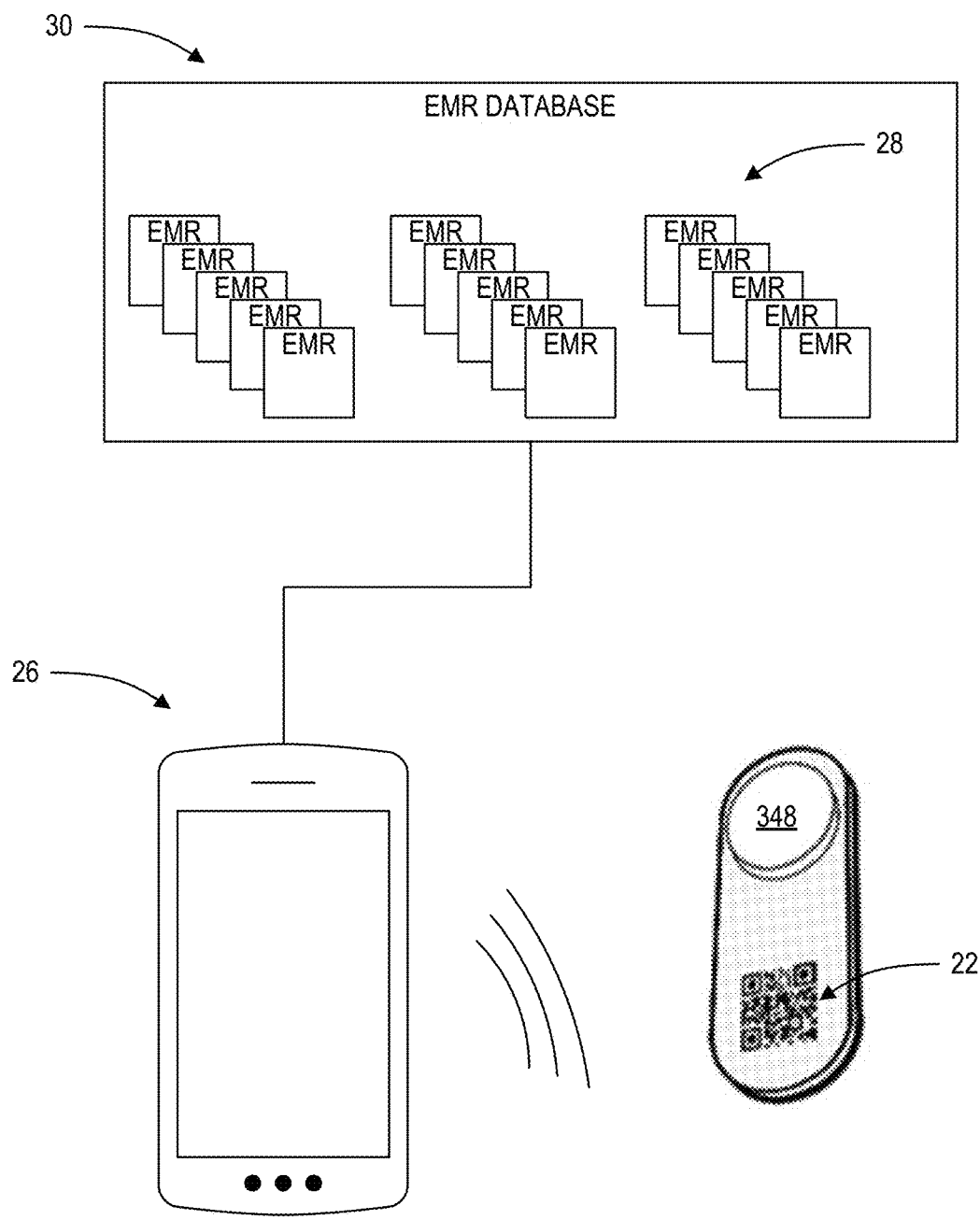
FIG. 45 diagrammatically depicts an electronic medical record database, a computer system, and a physiological sample collection pad with a quick response ("QR") code in accordance with an exemplary embodiment of the present disclosure.

With reference to FIG. 45, in some embodiments wherein the cartridge 12 includes the QR code 22, a user of a computer system 26 may scan the QR code 22 to update an EMR 28 stored in an EMR database 30 that is in communication with the computer system 26. The user of the computer system may scan the QR code 22 before or after obtaining the physiological sample depending upon the location of the QR code 22 (e.g., on the outer surface 202*a* of the top wall 202 or on the adhesive layer 14).

In these embodiments, the computer system 26 may include an application that provides access to the EMR database 30 via a network connection and allows the user to photograph or scan the QR code 22. As shown in FIG. 45, the EMR database 30 includes a plurality of EMRs 28 each of which is associated with an individual subject. The application causes the computer system 26 to scan or retrieve an image of the QR code 22, analyze the QR code 22 and associate the QR code 22 with an EMR 28. In some embodiments, the computer system 26 may then update the associated EMR 28 to indicate a physiological sample has been obtained. The computer system 26 may update the EMR 28 automatically or based on a user input.

Figure 46:
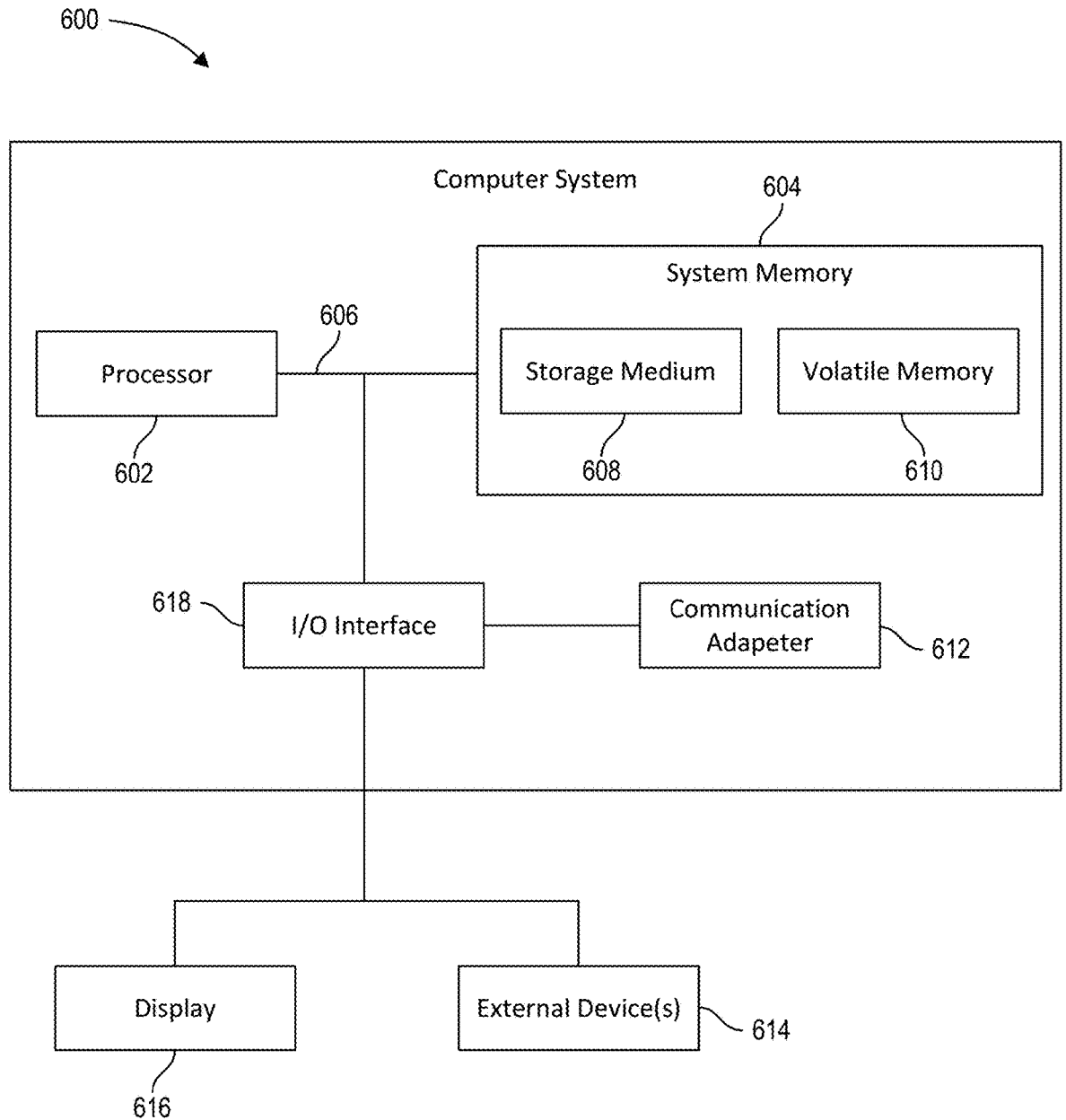
FIG. 46 diagrammatically depicts a computer system in accordance with an exemplary embodiment of the present disclosure.

Referring now to FIG. 46, a computer system 600 is shown in accordance with an exemplary embodiment. The computer system 600 may serve as any computer system disclosed herein (e.g., the computer system 26). As used herein a computer system (or device) is any system/device capable of receiving, processing, and/or sending data. Computer systems include, but are not limited to, microprocessor-based systems, personal computers, servers, hand-held computing devices, tablets, smartphones, multiprocessor-based systems, mainframe computer systems, virtual reality ("VR") headsets and the like.

As shown in FIG. 46, the computer system 600 includes one or more processors or processing units 602, a system memory 604, and a bus 606 that couples the various components of the computer system 600 including the system memory 604 to the processor 602. The system memory 604 includes a computer readable storage medium 608 and volatile memory 610 (e.g., Random Access Memory, cache, etc.). As used herein, a computer readable storage medium includes any media that is capable of storing computer readable; program instructions and is accessible by a processor. The computer readable storage medium 608 includes non-volatile and non-transitory storage media (e.g., flash memory, read only memory (ROM), hard disk drives, etc.). Computer program instructions as described herein include program modules (e.g., routines, programs, objects, components, logic, data structures, etc.) that are executable by a processor. Furthermore, computer readable program instructions, when executed by a processor, can direct a computer system to function in a particular manner such that a computer readable storage medium comprises an article of manufacture. Specifically, the computer readable program instructions when executed by a processor can create a means for carrying out at least a portion of the steps of the methods disclosed herein.

The bus 606 may be one or more of any type of bus structure capable of transmitting data between components of the computer system 600 (e.g., a memory bus, a memory controller, a peripheral bus, an accelerated graphics port, etc.).

The computer system 600 may further include a communication adapter 612 which allows the computer system 600 to communicate with one or more other computer systems/devices via one or more communication protocols (e.g., Wi-Fi, BTLE, etc.) and in some embodiments may allow the computer system 600 to communicate with one or more other computer systems/devices over one or more networks (e.g., a local area network (LAN), a wide area network (WAN), a public network (the Internet), etc.).

In some embodiments, the computer system 600 may be connected to one or more external devices 614 and a display 616. As used herein, an external device includes any device that allows a user to interact with a computer system (e.g., mouse, keyboard, touch screen, etc.). An external device 614 and the display 616 may be in communication with the processor 602 and the system memory 604 via an Input/Output (I/O) interface 618.

The display 616 may display a graphical user interface (GUI) that may include a plurality of selectable icons and/or editable fields. A user may use an external device 614 (e.g., a mouse) to select one or more icons and/or edit one or more editable fields. Selecting an icon and/or editing a field may cause the processor 602 to execute computer readable program instructions stored in the computer readable storage medium 608. In one example, a user may use an external device 614 to interact with the computer system 600 and cause the processor 602 to execute computer readable program instructions relating to at least a portion of the steps of the methods disclosed herein.

Figure 47:
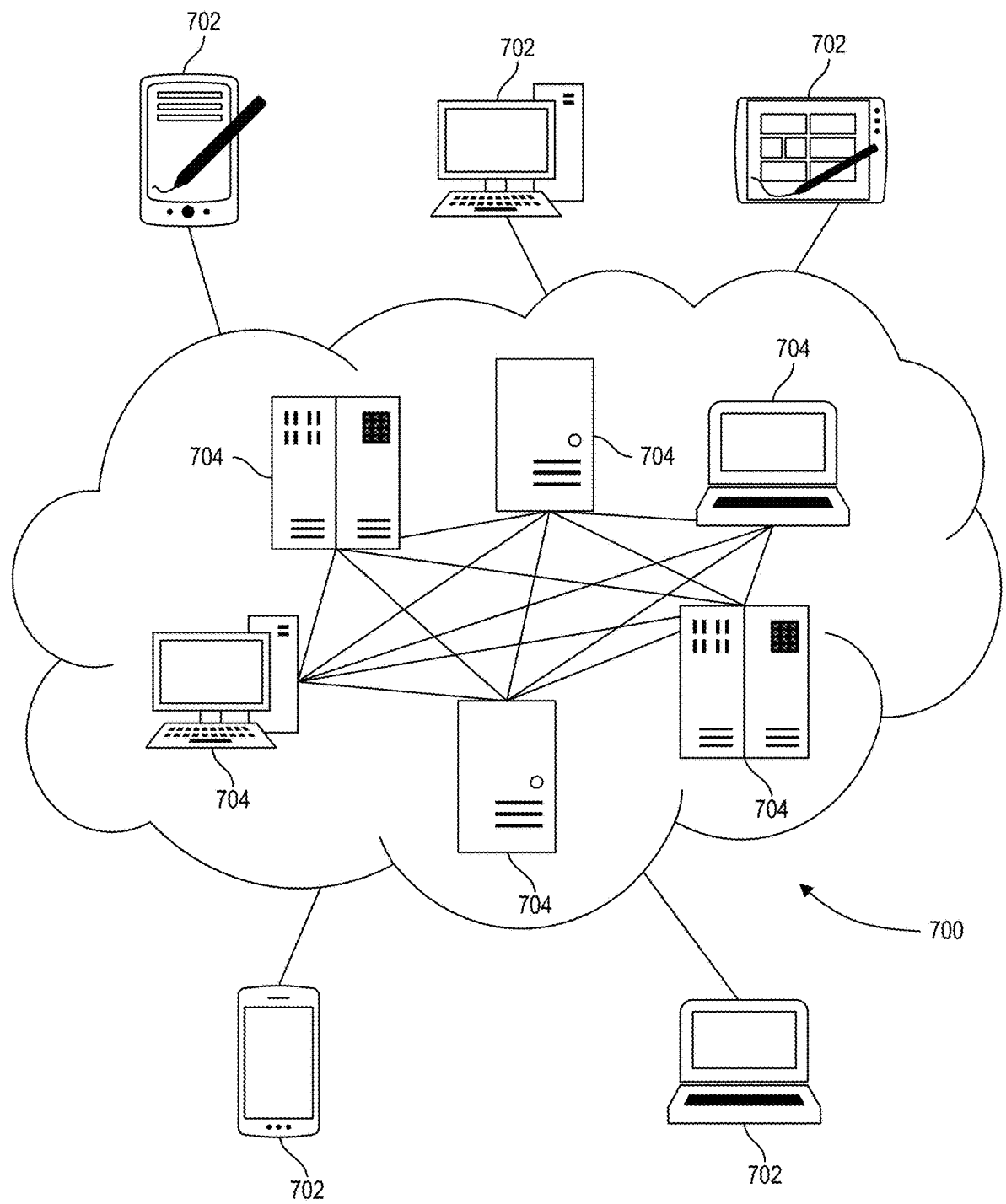
FIG. 47 diagrammatically depicts a cloud computing environment in accordance with an exemplary embodiment of the present disclosure.

Referring now to FIG. 47, a cloud computing environment 700 is depicted in accordance with an exemplary embodiment. The cloud computing environment 700 is connected to one or more user computer systems 702 and provides access to shared computer resources (e.g., storage, memory, applications, virtual machines, etc.) to the user computer systems 702. As depicted in FIG. 47, the cloud computing environment includes one or more interconnected nodes 704. Each node 704 may be a computer system or device local processing and storage capabilities. The nodes 704 may be grouped and in communication with one another via one or more networks. This allows the cloud computing environment 700 to offer software services to the one or more computer services to the one or more user computer systems 702 and as such, a user computer system 702 does not need to maintain resources locally.

In one embodiment, a node 704 includes computer readable program instructions for carrying out various steps of various methods disclosed herein. In these embodiments, a user of a user computer system 702 that is connected to the cloud computing environment may cause a node 704 to execute the computer readable program instructions to carry out various steps of various methods disclosed herein.

Figure 48:
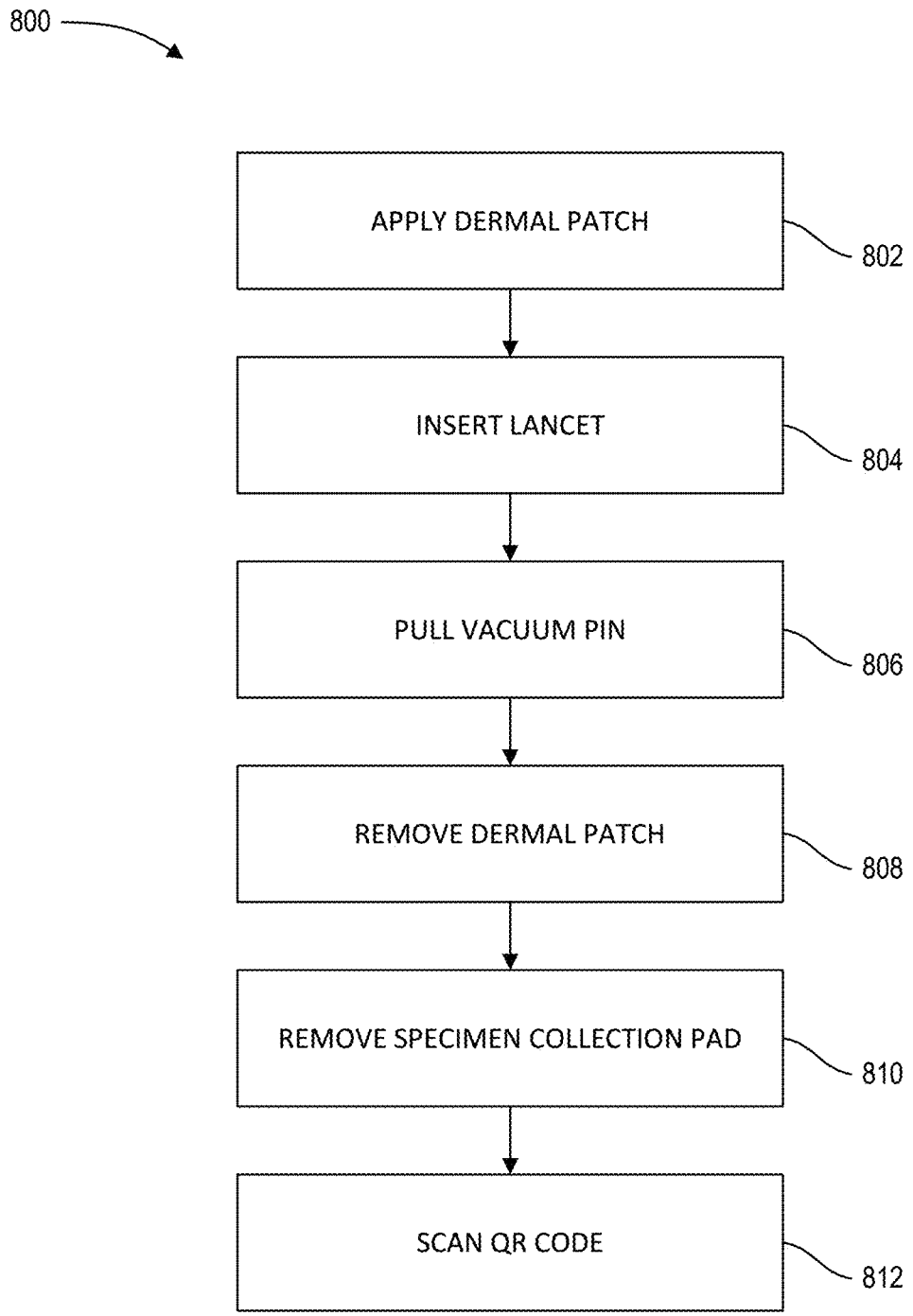
FIG. 48 is a flow chart of a method for obtaining a physiological sample from a subject in accordance with an exemplary embodiment of the present disclosure.

Referring now to FIG. 48, a method 800 for obtaining a physiological sample from a subject is shown in accordance with an exemplary embodiment.

At 802, a user (e.g., a medical professional, a subject, etc.) applies the cartridge 12 to the skin of the subject via the adhesive layer 14 at a suitable location (e.g., on a leg, arm, etc.) as previously discussed herein.

At 804, the user inserts the lancet 100 into the cartridge 12 thereby causing the needle 158 of the lancet 100 to draw a physiological sample (e.g., a blood sample, a sample of interstitial fluid, etc.) from the subject as previously discussed herein.

At 806, the user pulls the vacuum pin 400 to draw the physiological sample to the specimen collection pad 348 as previously discussed herein.

At 808, the user removes the dermal patch system 10 from the skin of the subject as previously discussed herein.

At 810, the user removes the physiological sample collection pad from the cartridge 12 (e.g., by causing the perforation 20 to tear) as previously discussed herein. In some embodiments, after removing the specimen collection pad 348 the user sends the specimen collection pad 348 to a laboratory for further analysis by a medical professional.

At 812, a user of the computer system 26 scans the QR code 22 and updates an EMR 28 to indicate a physiological sample was collected from the subject as previously discussed herein.

As previously discussed, some of the steps of the various methods disclosed herein may be implemented by way of computer readable instructions, encoded or embedded on computer readable storage medium (which excludes transitory medium), which, when executed by a processor(s), cause the processor(s) to carry out various steps of the methods of the present disclosure.

While various embodiments have been illustrated and described in detail in the drawings and foregoing description, such illustration and description are to be considered illustrative or exemplary and not restrictive; embodiments of the present disclosure are not limited to the disclosed embodiments. Other variations to the disclosed embodiments can be understood and effected by those skilled in the art in practicing embodiments of the present disclosure, from a study of the drawings, the disclosure, and the appended claims.

In the claims, the word "comprising" does not exclude other elements or steps, and the indefinite article "a" or "an" does not exclude a plurality. A single processor or other processing unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

What is claimed is:

1. A device for collecting a physiological sample from a subject, comprising:
   a lancet having a needle configured to puncture the subject's skin;
   a cartridge configured to engage with the lancet, wherein the lancet is configured to automatically transition the needle from an undeployed position to a deployed position in response to engagement with the cartridge, thereby allowing the needle to puncture the subject's skin;
   a specimen collection pad housing with a specimen collection pad disposed therein,
   a physiological sample well;
   a physiological sample channel in open communication with the physiological sample well and the specimen collection pad housing; and
   a lancet aperture in open communication with the physiological sample well, wherein the lancet aperture and the physiological sample well are configured to allow the needle to extend therethrough to puncture the skin of the subject when the device is affixed to the subject's skin.

2. The device of claim 1, wherein the specimen collection pad is removable.

3. The device of claim 1, further comprising:
   an adhesive layer affixed to the cartridge,
      wherein the specimen collection pad is attached to the adhesive layer.

4. The device of claim 1, wherein at least a portion of the physiological sample channel is three sided.

5. The device of claim 1, further comprising a removable cover.

6. The device of claim 5, wherein the cover and the specimen collection pad housing each include a viewing aperture that provide visual access to the specimen collection pad disposed within the specimen collection pad housing.

* * * * *